United States Patent [19]

Fujii et al.

[11] Patent Number: 5,374,653
[45] Date of Patent: Dec. 20, 1994

[54] IRIDOID DERIVATIVES AND THE USE THEREOF AS A DRUG

[75] Inventors: Yuichi Fujii; Ichiro Arai; Akira Hatta, all of Inashiki; Akemi Tatsugi, Tokyo; Hiroshi Mitsuhashi, deceased, late of Inashiki; Mieko Mitsuhashi, legal representative, Tokyo; Hiroyuki Mitsuhashi, legal representative, Rumoi; Tomoaki Mitsuhashi, legal representative, Tokyo; Masaharu Kigawa, Inashiki, all of Japan

[73] Assignee: Tsumura & Co., Tokyo, Japan

[21] Appl. No.: 107,158

[22] Filed: Aug. 17, 1993

Related U.S. Application Data

[62] Division of Ser. No. 859,501, Aug. 6, 1992, Pat. No. 5,272,172.

[30] Foreign Application Priority Data

Oct. 9, 1990 [JP] Japan .................................. 2-270707
Oct. 9, 1990 [JP] Japan .................................. 2-270708
Oct. 8, 1991 [WO] WIPO .................. PCT/JP91/01369

[51] Int. Cl.$^5$ ................. A61K 31/335; C07D 311/94
[52] U.S. Cl. ..................... 514/455; 549/386
[58] Field of Search ......................... 549/386; 514/455

[56] References Cited

U.S. PATENT DOCUMENTS 4,232,159 11/1980 Touyama et al. .................... 546/112

OTHER PUBLICATIONS

CA 70:20232a, *Chemical Abstracts*, vol. 70, No. 5, Feb. 3, 1969, p. 2017.
CA 102:163678r, *Chemical Abstracts*, vol. 102, No. 19, May 13, 1985, p. 352.
CA 95:7462x, *Chemical Abstracts*, vol. 95, No. 1, Jul. 6, 1981, p. 708.
CA 93:46836a, *Chemical Abstracts*, vol. 93, No. 5, Aug 4, 1980, p. 951.
CA 108:56474y, *Chemical Abstracts*, vol. 108, No. 7, Feb. 15, 1988, p. 766.
CA 101:207611z *Chemical Abstracts*, vol. 101, No. 23, Dec. 3, 1984, p. 354.
CA 93:186730m, *Chemical Abstracts*, vol. 93, No. 19, Nov. 10, 1989, p. 704.
CA 67:100249q, *Chemical Abstracts*, vol. 67, No. 21, Nov. 20, 1967, p. 9437.
CA 111:78420s, *Chemical Abstracts*, vol. 111, No. 9, Aug. 28, 1989, p. 786.
CA 106:49963n, *Chemical Abstracts*, vol. 106, No. 7, Feb. 16, 1987, p. 620.
Ca 92:215550q, *Chemical Abstracts*, vol. 92, No. 25, Jun. 23, 1980, p. 639.
CA 68:2487s, *Chemical Abstracts*, vol. 68, No. 1, Jan. 1, 1968, p. 223.
CA 97:178704y, *Chemical Abstracts*, vol. 97, No. 21, Nov. 22, 1982, p. 483.
CA 93:204864q, *Chemical Abstracts*, vol. 93, No. 21, Nov. 24, 1980, p. 710.
Isoe, et al., "Synthesis of Optically Active Petiodial and Determination of Its Absolute Structure," Tetrahedron Letters, vol. 29, No. 36, (1988), 4591–4594.
Isoe et al., "Novel Synthesis of (−)-Secologanin Aglucon-O-Silyl Ether from (+)-Genipin via Oxidative Fragmentation of γ-Hydroxyalkylstannane," Tetrahedron Letters, vol. 28, No. 47, (2987), 5865–8.

(List continued on next page.)

*Primary Examiner*—Johann Richter
*Assistant Examiner*—John Peabody
*Attorney, Agent, or Firm*—Burns, Doane, Swecker & Mathis

[57] ABSTRACT

Iridoid derivatives synthesized using genipin, which is an aglycon of geniposide, as the starting material are useful as an anti-hyperlipemia agent and as a cholagogue.

3 Claims, No Drawings

OTHER PUBLICATIONS

Fujikawa, et al., "Structure of Genipocyanin $G_1$, A Spontaneous Reaction Product Between Genipin and Glycerine," Tetrahedron Letters, vol. 28, No. 40, (1987), 4699–4700.

Guarnaccia, et al., "Geniposidic Acid, An Iridoid Glucoside From *Genipa Americana*," Tetrahedron Letters, (Dec. 1972) No. 50, 5125–7.

Oppolzer and Jacobsen, "Enantioselective Syntheses of (+)-α-Skytanthine, (+)-δ-Skytanthine and (+)-Iridomyrmecin by an Intramolecular Magnesium--Ene Reaction," Tetrahedron Letters, vol. 27, No. 10, (1986), pp. 1141–4.

Morizawa, et al., "Pd(O) Promoted Rearrangement of 2-(1,3-Butadienyl)Cyclopropane-1,1-Dicarboxylate Esters to 2-Alkenyl-3-Cyclopentene-1,1-Dicarboxylate Esters," Tetrahedron Letters, vol. 23, No. 28, (1982), 2871–4.

Bianco et al., "Mild Hydrogenolysis Process by Catalytic Transfer Hydrogenation," Tetrahedron Letters, vol. 30, No. 11, (1989), 1405–8.

Takeda et al., "Pharmacological Studies on Iridoid Compounds, II. Relationship between Structures and Choleretic Actions of Iridoid Compounds," *Journal of Pharmacobio Dynamics*, vol. 3, No. 10, Oct. 1980, pp. 485–492.

IRIDOID DERIVATIVES AND THE USE THEREOF AS A DRUG

This application is a divisional of application Ser. No. 07/859,501 filed Aug. 6, 1992 now U.S. Pat. No. 5,272,172.

TECHNICAL FIELD

This invention relates to iridoid derivatives having anti-hyperlipemia and cholagogue actions and pharmacologically useful.

BACKGROUND ART

The progress of the "aging society", has led to an increase in the number of patients suffering from hyperlipemia, as a geriatric diseases, and the development of an anti-hyperlipemia drug having a greater efficacy and safety is desired. Conventional efforts to develop such anti-hyperlipemia drugs have been concentrated on absorption inhibitors and synthetic inhibitors of cholesterol.

Cape Jasmim (*jasminoides Ellis*) is a crude drug from a Chinese recipe and has long been known to have pharmacological effects such as an anti-arteriosclerosis agent, blood coagulation inhibitor and cholagogue, and geniposide as a typical active component of Cape Jasmim has been confirmed to have excellent pharmacological activities.

In the field of anti-hyperlipemia, however, medicaments that have been developed conventionally cannot provide an entirely sufficient therapeutic effect. Therefore, the development of an anti-hyperlipemia having a different mechanism from the conventional medicaments is desired.

In the field of the cholagogue, on the other hand, genipin as the aglycon of geniposide is known as the cholagogue, and the development of iridoid derivatives having an excellent cholagogue action using this geniposide as the starting material is desired.

DISCLOSURE OF THE INVENTION

As a result of intensive studies into the problems described above, the inventors of the present invention found that the iridoid derivatives synthesized using genipin as the aglycon of geniposide, which is the principal component of Cape Jasmim, as the starting material have both anti-hyperlipemia and cholagogue actions, and thus completed the present invention.

The present invention provides novel compounds expressed by the following formulas 1 to 14, and their pharmacologically permissible salts. The present invention also provides an anti-hyperlipemia drug and a cholagogue containing the compounds expressed by the following formulas 1 to 18, and their phamacologically permissible salts, as an active principle.

Formula 1

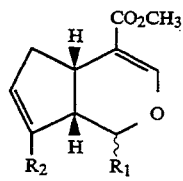

In the formula, $R_1$ is a benzoyloxyl group, a hydroxyl group, an acetoxyl group or an ethoxyethoxyl group, and $R_2$ is a benzoyloxymethyl group, a methoxymethyl group, a tert-butyl-dimethylsilyloxymethyl group, a carboxyl group or a hydroxymethyl group, with the proviso that those compounds of $R_1$ which represent a hydroxyl group and those of $R_2$ which represent a hydroxymethyl group are excluded.

Formula 2

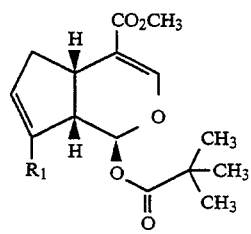

In the formula, $R_1$ is a methyl group or a trimethylacetyloxymethyl group.

Formula 3

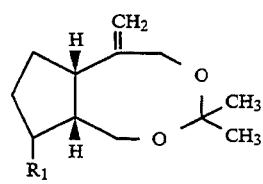

(3)

In the formula, $R_1$ is an α- or β-oriented methyl group.

Formula 4

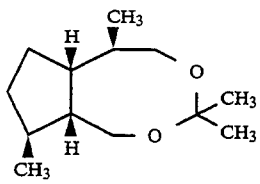

Formula 5

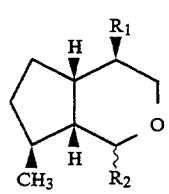

In the formula, $R_1$ is a methyl group or a methoxycarbonyl group, and $R_2$ is a hydroxyl group or an ethoxyethoxyl group, with the proviso that those compounds in which $R_1$ represents a methyl group and R2 represents a hydroxyl group are excluded.

Formula 6

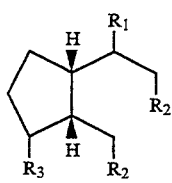

(6)

In the formula, $R_1$ is a hydroxymethyl group, a methyl group or a hydrogen atom, $R_2$ is a hydroxyl group or an acetoxyl group, and R3 is an α- or β-oriented methyl group, with the proviso that those compounds in which $R_1$ represents a hydrogen atom and $R_2$ represents a hydroxyl group, and those compounds in which $R_1$ represents a methyl group and $R_2$ represents a hydroxyl group are excluded.

Formula 7

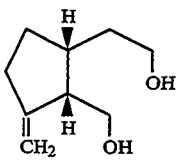

Formula 8

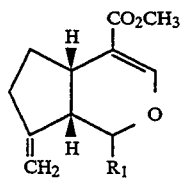

(8)

In the formula, $R_1$ is a hydroxyl group or an acetoxyl group.

Formula 9

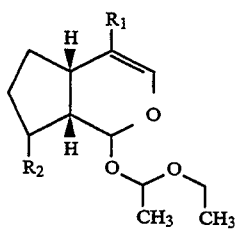

In the formula, $R_1$ is a methoxycarbonyl group, a methyl group, a hydroxymethyl group or an acetoxymethyl group, and $R_2$ is an α- or β-oriented methyl group.

Formula 10

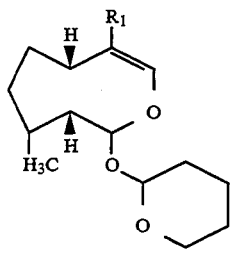

In the formula, $R_1$ is a methoxycarbonyl group or a hydroxymethyl group.

Formula 11

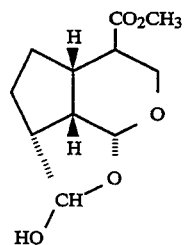

Formula 12

-continued

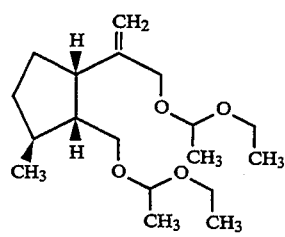

Formula 13

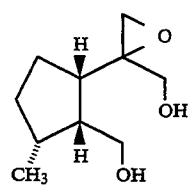

Formula 14

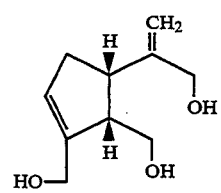

Formula 15

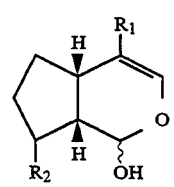

In the formula, $R_1$ is a methoxycarbonyl group or a methyl group, and $R_2$ is an α- or β-oriented methyl group.

Formula 16

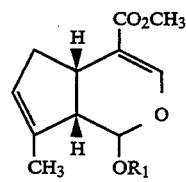

In the formula, $R_1$ is a hydrogen atom or a glucopyranosyl group.

Formula 17

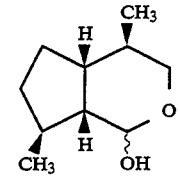

Formula 18

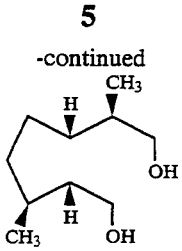

BEST MODE OF CARRYING OUT THE INVENTION

In addition to the compounds described above, the inventors of this invention have confirmed that the following compounds exhibit similar characteristics to those of the compounds described above, but as far as the experiments carried out at this time are concerned, the pharmacological effects of the following compounds seem slightly inferior.

methyl (4aS, 7aS)-1,4a, 5,7a-tetrahydro-7-methyl-1-oxocyclopenta[c]pyran-4-carboxylate, methyl (4aS, 7aS)-7-formyl-1,4a, 5,7a-tetrahydro-1-hydroxycyclopenta[c]pyran-4-carboxylate, (1S, 4aS, 7aS)-4,7-bis(hydroxymethyl)-1,4a,5,7a-tetrahydro-1-(2-tetrahydropyranyloxy)cyclopenta[c]pyran, methyl (4aS, 7aS)-1,4a, 5,7a-tetrahydro-7-(hydroxymethyl)-1-oxocyclopenta[c]pyran-4-carboxylate, (1S, 4aS, 7aS)-1-acetoxy-4,7-bis(hydroxymethyl)-1,4a,5,7a-tetrahydrocyclopenta[c]pyran, (1R, 2R, 3S)-2-(hydroxymethyl)-3-methyl-1-(2-propyl)-cyclopentane, 2-[(1S, 2R, 3S)-2-(hydroxymethyl)-3-methylcyclopent-1-yl]-2-propen-1-ol, 2-[(1S, 2R, 3R)-2-(hydroxymethyl)-3-methylcyclopent--1-yl]-2-propen-1-ol, 2-[(1R, 2R, 3S)-2-(hydroxymethyl)-3-methylcyclopent--1-yl]-ethan-1-ol, 2-[(1R, 2R, 3S)-2-(hydroxymethyl)-3-methylcyclopent--1-yl]-ethan-1-ol, methyl (4aS, 7aS)-6,7-epoxy-1, 4a, 5, 6, 7, 7a-hexahydro-1-hydroxy-7-(hydroxymethyl)-cyclopenta[c]pyran-4-carboxylate, methyl (1S, 4aS, 7aS)-1,7-diacetoxy-6,7-(epoxyrmethano)-1, 4a, 5, 6, 7, 7a-hexahydro-1- hydroxy-7-methytlyclopenta[c]pyran-4-carboxylate, methyl (4aS, 7aS)-6, 7-epoxy-1, 4a, 5, 6, 7, 7a-hexahydro-1-hydroxy-7-methylcyclopenta[c]pyran-4-carboxylate, methyl (1S, 4aS, 7aS)-1-[1-(ethoxy)ethoxy]-7-formyl1-,4a,5,7a-tetrahydrocyclopenta[c]pyran-4carboxylate, methyl (4aS, 7R, 7aR)-1,4a,5,6,7,7a-hexahydro-7-methyl-1-oxocyclopenta[c]pyran-4-carboxylate, methyl (1S, 4aS, 7aS)-1-[1-(ethoxy)ethoxy]-1, 4a, 5, 7a-tetrahydro-7-(hydroxymethyl)cyclopenta[c]pyran-1,4carboxylate, methyl (1S, 4aS, 7aS)-1-(2,3,4,6-tetra-O-acetyl-β-D-glucopyranosyloxy)-1,4a,5,7a-tetrahydro-7methylcyclopenta-[c]pyran-4-carboxylate, methyl (1S, 4aS, 7aS)-1,4a,5,7a-tetrahydro-7-methyl-1-(2,3,4,6-tetra-O-methyl-β-D-glucopyranosyloxy-cyclopenta[c]pyran-4-carboxylate, methyl (1S, 4aS, 7aS)-1-benzoyloxy-1,4a,5,7a-tetrahydro-7-methylcyclopenta[c]pyran-4-carboxylate, methyl (1S, 4aS, 7aS)-1-acetoxy-1,4a,5,7a-tetrahydro-7-methylcyclopenta[c]pyran-4-carboxylate, methyl (4aS, 7aR)-1,1,4a4,6,7,7a-heptahydro-7-methyl-cyclopenta[c]pyran-4-carboxylate, methyl (1S, 4aS, 7aS)-7-acetoxymethyl-1-(2,3,4,6-tetra-0-acetyl-β-D-glucopyranosyloxy)1,4a,5,7a-tetrahydrocyclopenta[c]pyran-4-carboxylate, methyl (1S, 4aS, 7S, 7aR)-1-(2,3,4,6-tetra-0-acetyl-β-D-glycopyranosyloxy)-1, 4a, 5, 6, 7, 7a-hexahydro-7-methylcyclopenta[c]pyran-4-carboxylate, methyl (1S, 4aS, 7S, 7aS)-7-(acetoxymethyl)-1-(2,3,4,6-tetra-0-acetyl-β-D-glucopyranosyloxy)-1, 4a,5,7a-hexahydrocyclopenta[c]pyran-4-carboxylate, methyl (1S, 4aS, 7aS)-1-(2,3,4,6-tetra-0-acetyl-β-D-glucopyranosyloxy)-1,4a,4,6,7,7a-hexahydro-7-methylenecyclopenta[c]pyran-4-carboxylate, methyl (1S, 4aS, 7R, 7aS)-1, 7-(epoxymethane)-1, 4a,5,6,7,7a-hexahydrocyclopenta[c]pyran-4-carboxylate, methyl (1S, 4aS, 7aS)-1-(tert-butyl-dimethylsilyloxy)-1,4a,5,7a-tetrahydro-7-(hydroxmethyl)cyclopenta[c]pyran-4-carboxylate, methyl (1S, 4aS, 7aS)-1-(tert-butyl-dimethylsilyloxy)-7-formyl-1,4a,5,7a-tetrahydrocyclopenta[c]pyran-4-carboxylate, methyl (4aS, 7aS)-7-[(tert-butyldimethylsilyloxy)methyl]-1,4a,5,7a-tetrahydro-1-hydroxycyclopenta[c]pyran-4-carboxylate, methyl (1S, 4aS, 7aS)-1,4a,5,7a-tetrahydro-1-(2-tetrahydropyranyloxy)-7-(hydroxymethyl)cyclopenta[c]pyran-4-carboxylate, methyl (4aS, 7aS)-7-[(tert-butyldimethylsilyloxy)methyl]-1,4a,5,7a-tetrahydro-1-oxocyclopenta[c]pyran-4-carboxylate, methyl (4aS, 7aS)-7-[(tertbutyldiphenylsilyloxy)methyl]-1,4a,5,7a-tetrahydro-1-hydroxycyclopenta[c]pyran-4carboxylate, methyl (1S, 4aS, 7aS)-7-[(tertbutyldiphenylsilyloxy)methyl]-1,4a,5,7a-tetrahydro-1-(2-tetrahydropyranyloxy)cyclopenta[c]pyran-4-carboxylate, (1S, 4aS, 7aS)-1-acetoxy-7-[(tert-butyldiphenylsilyloxy)methyl]-1,4a,5,7a-tetrahydrocyclopenta [c]-4-carbaldehyde, methyl (4aS, 7aS)-7-[(tert-butyldiphenylsilyloxy)methyl]-1,4a,5,7a-tetrahydro-1-oxocyclopenta[c]pyran-4-carboxylate, (1S, 4aS, 7aS)-1,4a,5,7a-tetrahydro-1-(tetrahydro-2-pyranyloxy)-7-[(2-tetrahydropyranloxy)methyl]-4-(hydroxymethyl)cyclopenta[c]pyran, (1S, 4aS, 7aS)-1-[(tert-butyldimethylsilyloxy)-7-[(tert-butyldimethylsilyloxy)methyl]-1,4a,5,7a -tetrahydro-4-(hydroxymethyl)cyclopenta[c]pyran, methyl (4aS, 7S, 7aS)-7-[(tert-butyldiphenylsilyloxy)-methyl]-1,4a,5,6,7,7a-hexahydro-1-hydroxycyclopenta[c]pyran-4-carboxylate, methyl (4aS, 7S, 7aS)-7-[(tert-butyldiphenylsilyloxy)-methyl]-1,4a,5,6,7,7a-hexahydro-1-oxocyclopenta[c]pyran-4-carboxylate, methyl (4aS, 7S, 7aS)-7-[(tert-butyldimethylsilyloxy)-methyl]-1,4a,5,6,7,7a-hexahydro-1-hydroxycyclopenta[c]pyran-4-carboxylate, methyl (4aS, 7S, 7aS)-7-[(tert-butyldimethylsilyloxy)-methyl]-1,4a,5,6,7,7a-hexahydro-1-oxocyclopenta[c]pyran-4-carboxylate, methyl (1S, 4aS, 7R, 7aR)-1-acetoxy-7-methyl-1, 4a, 5, 6, 7, 7a-hexahydrocyclopenta[c]pyran-4-carboxylate, (4S, 4aS, 7S, 7aR)-1, 1, 4, 4a, 5, 6, 7, 7a-octahydro-4, 7-dimethylcyclopenta[c]pyran-3-one, (4aS, 7S, 7aR)-1, 1,4a,5,6,7,7a-octahydro-7-methyl-4-methylenecyclopenta[c]pyran-3-one, methyl (1S, 4aS, 7S, 7aR)-1-(β-D-glucopyranosyloxy)-1,4a,5,6,7,7a-hexahydro-7methylcyclopenta[c]pyran-4-carboxylate.

Hereinafter, the compounds described in the present invention will be referred to simply as the "iridoid compounds".

The iridoid compounds can be obtained by the use of geniposide or genipin contained in Cape Jasmim as the starting material, and selecting and combining suitably desired reactions such as acetylation, deacetylation, methylation, hydrolysis, oxidation, reduction, introduction of a protective group, and so forth, in accordance with the intended substance(s) to be obtained.

A geniposide commercially available on the market can be used as the starting material, and genipin can be derived from this compound by removing the geniposide sugar.

Preparation examples of the genipin are as follows.

PREPARATION EXAMPLE 1

First, 100 g of geniposide was dissolved in 650 ml of water. After 115 g of sodium periodate was added to the solution, the reaction mixture was stirred at room temperature for two hours. After 41 g of sodium boron hydride was further added, the reaction mixture was further stirred at room temperature for two hours. Subsequently, a 6N aqueous hydrochloric acid solution and ether were added, the reaction mixture was stirred at room temperature for four hours. After the addition of sodium hydrogen sulfite and sodium chloride, the reaction mixture was stirred to thereby separate an ether layer. After the ether layer was separated and dried, ether was distilled off, and a yellow solid was obtained. The solid was further recrystallized from methanol and ether to yield 43 g of genipin.

The details of the various reactions described above are as follows.

(1) Any method can be used for acetylation as long as it is an ordinary acetylation method. Examples of the acetylating reagents are acetic anhydride, acetyl chloride, etc., and they are used in combination with tertiary amines such as triethylamine, diisopropylethylamine, pyridine, lutidine, collidine, diazabicycloundecene, 4-dimethylaminopyridine, etc.

Any solvents can be used as long as they do not have portions which per se are not acetylated. In consideration of solubility of the reaction products and the starting materials, however, organic halides such as chloroform, dichloromethane, etc., ethers such as ether, tetrahydrofuran, etc., and aromatic hydrocarbons such as benzene, toluene, etc., are preferred. The reaction is carried out at a temperature of from 0° C. to room temperature for at least one hour.

(2) Deacetylation is carried out at near room temperature for at least three hours using a catalytic amount (1 to 5 wt% of the starting material to be deacetylated) of a carbonate such as potassium carbonate, sodium carbonate, etc., and an alcohol such as methanol, ethanol, etc., as the solvent.

(3) Methylation can be accomplished by carrying out the reaction at a temperature of from −20° to room temperature for at least two hours using a methyl iodide, dimethyl sulfate, etc., as a methylating reagent, and potassium hydride, sodium hydride, lithium diisopropylamide, sodium hexamethyldisilazide, etc., as a base, inside a solvent such as tetrahydrofuran, dimethyl sulfoxide, etc.

(4) Any hydrolysis methods can be used for the hydrolysis as long as they are ordinary acid hydrolysis methods. Examples of the acids that can be used are hydrochloric acid, sulfuric acid, pyridinium para-toluenesulfonate, acetic acid, boron trifluoride-ether complex, hydrofluoric acid, and so forth. The hydrolysis is carried out inside water or an organic solvent containing water at 0° C. to 100° C. for at least 30 minutes.

(5) The oxidative reaction is used properly in accordance with the structure of a functional group to be oxidized. First, an oxidation cleavage of vicinal glycol is effected by carrying out the reaction in water or in an alcohol such as methanol, ethanol, etc., using an oxidizing agent of a periodate type (such as sodium periodate, potassium periodate, O-periodic acid, etc.) at 0° C. to room temperature for at least 30 minutes.

Next, the oxidation of the hydroxyl group to a carbonyl group is effected by carrying out the reaction using manganese dioxide, pyridinium chlorochromate, pyridinium dichromate, chromium trioxide, etc., as a reagent, and an aromatic hydrocarbon such as benzene, toluene, etc., or an organic halide such as chloroform, dichloromethane, etc., as the solvent, at a temperature near room temperature for at least 30 minutes. The oxidation of the double bond is effected by using a system comprising the combination of a peroxyacid such as metha-chloroperbenzoic acid, magnesium monoperoxyphthalate, peracetic acid, etc., or an organic peroxide such as cumen hydroperoxide, t-butyl hydroperoxide, etc., with a catalyst such as vanadyl acetylacetonate, tungstic acid, molybdenum hexacarbonyl, etc. In this case, an organic halide such as chloroform, dichloromethane, etc., or an aromatic hydrocarbon such as benzene, toluene, etc., is used as the solvent, and the reaction is carried out at 0° C.–70° C. for at least 10 minutes.

(6) The reduction can be accomplished by a method using palladium chloride, platinum dioxide, palladium, palladium hydroxide, rhodium, bis(triphenylphosphine)palladium dichloride, etc., as a catalyst, and hydrogen, cyclohexadiene, ammonium formate, hydrazine, etc., as a reducing agent, and carrying out the reaction at 0° C. to 100° C. for at least 5 hours in a general organic solvent such as ethyl acetate, benzene, toluene, methanol, tetrahydrofuran, dioxane, etc., or by a method which reacts sodium boron hydride, sodium cyanoboron hydride or tetra-n-butylammonium boron hydride in water or an alcohol such as methanol, ethanol or isopropanol, at a temperature above 0° C. for at least 10 minutes, or by a method which reacts a hydrogenated aluminum compound such as lithium aluminum hydride, diisobutylaluaninum hydride, sodium bis(methoxyethoxy)aluminum hydride, etc., in an ether type solvent such as ether, tetrahydrofuran, dimethoxyethane, etc. or a hydrocarbon solvent such as benzene, toluene, etc., at −80° C. to room temperature for at least 10 minutes. These methods can be selected and employed appropriately.

(7) A silyl type protective group such as t-butyl-dimethylsilyl group, t-butyldiphenylsilyl group, etc., an acetal type protective group such as an ethoxyethyl group or a tetrahydropyranyl group, or an acyl type protective group such as an acetyl group or a benzoyl group, can be used as the protective group.

The silyl type protective group can be introduced by carrying out the reaction using an ordinary silylation agent such as t-butyldimethylsilyl chloride, t-butyldiphenylsilyl chloride, t-butyldimethylsilyl triflate, etc., as a reagent, in an organic solvent such as chloroform, dichloromethane, dimethylformamide or benzene, at −30° C. to room temperature for at least 5 minutes in the presence of triethylamine, imidazole, 4-dimethylaminopyridine, lutidine or silver nitrate.

The acetal type protective group can be introduced by carrying out the reaction using ethyl vinyl ether, dihydropyran, etc., as a reagent, and pyridinium paratoluenesulfonate, para-toluenesulfonic acid, camphor sulfonic acid or sulfuric acid as the catalyst, inside an ordinary organic solvent which per se does not react with the reagent, at 0° C. to room temperature for at least 30 minutes.

The acyl type protective group can be introduced by carrying out the reaction by the use of acetyl chloride, acetic anhydride, benzoyl chloride, benzoic anhydride, etc., as the reagent, in accordance with the acetylation method described already.

Next, the anti-hyperlipemia action of the iridoid compounds will be explained with reference to Experimental Examples. The numbers put to test compounds in Table tabulating the experimental results represent the compounds corresponding to the respective Examples or Definite Examples.

EXPERIMENTAL EXAMPLE 1

Method of Experiment

Male Wistar rats 6.5 weeks old were allowed to freely intake a high fat food (containing 1% of cholesterol, 0.5% of sodium cholate, 12% of beef tallow and 20% of standard chow) in the source of two weeks, to thus cause an outbreak of hyperlipemia. The dose of the drug was started simultaneously with the application of the high fat food, and was perorally given once a day through a stomach tube until the end of the experiment. The drugs were all suspended in a cane sugar fatty acid ester and were administered. The oily compounds were adjusted in advance to 100 mg/ml by diethyl ether. A suitable amount was collected at the time of the dose and after diethyl ether was evaporated and removed, it was suspended in a cane sugar fatty acid ester (1% ryoto sugar ester) and then given. After the final dose of the drug, the rats were fasted for about 18 hours, and the blood was sampled to measure the blood serum lipid. The blood serum lipid was measured by using a TBA-380 biochemical analyzer (a product of Toshiba Medical Co.,) unless a particular hindrance occurred.

The results are tabulated in Table 1.

TABLE 1

| Test drug (dose) | Blood serum cholesterol (%) | Blood serum triglyceride (%) |
|---|---|---|
| Control | 100 | 100 |
| Definite Example 4 (10 mg/kg) | 73.3 | 86.0 |
| Definite Example 4 (30 mg/kg) | 75.4 | 91.0 |
| Definite Example 6 (10 mg/kg) | 79.6 | 86.7 |
| Definite Example 6 (30 mg/kg) | 85.4 | 80.4 |
| Definite Example 7 (10 mg/kg) | 94.4 | 96.9 |
| Definite Example 7 (30 mg/kg) | 105 | 64.6 |
| Definite Example 8 (10 mg/kg) | 94.4 | 82.5 |
| Definite Example 8 (30 mg/kg) | 54.8 | 68.7 |
| Definite Example 9 (10 mg/kg) | 93.6 | 74.5 |

TABLE 1-continued

| Test drug (dose) | Blood serum cholesterol (%) | Blood serum triglyceride (%) |
|---|---|---|
| Definite Example 9 (30 mg/kg) | 59.3 | 60.0 |
| Definite Example 31 (10 mg/kg) | 82.0 | 79.0 |
| Definite Example 31 (30 mg/kg) | 96.1 | 76.5 |

EXPERIMENTAL EXAMPLE 2

Method of Experiment

Liver slices (0.5 mm) were prepared from male Wistar rats 5 weeks old acclimated for 10 days in a bright-/dark inversion raising chamber (bright period: 8:00 p.m.–8:00 a.m.). Each slice was placed into a sealed plug test tube containing 0.5 $\mu$Ci [$1^{14}$C] acetic acid (2–3 mCi/mmol) and 0.5% BSA suspension and a KrebsRinger's solution so adjusted that the drug had a final concentration of 0.1–1.0 mM. Incubation was carried out at 37° C. for 120 minutes in 95% oxygen and 5% carbon dioxide. The reaction was stopped by adding 1 ml of 15% potassium hydroxide/ethanol, and saponification was carried out at 80° C. for 2 hours. The sterol fraction was extracted by petroleum ether and was evaporated to driness. Thereafter, 1 ml of acetone/ethanol (1:1) and 1 ml of 0.5% digitonine were added, and the mixture was left standing for a night at room temperature. The precipitate was collected by centrifugal separation and was washed with 2 ml of acetone/ether (1:1). The precipitate was further centrifuged. After the supernatant was discarded, the precipitate was dissolved in methanol and its radioactivity was measured.

The results are tabulated in Table 2.

TABLE 2

| Kind of test drug | Relative amount of synthesized cholesterol (%) |
|---|---|
| Control | 100 |
| Definite Example 22 | 86.2 |
| Definite Example 23 | 80.1 |
| Definite Example 27 | 73.5 |
| Definite Example 30 | 50.1 |
| Definite Example 32 | 96.2 |
| Definite Example 38 | 72.8 |
| Definite Example 36 | 72.4 |

EXPERIMENTAL EXAMPLE 3

Method of Experiment

Influences on synthetic activity of bilic acid in incubated liver cell

The liver cells were separated from male Wistar rats 5.0–5.5 weeks old using a reflux method in accordance with the method of Nakamura et al (Toshikazu Nakamura "The Experimental Method for the Primary Cultured Hepatocytes", 1987). In this case, the separation of the cells was started at 9–10:00 a.m. The separated liver cells were floated in a Williams E medium inactivated by heat-treatment and containing 10% FBS, 20 mU/ml insulin, 50 mM dexamethasone, 100 IU/ml peniciline and 100 $\mu$g/ml streptomycin so that the cell density became $1 \times 10^5$ cells/cm$^2$/0.2 ml. The liver cells were planted in a cell density of $1 \times 10^5$ cells/cm$^2$/0.2 ml in a dish having a diameter of 60 mm. After incubation at 37° C. for 4 hours, a medium exchange was made and the medium was changed to 3 ml. Next, [4$^{14}$C] cholesterol was added in an amount of 11.655 kBq per dish, and a 0.33% ethanol solution of each test drug was added. Control used only 0.33% ethanol. After incubation was carried out at 37° C. for 24 hours, the synthetic activity of cholic acid and chenodeoxycholic acid generated in the cells and the medium were measured.

Measurement of cholic and chenodeoxycholic acid synthetic activity

The measurement of cholic acid and chenodeoxycholic acid synthetic activity was carried out in accordance with the method of M. G. Pricen et al (Hans M. G. Pricen, Chrisstine M. G. Hujismans, Folkert Kuipers, Roel J. Vonk and Herman Jan M. Kempen, J. Clin. Invest., 78: 1064–1071, 1986). Twenty-four hours later, the cells and the medium were collected from the incubated liver cells and the cells were pulverized by a ultrasonic pulverizer. Bile acid was separated and eluted by a column cartridge having an opposite phase system, i.e., "Sep-pak" ® C$_{18}$ (Waters Associates, Milford, Mass.), and the conjugation of conjugated bile acid was hydrolyzed using choloylglycine hydrolase. The extraction of bile acid was carried out using chloroform after the solution was rendered acidic by hydrochloric acid. The extract was dissolved in 100 μl of water:methanol (1:4, containing 40 μg/10 μl cholic acid and 100 μg/100 μl chenodeoxycholic acid). 80 μl of this solution was spotted onto an aluminum plate (MERCK, ART 5582) and was developed using a developing solution consisting of benzene/1,4-dioxane/acetic acid (20:10:2). After the TLC plate was exposed to an iodine gas stream and each spot of bile acid was confirmed, it was cut off and its radioactivity was measured by a liquid scintillation counter. To correct the proportion of elution of the Sep-pak and the hydroclysis and extraction of conjugated bile acid by choloylglycine hydrolase, 2 nCi of [$^3$H(G)]taurocholic acid was added and 3H of the spot of cholic acid was measured after the supersonic pulverization and correction was thus carried out (Tsujita, Y., Kuroda, M., Shimada, Y., Tanzawa, K., Arai, M., Kenko, I., Tanaka, M., Tarumi, C., Watanabe, Y., and Fujii, Biochemical et Biophysics Acta. 877: 50–60, 1986).

Non-radioactive cholic acid and chenodeoxycholic acid were added as a carrier, to clarify the position of the spot by the iodine gas stream when bile acid was developed, but for the β-muricholic acid, the position of the spot was indefinite even when the non-radioactive acids were added. Therefore, the portion estimated by the Rf value described in the reference was cut off and measured again.

The kind of the test drugs and the concentration, and the results of the experiment, are shown in Tables 3 and 4.

TABLE 3

| Kind of test drug | Concentration | Relative amount of synthesized chenodeoxycholic acid | Relative amount of synthesized cholic acid |
|---|---|---|---|
| Control | 0.33% ethanol alone | 100 | 100 |
| Definite Example 45 | 10$^{-8}$M | 112 | 108 |
| Definite Example 45 | 10$^{-7}$M | 119 | 121 |
| Definite Example 45 | 10$^{-6}$M | 152 | 146 |

TABLE 4

| Kind of test drug | Concentration | Relative amount of synthesized chenodeoxycholic acid | Relative amount of synthesized cholic acid |
|---|---|---|---|
| Control | 0.33% ethanol alone | 100 | 100 |
| Definite Example 31 | 10$^{-6}$M | 113 | 105 |
| Definite Example 43 | 10$^{-6}$M | 105 | 109 |
| Definite Example 44 | 10$^{-6}$M | 155 | 130 |

From the results of the experiments, the significant increase of the cholic acid and chenodeoxycholic acid synthetic activity was recognized in the test drug addition group, and the afore-mentioned iridoid compounds were demonstrated as being effective as a hyperlipemia drug.

EXPERIMENTAL EXAMPLE 4

Method of Experiment

Male Wistar rats 6.5 weeks old were allowed to freely intake a high fat food (0.5% cholesterol, 1.0% cholic acid, 20.0% casein, 50.5% cane sugar, 12.0% hardened coconut oil, 4.0% cellulose, 4.0% mineral mixture, 0.5% vitamine mixture, 7.5% white fish meal) in the course of two weeks so as to cause the outbreak of hyperlipemia. The dose of the drug was started simultaneously with the application of the high fat food, and was perorally given once a day through a stomach tube until the end of the experiment. The drugs were all suspended in a cane sugar fatty acid ester and were administered. The oily compounds were adjusted in advance to 100 mg/ml by diethyl ether. A suitable amount was collected at the time of the dose and after diethyl ether was evaporated and removed, it was suspended in a cane sugar fatty acid ester (1% ryoto sugar ester) and was then given. After the final dose of the drug, the rats were fasted for about 18 hours, and the blood was sampled to measure the blood serum lipid. The blood serum lipid was measured by using a TBA-380 bio-chemical analyzer (a product of Toshiba Medical Co.,) unless a particular hindrance occurred. The results are tabulated in Table 5.

TABLE 5

| Test drug (dose) | Blood serum cholesterol (%) |
|---|---|
| Control | 100 |
| Definite Example 9 (10 mg/kg) | 70.8 |
| Definite Example 9 (30 mg/kg) | 62.8 |
| Definite Example 4 (10 mg/kg) | 85.3 |
| Definite Example 4 (30 mg/kg) | 75.0 |

Next, the cholagogic action of the iridoid compounds will be explained with reference to Experimental Examples.

EXPERIMENTAL EXAMPLE 5

Method of experiment:

After male Wistar rats 7 weeks old were fasted for 24 hours, they were anesthetized by the interperitoneal administration of 1.25 g/kg (volume 2 ml/kg) of urethane. A polyethylene cannula (SP-10, a product of Natsume Seisakusho) was inserted into a bile duct and after the bile was caused to flow out for 30 minutes, the bile was collected in the course of 1 hour. Thereafter, each test drug was suspended or dissolved in a 1% aqueous Tween-80 solution, and was administered into the duodenum at a rate of 5 ml/kg. Furthermore, the bile was collected every hour in the course of five hours, and its weight was measured. Only a 1% Tween-80 solution was given as a control.

The results are tabulated in Tables 6, 7, 8, 9 and 10, wherein the bile secretion amount every hour was represented by a percentage with the bile secretion amount (mg) one hour before the dose of the test drug being 100.

TABLE 6

| Kind of test drug | Time after dose (hour) | | | | |
|---|---|---|---|---|---|
| | 0–1 | 1–2 | 2–3 | 3–4 | 4–5 |
| Control | 82.9 | 74.1 | 66.1 | 59.8 | 53.3 |
| Definite Example 4 | 146.9 | 97.8 | 85.4 | 77.2 | 71.8 |
| Definite Example 43 | 156.2 | 95.2 | 76.1 | 65.7 | 58.3 |
| Definite Example 44 | 137.2 | 95.0 | 78.4 | 66.5 | 59.8 |
| Definite Example 45 | 163.8 | 99.7 | 78.6 | 67.8 | 59.1 |

TABLE 7

| Kind of test drug | Time after dose (hour) | | | | |
|---|---|---|---|---|---|
| | 0–1 | 1–2 | 2–3 | 3–4 | 4–5 |
| Control | 87.7 | 75.3 | 65.0 | 58.7 | 51.8 |
| Definite Example 35 | 110.4 | 85.2 | 71.4 | 61.1 | 53.5 |
| Definite Example 45 | 163.4 | 99.6 | 75.2 | 61.7 | 53.3 |

TABLE 8

| Kind of test drug | Time after dose (hour) | | | | |
|---|---|---|---|---|---|
| | 0–1 | 1–2 | 2–3 | 3–4 | 4–5 |
| Control | 84.1 | 72.5 | 63.8 | 56.7 | 51.2 |
| Definite Example 4 | 150.8 | 93.7 | 74.0 | 63.9 | 57.2 |
| Definite Example 4 | 111.4 | 78.0 | 66.7 | 55.2 | 50.3 |
| Definite Example 9 | 134.5 | 90.9 | 76.5 | 66.7 | 59.4 |
| Definite Example 31 | 126.7 | 88.0 | 73.0 | 63.7 | 55.1 |

TABLE 9

| Kind of test drug | Time after dose (hour) | | | | |
|---|---|---|---|---|---|
| | 0–1 | 1–2 | 2–3 | 3–4 | 4–5 |
| Control | 81.1 | 66.6 | 55.8 | 49.0 | 42.8 |
| Definite Example 5 | 105.0 | 78.0 | 62.0 | 52.6 | 45.1 |
| Definite Example 8 | 85.0 | 71.7 | 60.1 | 50.6 | 44.4 |
| Definite Example 18 | 91.3 | 74.6 | 60.3 | 51.1 | 44.1 |
| Definite Example 20 | 82.6 | 66.8 | 55.1 | 48.6 | 42.8 |

TABLE 10

| Kind of test drug | Time after dose (hour) | | | | |
|---|---|---|---|---|---|
| | 0–1 | 1–2 | 2–3 | 3–4 | 4–5 |
| Control | 82.9 | 74.1 | 66.1 | 59.8 | 53.3 |
| Definite Example 17 | 115.7 | 77.3 | 62.9 | 54.0 | 47.2 |
| Definite Example 27 | 98.3 | 75.3 | 59.0 | 48.7 | 43.5 |
| Definite Example 30 | 97.9 | 83.1 | 69.7 | 61.0 | 53.9 |
| Definite Example 32 | 110.7 | 80.6 | 66.2 | 55.6 | 49.6 |

The results given above demonstrate that the increase in the bile secretion amount was recognized in each test drug addition group, and that the compounds expressed by the afore-mentioned formulas were useful as the cholagogue.

Next, low toxicity and high safety of the iridoid compounds will be illustrated by the result of acute toxicity test.

The acute toxicity test was carried out by abdominally and administering each test drug to male S.P.P. mice and determining an LD$_{50}$ value.

The results are tabulated in Table 11.

TABLE 11

| Test Drug | LD$_{50}$ (mg/kg) |
|---|---|
| Definite Example 6 | 406 |
| Definite Example 7 | 382 |
| Definite Example 9 | 407 |
| Definite Example 12 | 527 |
| Definite Example 16 | 412 |
| Definite Example 18 | 559 |
| Definite Example 19 | 355 |
| Definite Example 27 | 473 |
| Definite Example 28 | 406 |
| Definite Example 30 | 468 |
| Definite Example 31 | 814 |
| Definite Example 34 | 511 |
| Definite Example 45 | 406 |
| Definite Example 43 | 231 |
| Definite Example 44 | 389 |

The results of the acute toxicity test given above demonstrate that the iridoid compounds had a low toxicity and high safety.

Next, Examples for the preparation of the iridoid compounds will be given. The compounds of these Examples are recognized as novel compounds.

EXAMPLE 1

(2R)-2-[(1R, 2R, 3S)-2-(hydroxymethyl)-3-methylcyclopent-1-yl]propan-1-ol (100 mg, 0.00058 mol) (obtained in Definite Example 45) was dissolved in 5 ml of dichloromethane, and 2 ml of 2,2-dimethoxypropan and 5 mg of p-toluenesulfonic acid were added. After being stirred at room temperature for 12 hours, the reaction mixture was poured into 50 ml of ethyl acetate. After the organic layer was washed with an aqueous mixed solution of aqueous sodium bicarbonate (10 ml) and saturated sodium chloride solution (20 ml), it was dried by magnesium sulfate, filtered, and then concentrated under a reduced pressure. The residual substance was purified by a chromatography using silica gel. When the solvent of the fraction obtained from hexane:ether=8:2 eluent was distilled off, a colorless oily substance, i.e., (1R, 7R, 8S, 11S)-4,4,7,11-tetramethyl-3,5-dioxabicyclo[6.3.0]undecane (10 mg, yield=7.9%). This (1R, 7R, 8S, 11S)-4,4,7,11-tetramethyl-3,5dioxabicyclo[6.3.0]undecane had the following physicochemical properties:

Proton nuclear magnetic resonance (NMR) spectrum (δ ppm in CDCl$_3$): 0.76 (3H, s), 0.99 (3H, s), 1.36 (3H, s), 1.41 (3H, s), 0.80–1.88 (2H, m), 3.20 (1H, t, J=12 Hz), 3.41 (1H, t, J=12 Hz), 3.64 (1H, dd, J=5, 11 Hz), 3.75 (1H, dd, J=8, 11 Hz) Infrared (IR) absorption spectrum υ neat max cm$^{-1}$: 2950, 2862, 1438, 1207, 1060

EXAMPLE 2

(2R)-2-[(1R, 2R, 3S)-2-(hydroxymethyl)-3-methylcyclopent-1-yl]propan-1-ol (100 mg, 0.00058 mol) obtained in Definite Example 45 was dissolved in 5 ml of dichloromethane, and after 0.3 ml of pyridine and 0.27 ml (0.0029 mol) of acetic anhydride were added, 5 mg of N,N-dimethylaminopyridine was further added. The reaction mixture was stirred at room temperature for three hours and was then poured into 50 ml of ethyl acetate. The organic layer was washed by 2N aqueous hydrochloric acid solution, 20 ml of saturated sodium bicarbonate solution and 20 ml of saturated sodium chloride solution. The organic layer was then dried by magnesium sulfate, filtrated, and then concentrated under a reduced pressure. The residual substance was purified by a chromatography using silica gel, and the solvent of the fraction obtained from hexane:ether=1:1 eluent was distilled off. As a result, a colorless oily substance was obtained, i.e., (2R)-2-[(1R, 2R, 3S)-2-(acetoxymethyl)-3-methylcyclopent-1-yl]-1-propylacetate (127 mg, yield=85.2%). This (2R)-2-[(1R, 2R, 3S)-2-(acetoxymethyl)-3-methylcyclopent-1-yl]-1-propyleacetate had the following physicochemical properties:

Proton NMR spectrum (δ ppm in CDCl$_3$): 0.95 (3H, d, J=7 Hz), 0.99 (3H, d, J=7 Hz), 1.00–2.12 (7H, m), 2.04 (3H, s), 2.06 (3H, s), 3.72–3.92 (2H, m), 4.04–4.18 (2H, m)

EXAMPLE 3

Methyl (4aS, 7aS)-7-formyl-1,4a,5,7a-tetrahydro-1-hydroxycyclopenta[c]pyran-4-carboxylate (100 mg, 0.00042 mol) obtained in Definite Example 23 was dissolved in 5 ml of ethyl acetate, and after 5% Rh-Al$_2$O$_3$ (5 mg) was suspended, the reaction mixture was stirred for 12 hours in a hydrogen gas atmosphere of 1 atm. After the catalyst was filtered by celite, concentration was carried out. The residual substance was purified by chromatography using silica gel, the solvent of the fraction obtained from hexane:ether=1:1 eluent was distilled off, and a colorless oily substance was obtained, i.e., methyl (1R, 4aR, 7S, 7aS)-1,7-epoxymethano-1,4a,5,6,7,7a-hexahydro-7hydroxycyclopenta[c]pyran-4-carboxylate (57 mg, yield=56.5%). This methyl (1R, 4aR, 7S, 7aS)-1, 7-epoxymethano-1,4a,5,6,7,7a-hexahydro-7-hydroxycyclopenta[c]pyran-4-carboxylate had the following physicochemical properties:

Proton NMR spectrum (δ ppm in CDCl$_3$): 1.02–1.26 (1H, m), 1.60–1.92 (2H, m), 2.18–2.32 (1H, m), 2.60–2.92 (3H, m), 3.74 (3H, s), 5.10 (1H, brs), 5.88 (1H, d, J=6 Hz), 7.51 (1H, s)

IR absorption spectrum υ neat max cm$^{-1}$: 3592, 2948, 1704, 1646, 1438, 1390, 1294, 1172, 1138, 1102, 1074, 992, 956, 908, 772

EXAMPLE 4

Methyl (4aS, 7S, 7aR)-1-hydroxy-7-methyl-1,4a,5,6,7,7a-hexahydrocyclopenta[c]pyran-4carboxylate (25.0 g, 0.117 mol) obtained in Definite Example 4 was dissolved in 400 ml of dichloromethane, and 110 ml (1.17 mol) of ethyl vinyl ether and 130 mg of pyridinium p-toluenesulfonate were added. The reaction mixture was stirred at room temperature. Twenty-four hours later, 500 ml of dichloromethane was added to the reaction mixture, and washing was carried out by a mixed aqueous solution of saturated sodium bicarbonate solution and 200 ml of saturated sodium chloride solution. The organic layer was dried by magnesium sulfate, filtered, and then concentrated under a reduced pressure. The residual substance was purified by chromatography using silica gel and the fraction obtained from hexane:ether=1:1 eluent was concentrated. A pale yellow oily substance was thus obtained, i.e., methyl (1S, 4aS, 7S, 7aR)-1-[1-(ethoxy)ethoxy]-7-methyl-1,4a,5,6,7,7a-hexahydropenta[c]pyran-4-carboxylate (30.5 g, yield=91.2%). This methyl (1S, 4aS, 7S, 7aR-)1-[1-(ethoxy)ethoxy]-7-methyl-1,4a,5,6,7,7a-hexahydrocyclo-penta[c]pyran-4-carboxylate had the following physicochemical properties:

ProtOn NMR spectrum (δ ppm in CDCl$_3$): 1.14 (3H, d, J=4 Hz), 1.21 (3H, t, J=7 Hz) 1.36 (3H, d, J=3 HZ), 1.60–2.36 (2.36H, m), 2.88 (1H, d, J=8 Hz), 3.50–3.80 (2H, m), 3.71 (3H, s), 4.80 (0.5H, d, J=6 Hz), 4.91 (1H, d, J=6 Hz), 5.01 (0.5H, d, J=5 Hz), 7.41 (1H, brs) IR absorption spectrum υ neat max cm$^{-1}$: 2952, 1704, 1632, 1438, 1382, 1284, 1098, 958, 870 Mass spectrum m/z (%): 285 (M+H)$^+$

EXAMPLE 5

Methyl (1S, 4aS, 7S, 7aR)-1-[1-(ethoxy)ethoxy]-7-methyl-1,4a,5,6,7,7a-hexahydrocyclopenta[c]pyran-4carboxylate (15.0 g, 0.053 mol) obtained in Example 4 was dissolved in 250 ml of anhydrous tetrahydrofuran, and the reaction mixture was cooled to −50° C., 88 ml of diisobutylaluminum hydride (1.5 mol toluene solution) was added dropwise to this solution. After the reaction mixture was stirred at the same temperature for 3 hours, 10 ml of acetone was added and the solution was further stirred for 20 minutes. Furthermore, a 3% aqueous sodium hydroxide solution was added dropwise and the solution was stirred for 1 hour. After magnesium sulfate was added, the reaction solution was stirred further for 20 minutes, and after insoluble matters were removed by celite filtration, the solution was concentrated under a reduced pressure. The resulting colorless oily substance, i.e., (1S, 4aS, 7S, 7aR)-1-[1-(ethoxy)ethoxy]-1,4a,5,6,7,7a-hexahydro-4-(hydroxymethyl)-7methylcyclopenta[c]pyran (12.1 g, yield=90.2%) had the following physicochemical properties:

Proton NMR spectrum (δ ppm in CDCla): 1.09 (3H, d, J=6 Hz), 1.21 (3H, d, J=6 Hz), 1.36 (3H, d, J=5 Hz), 1.40–2.84 (7H, m), 2.74 (1H, q, J=8 Hz), 3.40–3.88 (2H, m), 4.00 (2H, q, J=12 Hz), 4.70 (0.2H, d, J=6 Hz), 4.80 (0.8H, d, J=6 Hz), 4.88 (0.2H, d, J=5 Hz), 4.99 (0.8H, d, J=5 Hz), 6.28 (1H, s) IR absorption spectrum υ neat max cm$^{-1}$: 3416, 2952, 1666, 1380, 1146, 1004 Mass spectrum m/z(%): 255 (M+H)$^+$

EXAMPLE 6

(1S, 4aS, 7S, 7aR)-1-[1-(ethoxy)ethoxy]-1,4a,5,6,7,7a-hexahydro-4-(hydroxymethyl)-7methylcycopenta[c]-pyran (10.0 g, 0.039 mol) obtained in Example 5 was dissolved in 200 ml of dichloromethane. After 9.52 ml (0.12 mol) of pyridine, 11.2 ml (0.12 mol) of acetic anhydride and 100 mg of N, N-dimethylaminopyridine were added, the reaction mixture was stirred at room temperature for 5 hours. After 600 ml of ethyl acetate was added to the reaction mixture solution, the organic layer was washed with water (300 ml×2), 2N hydrochloric acid solution, saturated sodium bicarbonate solution (300 ml×2) and saturated sodium chloride solution (300 ml), and was thereafter dried by magnesium sulfate, filtered, and then concentrated under a reduced pressure. The residual substance was purified by chromatography using silica gel, and the fraction obtained from hexane:ether=1:1 eluent was concentrated. A colorless oily matter was thus obtained, i.e., (1S, 4aS,7S, 7aR)-4-(acetoxymethyl)-1-[1-(ethoxy)ethoxy]1,4a,5,6,7,7a-hexahydro-7-methylcyclopenta[c]-pyran (9.27 g, yield=79.5%). This (1S, 4aS, 7S, 7aR)-4-(acetoxymethyl)-1-[1-(ethoxy)ethoxy]-1, 4a, 5, 6, 7, 7a-hexahydro-7-methylcyclopenta[c]pyran had the following physicochemical properties:

Proton NMR spectrum (δ ppm in CDCl$_{13}$): 1.13 (3H, d, J=4 Hz), 1.21 (3H, d, J=7 Hz), 1.37 (3H, d, J=4 Hz), 2.04 (3H, s), 1.42–2.78 (7H, m), 3.30–4.08 (2H, m), 4.37–5.01 (4H, m), 6.36 (1H, d, J=8 Hz) IR absorption spectrum υ neat max cm$^{-1}$: 2952, 2876, 1742, 1666, 1380, 1230, 1154, 1076, 1018, 954

EXAMPLE 7

(1S, 4aS, 7S, 7aR)-4-(acetoxymethyl)-1-[1-(ethoxy)ethoxy]-1,4a,5,6,7,7a-hexahydro-7-methoxycyclopenta[c]pyran (40.0 g, 0.135 mol) obtained in EXAMPLE 6 was dissolved in 1,000 ml of ethyl acetate.

After 20 ml of pyridine was added, 10% palladium carbon (1.2 g) was suspended in the reaction solution, and this solution was stirred for 48 hours in a hydrogen gas atmosphere of 1 atm. After the catalyst was removed by celite filtration, 1,000 ml of ethyl acetate was added, and this organic layer was washed with 2N hydrochloric acid solution (1,000 ml) and saturated sodium chloride solution (1,000 ml). The organic layer was dried by magnesium sulfate, and was filtered, and then concentrated under a reduced pressure. The residual matter was purified by chromatography using silica gel, and the solvent of the fraction obtained from hexane:ether=8:2 eluent was distilled off. A colorless oily substance was thus obtained, i.e., (1S, 4aS, 7S, 7aR)-1-[1-(ethoxy)ethoxy]-1,4a,5,6,7,7a-hexahydro-4,7-dimethylcyclopenta[c]pyran (29.5 g, yield=93.1%). This (1S, 4aS, 7S, aR)-1-[1-(ethoxy)ethoxy]-1,4a,5,6,7,7a-hexahydro-4, 7-dimethylcyclopenta[c]pyran had the following physicochemical properties:

Proton NMR spectrum ($\delta$ ppm in CDCl$_3$): 1.07 (3H, d, J=6 Hz), 1.20 (3H, t, J=7 Hz), 1.35 (3H, d, J=5 Hz), 1.61 (3H, s), 1.35–2.62 (7H, m), 3.46–3.80 (2H, m), 4.70 (0.4H, d, J=8 Hz), 4.80 (0.6H, d, J=5 Hz), 4.88 (0.4H, d, J=7 Hz), 4.98 (0.6H, d, J=6 Hz), 5.96 (1H, d, J=3 Hz) IR absorption spectrum $\nu$ neat max cm$^{-1}$: 2952, 1672, 1454, 1380, 1338, 1142, 1076, 1016, 992, 954, 888 Mass spectrum m/z (%): 240 (M+)

EXAMPLE 8

(1S, 4aS, 7S, 7aR)-1-[1-(ethoxy)ethoxy]-1,4a,5,6,7,7a-hexahydro-4,7-dimethylcyclopenta[c]pyran (20.0 g, 0.083 mol) obtained in Example 7 was dissolved in 500 ml of ethyl acetate. After 10% palladium carbon (600 mg) was suspended, the reaction solution was stirred for 48 hours in a hydrogen gas atmosphere of 1 atm. The catalyst was removed by celite filtration, and the reaction solution was concentrated under a reduced pressure. The residual matter was purified by chromatography using silica gel, and the solvent of the fraction obtained from hexane:ether=8:2 eluent was distilled off. A colorless oily substance was thus obtained, i.e., (1S, 4R, 4aR, 7S, 7aR)-1-[1-(ethoxy)ethoxy]-4, 7-dimethyl-1, 3, 4, 4a, 5, 6, 7, 7a-octahydro[c]pyran (19.2 g, 95.2%). This (1S, 4R, 4aR, 7S, 7aR)-1-[1(ethoxy)ethoxy]-4,7-dimethyl-1,3,4,4a,5,6,7,7a-octahydro[c]pyran had the following physicochemical properties:

Proton NMR spectrum ($\delta$ ppm in CDCl$_3$): 0.76 (3H, d, J=7 Hz), 1.01 (3H, d, J=6 Hz), 1.21 (3H, t, J=7 Hz), 1.37 (3H, d, J=5 Hz), 1.48–2.14 (8H, m), 3.08–3.92 (4H, m), 4.92–5.00 (2H, m) IR absorption spectrum $\nu$ CHCl$_3$ max cm$-$1: 2948, 2872, 1458, 1380, 1336, 1128, 988, 950, 892

EXAMPLE 9

Methyl (1S, 4aS, 7S, 7aR)-1-[1-(ethoxy)ethoxy]-7-methyl-1,4a,5,6,7,7a-hexahydrocyclopenta[c]pyran-4carboxylate (1.0 g, 0.0035 mol) obtained in Example 4 was dissolved in 20 ml of ethanol suspending nickel chloride (1.14 g), and 10 ml of an ethanol solution of sodium boron hydride (830 mg, 0.021 mol) was added. Thereafter, the reaction solution was stirred at 80° C. for 3 hours under heat-reflux. The reaction mixture solution was filtered by a celite, and was once concentrated under a reduced pressure. The residual matter was dissolved in 100 ml of ethyl acetate, washed with water (50 ml×3) and dried by the addition of magnesium sulfate. The residual matter was further filtered, and the solvent was distilled off under a reduced pressure. The residual matter was dissolved in 30 ml of tetrahydrofuran without purification and was stirred at room temperature for 2 hours after the addition of 10 ml of 2N hydrochloric acid solution. After the reaction solution was neutralized by adding 50 ml of saturated sodium bicarbonate solution, it was extracted by ethyl acetate (50 ml×3). After the organic layer was joined, it was dried by the addition of magnesium sulfate, filtered, and then concentrated under a reduced pressure. The residual matter was purified by chromatography using silica gel, and the solvent of the fraction obtained from hexane:ether=7:3 eluent was distilled off. A colorless oily substance was thus obtained, i.e., methyl (4aS, 7S, 7aR)-1, 3, 4, 4a, 5, 6, 7, 7a-octahydro-1-hydroxy-7-methylcyclopenta[c]pyran-4-carboxylate (480 mg, yield=63.7%)- This methyl (4aS, 7S, 7aR)1, 3, 4, 4a, 5, 6, 7, 7a-octahydro-1-hydroxy-7methylcyclopenta[c]pyran-4-carboxylate had the following physicochemical properties:

Proton NMR spectrum ($\delta$ ppm in CDCl$_3$): 1.03 (3H, d, J=6 Hz), 1.08–2.08 (5H, m), 2.26–2.64 (2H, m), 2.96 (1H, brs), 3.69 (3H, s), 3.91–4.20 (2H, t, J=12 Hz), 5.30 (1H, brs) IR absorption spectrum $\nu$ neat max cm$^{-1}$: 3592, 2952, 2872, 1728, 1632, 1436, 1378, 1276, 1168, 1106, 1006

EXAMPLE 10

Methyl (4aS, 7S, 7aR)-1-hydroxy-7-methyl-1,4a,5,6,7,7a-hexahydrocyclopenta[c]pyran-4-carboxylate (750 mg, 0.0035 mol) obtained in Definite Example 4 was dissolved in 15 ml of dichloromethane, and 3.5 ml (0,035 mol) of dihydropyran and 25 mg of pyridinium p-toluensulfonate were further added. The reaction mixture solution was stirred at room temperature for 24 hours. The reaction mixture was poured into 30 ml of dichloromethane, and was washed with a mixed aqueous solution of saturated sodium bicarbonate solution (10 ml) and saturated sodium chloride solution (10 ml). The mixture was dried by the addition of magnesium sulfate, filtered, and then concentrated under a reduced pressure. The residual matter was purified by chromatography using silica gel, and the solvent of the fraction obtained from hexane:ether=8:2 eluent was distilled off. A colorless oily substance was thus obtained, i.e., methyl (1S, 4aS, 7S, 7aR)-1,4a,5,6,7,7a-hexahydro-1-(2-tetrahydropyranyloxy)-7-methylcyclopenta[c]pyran-4-carboxylate (920 mg, yield=87.9%). This methyl (1S, 4aS, 7S, 7aR)-1,4a,5,6,7,7a-hexahydro-1-(2-tetrahydropyranyloxy)-7-methylcyclopenta[c]pyran-4-carboxylate had the following physicochemical properties:

Proton NMR spectrum ($\delta$ ppm in CDCl$_3$): 1.10 (3H, t, J=6 Hz), 1.26–2.52 (13H, m), 2.76–2.92 (1H, m), 3.44 IR absorption spectrum $\nu$ CHCl$_3$ max cm$^{-1}$: 2948, 1704, 1632, 1438, 1356, 1284, 1096, 966, 904 Mass spectrum m/z (%): 297 (M+H)+

EXAMPLE 11

Methyl (1S, 4aS, 7S, 7aR)-1,4a,5,6,7,7a-hexahydro-1-(2-tetrahydropyranyloxy)-7-methylcyclopenta[c]pyran-4-carboxylate (1.25 g, 0.0042 mol) obtained in Example 10 was dissolved in 20 ml of anhydrous tetrahydrofuran, and the reaction solution was cooled by ice in the atmosphere of an argon gas. Then, 7 ml of diisobutylaluminum hydride (1.5 mol, toluene solution) was added dropwise. After the reaction mixture was stirred at the same temperature for 2 hours, ml of acetone was added and furthermore, a 3% aqueous sodium hydroxide solution was added dropwise. The reaction mixture solution was stirred for 1 hour. Magnesium sulfate was added to the solution and 20 minutes later, insoluble matters were filtered by a celite and concentrated under a reduced pressure. The resulting colorless oily substance, i.e., (1S, 4aS, 7S, 7aR)-1,4a,5,6,7,7a-hexahydro-4-(hydroxymethyl)-1-(2-tetrahydropyranyloxy)-7-methylcyclopenta[c]pyran (0.95 mg, yield=83.9%) had the following physicochemical properties:

Proton NMR spectrum (δ ppm in CDCl$_3$): 1.08 (1.5H, d, J=8 Hz), 1.13 (1.5H, d, J=8 Hz), 1.24–3.12 (13H, m), 3.44–4.16 (4H, m), 4.84–5.60 (2H, m), 6.32 (1H, d, J=8 Hz)

EXAMPLE 12

2.0 g of genipin (0.0088 mol) was dissolved in 10 ml of dichloromethane, and 7 ml of pyridine (0.088 mol) and 10.1 g (0.044 mol) of benzoic anhydride were added. Furthermore, 50 mg of N,N-dimethylaminopyridine was added and the reaction mixture was stirred at room temperature for 5 hours. The reaction mixture was extracted by adding 100 ml of ethyl acetate. After the organic layer was washed with 2N hydrochloric acid solution (50 ml×2), saturated sodium bicarbonate solution (50 ml) and saturated sodium chloride solution (50 ml), it was dried by the addition of magnesium sulfate, filtered, and then concentrated under a reduced pressure. The residual matter was purified by chromatography using silica gel, and the solvent of the fraction obtained from hexane:ether=4:6 eluent was distilled off. A colorless oily substance was thus obtained, i.e., methyl (1S, 4aS, 7aS)-1-benzoyloxy-7-(benzoyloxymethyl)-1,4a,5,7a-tetrahydro[c]pyran-4-carboxylate (3.23 g, yield=84.1%). This methyl (1S, aS, 7aS)-1-benzoyloxy-7-(benzoyloxymethyl)-1, 4a, 5, 7a-tetrahydro[c]pyran-4-carboxylate had the following physicochemical properties:

Proton M spectrum (δ ppm in CDCl$_3$): 1.20–1.36 (1H, brs), 2.24–2.40 (1H, m), 2.90–3.56 (2H, m), 3.80 (3H, s), 4.92 (2H, brs), 6.08 (1H, brs), 6.28 (1H, d, J=8 Hz), 7.56 (1H, s), 7.38–7.80 (5H, m), 8.00–8.16 (5H, m) IR absorption spectrum υCHCl$_3$ max cm$^{-1}$: 1714, 1636, 1604, 1450, 1266, 1450, 1266, 1090, 908 Mass spectrum m/z (%): 435 (M+H)+

EXAMPLE 13

Genipin (1.0 g, 0.0044 mol) was dissolved in 20 ml of anhydrous tetrahydrofuran, and diisobutylaluminum hydride (1.5M toluene solution, 17.7 ml) was added dropwise while the reaction mixture was cooled with ice. After the reaction mixture was stirred at the same temperature for 2 hours, 10 ml of acetone was added and stirring was continued for further 20 minutes. Furthermore, 8 ml of water and 2 ml of 15% sodium hydroxide were added, and the reaction mixture was stirred for 1 hour. Thereafter, celite filtration was carried out by adding magnesium sulfate. The residue obtained by concentrating the filtrate was purified by chromatography using silica gel, and there was thus obtained a colorless oily substance, i.e., 2-[(1S, 2S)-2,3-bis(hydroxymethyl)-3,4-dehydrocyclopent-1-yl]-2-propan-1-ol (245 mg, 30.1%) from dichloromethane:methanol=7:1 eluent. This 2-[(1S, 2S)-2,3-bis(hydroxymethyl)-3,4-dehydrocyclopent-1-yl]2-propan-1-ol had the following physicochemical properties:

Proton NMR spectrum (δ ppm in CDCl$_{13}$): 2.08–3.20 (4H, m), 3.34–4.04 (2H, m), 4.04–4.53 (4H, m), 5.03 (1H, s), 5.24 (1H, s), 5.85 (1H, s) IR absorption spectrum υ neat max cm$^{-1}$: 3392, 2924, 1712, 1402, 1170, 1032, 910, 828, 730, 646

EXAMPLE 14

Genipin (2.0 g, 0–0088 mol) was dissolved in 10 ml of dichloromethane, and 5.45 ml (0.44 mol) of pivaloyl chloride and pyridine (7 ml, 0.088 mol) were added, Furthermore, 50 mg of N,N-dimethylaminopyridine was added, the reaction mixture solution was stirred at room temperature for 5 hours. Then, the reaction mixture solution was poured into 100 ml of ethyl acetate, and the organic layer was washed with 2N hydrochloric acid solution (50 ml×2), saturated sodium bicarbonate solution (50 ml×2) and saturated sodium chloride solution (50 ml), was dried by adding magnesium sulfate, and was filtered and then concentrated under a reduced pressure. The residual matter was purified by chromatography using silica gel, and the solvent of the fraction obtained from hexane:ether=1:1 eluent was distilled off. A colorless oily substance was thus obtained, i.e., methyl (1S, 4aS, 7aS)-1,4a,5,7a-tetrahydro-1-trimethylacetoxy-7-(trimethylacetoxymethyl) cyclopenta[c]pyran-4-carboxylate (2.62 g, yield=75.2%). This methyl (1S, 4aS, 7aS)-1,4a,5,7a-tetrahydro-1-trimethylacetoxy-7-(trimethylacetoxymethyl)cyclopenta[c]-pyran-4-carboxylate had the following physicochemical properties:

Proton NMR spectrum (δ ppm in CDCl$_3$): 1.22 (9H, s), 1.24 (9H, s), 1.12–1.36 (1H, m), 2.80–2.96 (2H, m), 3.24–3.36 (1H, m), 3.74 (3H, s), 4.61–4.80 (2H, m), 5.88–6.08 (2H, m), 7.46 (1H, s) IR absorption spectrum υ neat max cm$^{-1}$: 2956, 1724, 1638, 1478, 1368, 1278, 1146, 908 Mass spectrum m/z (%): 395 (M+H)+

EXAMPLE 15

Methyl (1S, 4aS, 7aS)-1,4a,5,7a-tetrahydro-1-trimethylacetoxy-7-(trimethylacetoxymethyl)cyclopenta[c]-pyran-4-carboxylate (200 mg, 0.00051 mol) obtained in Example 14 was dissolved in 15 ml of tetrahydrofuran, and 10% palladium carbon (10 mg) was suspended. After ammonium formate (320 mg, 0.0046 mol) was added, the reaction mixture was refluxed at 80° C. Twelve hours later, celite filtration was carried out, and 50 ml of ethyl acetate was added to the filtrate. After this organic layer was washed with saturated sodium chloride solution (30 ml), it was dried by adding magnesium sulfate, filtered, and then concentrated under a reduced pressure. The residual matter was purified by chromatography using silica gel, and the solvent of the fraction obtained from hexane:ether=8:2 eluent was concentrated. A colorless oily substance was thus obtained, i.e., methyl (1S, 4aS, 7aS)-1,4a,5,7a-tetrahydro-7-methyl-1-trimethylacetoxycyclopenta[c]-pyran4-carboxylate (114.5 mg, yield=72.8%). This methyl (1S, 4aS, 7aS)-1,4a,5,7a-tetrahydro-7-methyl-1-trimethylacetoxycyclopenta[c]pyran-4-carboxylate had the following physicochemical properties:

Proton NMR spectrum (δ ppm in CDCl$_3$): 1.25 (9H, s), 1.80 (2H, brs), 2.64–2.80 (1H, m), 3.16–3.32 (1H, m), 3.73 (3H, s), 5.56 (1H, brs), 5.91 (1H, d, J=7 Hz), 7.43

(1H, s) IR absorption spectrum υ CHCl₃ max cm⁻¹: 1706, 1637, 1285, 1087, 901

EXAMPLE 16

10.0 g of genipin (0.044 mol) was dissolved in 100 ml of dimethylformamide, and 6.0 g (0.088 mol) of imidazole and 13.3 g (0.088 mol) of tert-butyldimethylsilyl chloride (0.088 mol) were added. The reaction mixture was stirred at room temperature for 24 hours. The reaction mixture solution was extracted by adding 700 ml of ethyl acetate, and the organic layer was washed with water (300 ml×2), saturated sodium bicarbonate solution (300 ml) and saturated sodium chloride solution (300 ml), and was then dried by adding magnesium sulfate, filtered, and thereafter concentrated under a reduced pressure. The residual matter thus obtained was determined to be methyl (4aS, 7aS)-(7-tert-butyldimethylsilyloxymethyl)-1-hydroxy-1,4a,5,7a-tetrahydrocyclopenta[c]pyran-4-carboxylate because it had the following physicochemical properties:

Proton NMR spectrum (δ ppm in CDCl₃): 0.17 (6H, d, J=4 Hz), 0.93 (9H, s), 1.23–3.30 (4H, m), 3.76 (3H, s), 4.16 (2H, m), 5.83 (1H, brs), 7.60 (1H, s)

The compound described above, i.e., methyl (4aS, 7aS)-(7-tert-butyldimethylsilyloxymethyl)-1-hydroxy-1,4a,5,7a-tetrahydrocyclopenta[c]pyran-4-carboxylate (10.0 g, 0.03 mol) was dissolved in 200 ml of dichloroethane, and 300 ml of ethyl vinyl ether and 50 mg of pyridinium p-toluenesulfonate were added. The reaction mixture was stirred at room temperature for 24 hours. Furthermore, 300 ml of dichloromethane was added, and the reaction mixture was washed with a mixed aqueous solution of 100 ml of saturated sodium chloride solution and 100 ml of saturated sodium bicarbonate solution. The organic layer was dried by adding magnesium sulfate, then filtered, and thereafter concentrated under a reduced pressure. The residual matter was dissolved in 200 ml of tetrahydrofuran without purification, and 15 ml of n-tetrabutylammonium fluoride was added. This solution was stirred at room temperature for 5 hours. After 300 ml of ethyl acetate was added to this reaction mixture solution, the organic layer was washed with water (300 ml×2) and 300 ml of saturated sodium chloride solution, dried by adding magnesium sulfate, then filtrated and concentrated under a reduced pressure. The residual matter was purified by chromatography using silica gel, and the solvent of the fraction obtained from hexane:ether=1:1 eluent was distilled off. A pale yellow oily matter was thus obtained (10.4 g, yield=78.9%). Since this compound had the following physicochemical properties, it was determined as methyl (1S, 4aS, 7aS)-1-[1-(ethoxy)ethoxy]-7-(hydroxymethyl)-1,4a,5,7a-tetrahydrocyclopenta[c]pyran-4-carboxylate.

Proton NMR spectrum (δ ppm in CDCl₃): 1.20 (3H, q, J=8 Hz), 1.39 (3H, d, J=8 Hz), 2.00–3.90 (6H, m), 3.79 (3H, s), 4.29 (2H, brs), 4.74 (0.5H, d, J=8 Hz), 4.88 (0.5H, d, J=10 Hz), 4.96 (0.5H, q, J=7 Hz), 5.10 (0.5H, q, J=7 Hz), 5.85 (1H, brs), 7.54 (1H, s)

EXAMPLE 17

Methyl (1S, 4aS, 7aS)-1-[1-(ethoxy)ethoxy]-7-(hydroxymethyl)-1,4a,5,7a-tetrahydrocyclopenta[c]-pyran-4-carboxylate (2.0 g, 0.0067 mol) obtained in Example 16 was dissolved in 30 ml of dimethylformamide, and 540 mg (0.013 mol) of sodium hydride (in 60% oil) was added while the reaction mixture was being cooled by ice and stirred. After the reaction mixture was stirred at the same temperature for 30 minutes, 1.9 g (0.013 mol) of methyl iodide was added dropwise. After the temperature was raised up to the room temperature and the reaction mixture was stirred for 2 hours, the reaction mixture was extracted by adding 50 ml of 2N hydrochloric acid solution and 200 ml of ethyl acetate. The organic layer was washed with water (100 ml×2), saturated sodium bicarbonate solution (100 ml) and saturated sodium thiosulfate (100 ml), it was dried by adding magnesium sulfate and was then filtered, and thereafter concentrated under a reduced pressure. The residual matter was purified by chromatography using silica gel, and the solvent of the fraction obtained from hexane:ether=7:3 eluent was distilled off. A colorless oily substance was thus obtained, i.e., methyl (1S, 4aS, 7aS)-1-[1-(ethoxy)ethoxy]-7-(methoxymethyl)-1,4a, 5, 7a-tetrahydrocyclopenta[c]pyran-4-carboxylate (1.71 g, yield=81.8%). This methyl (1S, 4aS, 7aS)-1-[1-(ethoxy)ethoxy]-7-(methoxymethyl)-1 ,4a,5,7a-tetrahydrocyclopenta[c]pyran-4-carboxylate had the following physicochemical properties:

Proton NMR spectrum (δ ppm in CDCl₃): 1.15–1.26 (3H, m), 1.37 (3H, d, J=5 Hz), 1 64–2.96 (4H, m), 3.12–3.84 (2H, m), 3.35 (3H, s), 3.72 (3H, s), 4.09 (1H, brs), 4.81 (0.5H, d, J=7 Hz), 4.91 (0.5H, d, J=5 Hz), 4.96 (0.5H, d, J=7 Hz), 5.03 (0.5H, d, J=5 Hz), 5.84 (1H, brs), 7.48 (1H, d, J=4 Hz) Mass spectrum m/z (%): 313 (M+H)+

EXAMPLE 18

Methyl (1S, 4aS, 7aS)-1-[1-(ethoxy)ethoxy]-7-(methoxymethyl)-1,4a,5,7a-tetrahydrocyclopenta[c]-pyran-4-carboxylate (1.71 g, 0.0055 mol) obtained in Example 17 was dissolved in 40 ml of tetrahydrofuran, and 20 ml of 2N hydrochloric acid solution was added dropwise. The reaction mixture was stirred at room temperature for 3 hours, and 100 ml of saturated sodium bicarbonate was added. The reaction mixture solution was extracted by ethyl acetate (100 ml×2). The joined organic layer was dried by adding magnesium sulfate, and was then filtered, and thereafter concentrated under a reduced pressure. The residual matter was purified by chromatography using silica gel, and the solvent of the fraction obtained from hexane:ether=7:3 eluent was distilled off. A colorless oily substance was thus obtained (750 mg, yield=46.6%). Since this compound had the following physicochemical properties, it was determined as methyl (4aS, 7aS)-1-hydroxy-7-methoxymethyl)-1,4a,5,7a-tetrahydrocyclopenta[c]pyran-4-carboxylate.

Proton NMR spectrum (δ ppm in CDCl₃): 1.96–3.20 (4H, m), 3.39 (3H, s), 3.72 (3H, s), 4.13 (2H, m), 4.80 (0.5H, d, J=8 Hz), 5.38 (0.5H, brs), 5.91 (1H, brs), 7.54 (1H, s) IR absorption spectrum υ CHCl₃ max cm⁻¹: 3304, 2944, 2856, 1702, 1632, 1438, 1380, 1286, 1144, 1104, 970, 908 Mass spectrum m/z (%): 241 (M+H)+

EXAMPLE 19

Methyl (1S, 4aS, 7aS)-1-[1-(ethoxy)ethoxy]-7-formyl-1,4a,5,7a-tetrahydrocyclopenta[c]pyran-4-carboxylate (200 mg, 0.00068 mol) obtained in Definite Example 22 was dissolved in 13 ml of tert-butanol, and 3 ml of 2-methyl-2-butene was added. While the solution was being stirred, 570 mg (0.006 mol) of sodium chloride and 610 mg (0.005 mol) of sodium phosphate dissolved in 5 ml of water were added dropwise. After the reaction solution was stirred for 24 hours, sodium chloride was added and the reaction solution was stirred for 10 minutes, and was then extracted by ethyl acetate (50 ml×3). The organic layer was joined and dried by adding magnesium sulfate and was then filtered, and thereafter concentrated under a reduced pressure. Since the residual matter had the following physicochemical properties, it was determined to be methyl (1S, 4aS, 7aS)-7-carboxy-1-[1-(ethoxy)ethoxy]-1, 4a,5,7a-tetrahydrocyclopenta[c]pyran-4-carboxylate (190 mg, yield=90.1%).

Proton NMR spectrum (δ ppm in CDCl$_3$): 1.18 (3H, t, J=7 Hz), 1.28-1.37 (3H, m), 1.62-3.52 (6H, m), 3.73 (3H, s), 4.84-5.02 (1H, m), 7.06 (0.5H, brs), 7.13 (0.5H, brs), 7.50 (0.5H, s), 7.56 (0.5H, s), 7.96 (1H, brs) Mass spectrum m/z (%): 313 (M+H)+

The above-mentioned compound, i.e., methyl (1S, 4aS, 7aS)-7-carboxy-1-[1-(ethoxy)ethoxy]-1-4a, 5,7tetrahydrocyclopenta[c]pyran-4-carboxylate (5.6 g) (0.018 mol) was dissolved in 100 ml of tetrahydrofuran, and after 30 ml of 2N hydrochloric acid solution was added, the reaction mixture was stirred at room temperature for 3 hours. After sodium chloride was added and the reaction mixture was further stirred for 10 minutes, it was extracted by ethyl acetate (200 ml×3). The organic layer was dried by adding magnesium sulfate, filtered, and thereafter concentrated under a reduced pressure. The residual matter was purified by chromatography using silica gel, and the solvent of the fraction obtained from chloroform:ethanol=3:1 eluent was distilled off. The residual matter was crystallized by adding ether, and the resulting crystal was filtrated and collected. This yellow powder crystal, i.e., methyl (4aS, 7aS)-7-carboxy-1,4a,5,7a-tetrahydro-1-hydroxycyclopenta[c]-pyran-4-carboxylate (3.18 g, 73.8%) had the following physico-chemical properties:

Proton NMR spectrum (δ ppm in CDCl$_3$): 2.123.40 (4H, m), 3.74 (1.8H, s), 3.75 (1.2H, s), 4.87 (0.6H, d, J=8 Hz), 5.53 (0.4H, brs), 7.02 (1H, brs), 7.50 (0.4H, s), 7.56 (0.6H, s) Mass spectrum m/z (%): 241 (M+H)+

EXAMPLE 20

Methyl (4aS, 7aS)-(7-tert-butyldimethyl-silyloxymethyl)-1-hydroxy-1,4a,5,7tetrahydrocyclopenta[c]pyran-4-carboxylate (1.1 g, 0.0032 mol) was dissolved in 20 ml of a-dichloromethane, and 0.78 ml of pyridine and acetic anhydride (0.92 ml, 0.0096 mol) were added. After 30 mg of N,N-dimethylaminopyridine was further added, the reaction mixture was stirred at room temperature for 5 hours. The reaction mixture was then extracted by adding ethyl acetate (100 ml). The organic layer was washed with water (50 ml×2), 2N hydrochloric acid solution (50 ml×2), saturated sodium bicarbonate solution (100 ml), and saturated sodium chloride solution (100 ml), and was then dried by adding magnesium sulfate, filtered, and thereafter concentrated under reduced pressure. The residual matter was purified by chromatography using silica gel, and a colorless oily substance was obtained from hexane:ether=3:7 eluent. Since this compound had the following physicochemical properties, it was determined as methyl (1S, 4aS, 7aS)-1-acetoxy-(7-tert-butyldimethylsiloxymethyl)-1,4a,5,7a-tetrahydrocyclopenta[c]pyran-4-carboxylate (1.16 g, 93.7%).

Proton NMR spectrum (δ ppm in CDCl$_3$): 0.07 (6H, brs), 0.91 (9H, s), 1.84 (1H, brs), 2.14 (3H, s), 2.88 (2H, m), 3.30 (1H, s), 3.73 (3H, s), 4.26 (2H, brs), 5.92 (1H, brs), 5.98 (1H, d, J=6 Hz), 7.43 (1H, brs), IR absorption spectrum υ neat max cm$^{-1}$: 2952, 2860, 1758, 1706, 1636, 1438, 1366, 1282, 1088, 832 Mass spectrum m/z (%): 323 (M-58)+

EXAMPLE 21

Genipin (30.0 g, 0.133 mol) was dissolved in 500 ml of dichloromethane, and after pyridine (100 ml), acetic anhydride (115 ml ) and N,N-dimethylaminopyridine (200 mg) were added, the reaction mixture was stirred at room temperature for 10 hours. After 2,000 ml of dichloromethane was added, the reaction mixture was extracted. The organic layer was washed with water (1,000 ml ), 2N hydrochloric acid solution (1,000 ml×2), saturated sodium bicarbonate solution (1,000 ml×2) and saturated sodium chloride solution (1,000 ml), and was dried by adding magnesium sulfate. It was then filtered and was thereafter concentrated under a reduced pressure. The residual matter was purified by chromatography using silica gel, and a pale yellow oily matter (38.6 g, yield=96.3%) obtained by concentrating the hexane:ether=7:3 fraction had the following physicochemical properties: hence, it was determined to be methyl (1S, 4aS, 7aR)-1-acetoxy-7-(acetoxymethyl)-1,4a,5,7a-tetrahydrocyclopenta[c]pyran-4-carboxylate.

Proton NMR spectrum (δ ppm in CDCl$_3$): 1.83-2.10 (1H, m), 2.09 (3H, s), 2.16 (3H, s), 2.80-2.96 (2H, m), 3.22-3.40 (1H, m), 3.74 (3H, s), 4.56-4.80 (2H, m), 5.87 (1H, d, J=7 Hz), 5.94 (1H, brs), 7.46 (1H, s) Mass spectrum m/z (%): 311 (M+H)+

The above-mentioned compound, i.e., methyl (1S, 4aS, 7aR)-1-acetoxy-7-(acetoxymethyl)-1,4a,5,7a-tetrahydrocyclopenta[c]pyran-4-carboxylate (10.0 g, 0.032 mol) was dissolved in a mixed solvent of 200 ml of tetrahydrofuran and 60 ml of water, and 22 g (0.32 mol) of sodium formate and 300 mg of bis(triphenylphosphine)palladium dichloride were added to this solution. The reaction mixture was heated and stirred at 80°. Two hours later, heating was stopped, and insoluble matters in the reaction solution were removed by celite filtration. After 300 ml of water was added, the solution was extracted by ethyl acetate (500 ml×2). The joined organic layer was dried by adding magnesium sulfate and filtered, and thereafter concentrated under a reduced pressure. The residual matter was purified by chromatography using silica gel, and the solvent of the fraction obtained from hexane:ether=1:1 eluent was distilled off. A colorless oily substance was thus obtained (8.26 g, yield=95.5%). Since this colorless oily substance had the following physicochemical properties, it was determined as methyl (1S, 4aS, 7aR)-1-acetoxy-7-methylene-1,4a,5,6,7a-pentahydrocyclopenta[c]pyran-4-carboxylate.

Proton NMR spectrum (δ ppm in CDCl$_3$): 1.48-1.76 (2H, m), 2.28-3.08 (4H, m), 3.74 (3H, s), 5.10 (2H, d, J=2 Hz), 5.92 (1H, d, J=7 Hz), 7.44 (1H, s)

EXAMPLE 22

Methyl (1S, 4aS, 7aR)-1-acetoxy-7-methylene-1,4a,5,6,7a-pentahydrocyclopenta[c]pyran-4-carboxylate (7.75 g, 0.03 mol) obtained in Example 21 was dissolved in 300 ml of tetrahydrofuran, and after 70 ml of 2N hydrochloric acid solution wad added, the reaction mixture was stirred at room temperature. Five hours later, 300 ml of saturated sodium bicarbonate solution was added to the reaction mixture, extraction was carried out using ethyl acetate (500 ml×2). The joined organic layer was dried by adding magnesium sulfate, and was filtered and thereafter concentrated under a reduced pressure. The residual matter was purified by chromatography using silica gel, and the solvent of the fraction obtained from hexane:ether=7:3 eluent was distilled off. A colorless oily substance was thus obtained (5.55 g, yield=85.7%). Since this colorless oily substance had the following physicochemical properties, it was determined as methyl (4aS, 7aS)-1-hydroxy-7-methylene-1,4a,5,6,7a-pentahydrocyclopent[c]pyran-4-carboxylate.

Proton NMR spectrum (δ ppm in CDCl₃): 1.24–3.08 (6H, m), 3.73 (3H, s), 4.90–5.21 (3H, m), 7.49 (1H, s) IR absorption spectrum υ neat max cm⁻¹: 3588, 3360, 2948, 1704, 1632, 1436, 1386, 1284, 1142, 1100, 974, 904 Mass spectrum m/z (%): 211 (M+H)+

EXAMPLE 23

Methyl (4aS, 7aS)-1-hydroxy-7-methylene-1,4a,5,6,7a-pentahydrocyclopenta[c]pyran-4-carboxylate (2.0 g, 0.0095 mol) obtained in Example 22 wad dissolved in 40 ml of tetrahydrofuran, and after sodium boron hydride (1.8 g, 0.047 mol) was added, the reaction mixture was heated and refluxed at 80° C. 9.5 ml of methanol wad added dropwise to this solution in the course of 1 hour, and the reaction mixture was stirred further at the same temperature. 50 ml of saturated ammonium chloride solution wad added to the reaction mixture. After an organic solvent was once distilled off, the aqueous layer was extracted by ethyl acetate (100 ml×3). The organic layer was joined, and was dried by adding magnesium sulfate, filtered, and thereafter concentrated under a reduced pressure. The residual matter was purified by chromatography using silica gel, and the solvent of the fraction obtained from ether:ethyl acetate=3:7 eluent was distilled off. A colorless oily substance was thus obtained, i.e., 2-[(1R, 2R)-2-(hydroxymethyl)-3-methylenecyclopent-1-yl]-ethane-1-ol (450 mg, yield=30.2%). This 2-[(1R, 2R)-2-(hydroxymethyl)-3-methylcyclopent-1-yl]-ethane-1-ol had the following physicochemical properties:

Proton NMR spectrum (δ ppm in CDCl₃): 1.38–1.64 (2H, m), 1.68–1.88 (2H, m), 2.12–2.56 (3H, m), 2.60 (1H, d, J=12 Hz), 3.40–3.84 (4H, m), 4.90 (1H, brs), 4.98 (1H, brs)

EXAMPLE 24

Methyl (4aS, 7R, 7aR)-1,4a,5,6,7,7a-hexahydro-1-hydroxy-7-methylcyclopenta[c]pyran-4-carboxylate (2.40 g, 0.011 mol) obtained in Definite Example 31 was dissolved in 40 ml of dichloromethane. After 8.15 g (0.11 mol) of ethyl-vinyl ether wad added, 50 mg of pyridinium p-toluenesulfonate was added, and the reaction mixture was stirred at room temperature for 24 hours. The reaction mixture was poured into 100 ml of dichloromethane, and was washed with a mixed aqueous solution of saturated sodium bicarbonate (50 ml) and saturated sodium chloride solution (50 ml). The organic layer was dried by adding magnesium sulfate, and after it was filtered, it was concentrated under a reduced pressure. The residual matter was purified by chromatography using silica gel, and the solvent of the fraction obtained from hexane:ether=8:2 eluent was distilled off. A colorless oily substance was thus obtained, i.e., methyl (1S, 4aS, 7R, 7aR)-1-[1(ethoxy)ethoxy]-1,4a,5,6,7,7a-hexahydro-7-methylcyclopenta[c]pyran-4-carboxylate (3.01 g, 93.6%). This methyl (1S, 4aS, 7R, 7aR)-1-[1-(ethoxy)ethoxy]-1,4a,5,6,7,7a-hexahydro-7-methylcyclopenta[c]pyran-4carboxylate had the following physicochemical properties:

Proton NMR spectrum (δ ppm in CDCl₃): 1.05 (3H, m), 1.21 (3H, m), 1.36 (3H, m), 1.44–2.40 (6H, m), 2.96 (1H, q, J=8 Hz), 3.36–3.92 (2H, m), 3.71 (3H, s), 4.93 (0.5H, d, J=5 Hz), 4.99 (0.5H, d, J=3 Hz), 5.01 (0.5H, d, J=5 Hz), 5.17 (0.5H, d, J=4 Hz), 7.41 (1H, d, J=7 Hz) IR absorption spectrum υCHCl₃ max cm⁻¹: 2948, 1704, 1638, 1438, 1380, 1294, 1100, 978, 952, 898 Mass spectrum m/z (%): 285 (M+H)+

EXAMPLE 25

Methyl (1S, 4aS, 7R, 7aR)-1-[1-(ethoxy)ethoxy]-1,4a, 5, 6, 7, 7a-hexahydro-7-methylcyclopenta[c]pyran-4-carboxylate (3.00 g, 0.011 mol) obtained in Example 24 was dissolved in 70 ml of anhydrous tetrahydrofuran, and while the reaction mixture was being cooled with ice and stirred, 14.8 ml of diisobutylaluminum hydride (1.5M toluene solution) was added dropwise. The reaction mixture was stirred at the same temperature for 2 hours, 1.6 ml of acetone was added dropwise and the reaction mixture was again stirred for 20 minutes. Furthermore, 2 ml of 3% sodium hydroxide solution was added dropwise and the reaction mixture was stirred for 1 hour. After magnesium sulfate was added, the reaction mixture was further stirred for 20 minutes, unnecessary matters were filtered by a celite and the solvent was distilled off under a reduced pressure. A colorless oily substance was thus obtained, i.e., (1S, 4aS, 7R, 7aR)-1-[1-(ethoxy)ethoxy]-1,4a,5,6,7,7a-hexahydro-4-(hydroxymethyl)-7-methylcyclopenta[c]pyran (2.18 g, yield=81.5%). This (1S, 4aS, 7R, 7aR)-1-[1(ethoxy)ethoxy]-1,4a,5,6,7,7a-hexahydro-4-(hydroxymethyl)-7-methylcyclopenta[c]pyran had the following physicochemical properties:

Proton NMR spectrum (δ ppm in CDCl₃): 1.04 (3H, m), 1.21 (3H, m), 1.36 (3H, m), 1.44–2.40 (6H, m), 2.70–2.94 (1H, d, J=8 Hz), 3.18–4.20 (4H, m), 4.94–5.20 (2H, m), 6.27 (1H, d, J=6 Hz) IR absorption spectrum υ CHCl₃ max cm⁻¹: 3600, 3452, 2932, 1668, 1454, 1380, 1338, 1142, 986, 904, 644 Mass spectrum m/z (%): 255 (M+H)+

EXAMPLE 26

(1S, 4aS, 7R, 7aR)-1-[1-(ethoxy)ethoxy]-1,4a,5,6,7,7a-hexahydro-4-(hydroxymethyl)-7methylcyclopenta[c]pyran (100 mg, 0.00039 mol) obtained in Example 25 was dissolved in 5 ml of dichloromethane, and 0.15 ml (0.0016 mol) of pyridine and 0.1 ml (0.0012 mol) of acetic anhydride were added. Furthermore, 5 mg of N, N-dimethylaminopyridine was added, the reaction mixture was stirred at room temperature for 5 hours. Then, the reaction mixture was poured into 30 ml of ethyl acetate, and the organic layer was washed with water (30 ml), 2N hydrochloric acid solution (30 ml), saturated sodium bicarbonate solution (30 ml) and saturated sodium chloride solution (30 ml), was dried by adding magnesium sulfate, was filtered, and then concentrated under a reduced pressure. The residual matter was purified by chromatography using silica gel, and the fraction obtained from hexane:ether=6:4 eluent was concentrated. A colorless oily substance was thus obtained, i.e., (1S, 4aS, 7R, 7aR)-4-(acetoxymethyl)-1-[1-(ethoxy)ethoxy]-1,4a,5,6,7,7a-hexahydro-7-methylcyclopenta[c]pyran (71 mg, yield=61.0%). This (1S, 4aS, 7R, 7aR)-4-(acetoxymethyl)-1-[1-(ethoxy)ethoxy]-1,4a -hexahydro-7-methylcyclopenta[c]pyran had the following physicochemical properties:

Proton NMR spectrum (δ ppm in CDCl₃): 1.05 (3H, d, J=7 Hz), 1.22 (3H, t, J=4 Hz), 1.32 (3H, d, J=5 Hz), 1.60–1.88 (2H, m), 2.04 (3H, s), 2.10–2.25 (2H, m), 2.60–2.76 (1H, m), 3.38–3.84 (2H, m), 4.37 (0.5H, d, J=12 Hz), 4.57 (0.5H, d, J=12 Hz), 6.34 (1H, d, J=7 Hz) IR absorption spectrum υ neat max cm$^{-1}$: 2936, 2876, 1728, 1670, 1448, 1380, 1262, 1146, 950 Mass spectrum m/z (%): 298 (M+)

EXAMPLE 27

(1S, 4aS, 7R, 7aR)-4-(acetoxymethyl)-1-[1(ethoxy)ethoxy]-1,4a,5,6,7,7a-hexahydro-7-methylcyclopenta[c]pyran (65 mg, 0.00024 mol) obtained in Example 26 was dissolved in 3 ml of ethyl acetate, and 0.05 ml of pyridine and 10% palladium carbon (3 mg) were added. The reaction mixture was stirred for 24 hours in a hydrogen gas atmosphere of 1 atm. After the catalyst was removed by celite filtration, concentration was effected. The residual matter was purified by chromatography using silica gel, and the solvent of the fraction obtained from hexane:ether=8:2 eluent was distilled off. A colorless oily substance was thus obtained, i.e., (1S, 4aS, 7R, 7aR)-1-[1-(ethoxy)ethoxy]-1,4a,5,6,7,7a-hexahydro-4, 7-dimethylcyclopenta[c]pyran (43 mg, yield=82%). This (1S, 4aS, 7R, 7aR)-1-[1-(ethoxy)ethoxy]-1,4a,5,6,7,7a-hexahydro-4,7-dimethylcyclopenta[c]pyran had the following physicochemical properties:

Proton NMR spectrum (δ ppm in CDCl$_3$): 1.04 (3H, d, J=9 Hz), 1.17–1.26 (3H, m), 1.29–1.36 (3H, m), 1.52 (3H, brs), 1.42–2.60 (7H, m), 3.12–3.88 (2H, m), 4.90–5.02 (1H, m), 5.06 (1H, d, J=3 Hz), 5.94 (1H, brs)

EXAMPLE 28

2-[(1S, 2R, 3S)-2-(hydroxymethyl)-3-methylcyclopent-1-yl]-2-propen-1-ol (1.5 g, 0.0082 mol) obtained in Definite Example 46 was dissolved in 20 ml of dichloromethane and 10 ml of 2, 2-dimethoxypropane was added. Furthermore, 50 mg of p-toluenesulfonic acid was added, and the reaction mixture was stirred at room temperature for 24 hours. After 100 ml of dichloromethane was added, washing was carried out with a mixed aqueous solution of saturated sodium bicarbonate solution (20 ml) and saturated sodium chloride solution (20 ml), and this organic layer was dried by adding magnesium sulfate, and was filtered and then concentrated under a reduced pressure. The residual matter was purified by chromatography using silica gel, and the solvent of the fraction obtained from hexane:ether=8:2 eluent was distilled off. A colorless oily substance was thus obtained, i.e., (1R, 8S, 11S)-4,4,11-trimethyl-7-methylene-3,5-dioxabicyclo[6.3.0]undecane (550 mg, yield=29.7%). This (1R, 8S, 11S)-4,4,11-trimethyl-7-methylene-3, 5-dioxabicyclo[6.3.0]undecane had the following physicochemical properties:

Proton NMR spectrum (δ ppm in CDCl$_3$): 0.82–2.10 (6H, m), 1.01 (3H, s), 1.34 (3H, s), 1.39 (3H, s), 2.80 (1H, q, J=8 Hz), 3.36–3.55 (2H, m), 4.01 (2H, q, Jab=12 Hz), 4.87 (1H, S) 5.00 (1H, s), Mass spectrum m/z (%): 210 (M+)

EXAMPLE 29

2-[(1S, 2R, 3S)-2-(hydroxymethyl)-3-methylcyclopent-1-yl]-2-propen-1-ol (900 mg, 0.0053 mol) was dissolved in 10 ml of dichloromethane, and 5.5 ml (0.053 mol) of ethyl vinyl ether and 50 mg of pyridinium p-toluenesulfonate were added. The reaction mixture was stirred at room temperature. The reaction mixture was then poured into 50 ml of ethyl acetate, and the organic layer was washed with a mixed aqueous solution of 10 ml of saturated sodium bicarbonate solution and 20 ml of saturated sodium chloride solution, was dried by adding magnesium sulfate, and was filtered and then concentrated under a reduced pressure. The residual matter was purified by chromatography using silica gel, and the solvent of the fraction obtained from hexane:ether=1:1 eluent was distilled off. A colorless oily substance was thus obtained, i.e., 2-[(1S, 2R, 3S)-2-[[1-(ethoxy)ethoxy]methyl]-3-cyclopent-1-yl]-1-[1-(ethoxy)ethoxyl]propane (1.030 g, yield=61.0%). This 2-[(1S, 2R, 2S)-2-[[1-(ethoxy)ethoxy]methyl]-3-cyclopent-1-yl]-1-[1-(ethoxy)ethoxyl]propane had the following physicochemical properties:

Proton NMR spectrum (δ ppm in CDCl$_3$): 1.04 (3H, d, J=6 Hz), 1.08–1.40 (12H, m), 1.52–2.02 (7H, m), 2.64 (1H, q), 3.00–3.72 (6H, m), 4.48–4.66 (1H, m), 4.66–4.87 (1H, brs), 5.12 (1H, brs) Mass spectrum m/z (%): 319 (M+H)+

EXAMPLE 30

2-[(1S, 2R, 3S)-2-(hydroxymethyl)-3-methylcyclopent-1-yl]-2-propen-1-ol (200 mg, 0.0012 mol) obtained in Definite EXAMPLE 46 was dissolved in 8 ml of anhydrous tetrahydrofuran, and while the reaction mixture was being cooled with ice and stirred, 1.47 ml of borane-dimethyl sulfide complex (2.0M tetrahydrofuran solution) was added dropwise. The reaction mixture was then stirred for 3 hours. After 5 ml of ethanol and 1 ml of 3N aqueous sodium hydroxide solution were added sequentially, the reaction mixture was again cooled with ice, and 1.0 ml of 30% hydrogen peroxide solution was added dropwise. Immediately thereafter, the reaction solution was heated to 80° C. and was further stirred for 1 hour. The reaction mixture was poured into iced water and extraction was carried out using ethyl acetate (50×3). The organic layers were Joined, dried by adding magnesium sulfate, filtered and then concentrated under a reduced pressure. The residual matter was purified by chromatography using silica gel, and the solvent of the fraction obtained from ethyl acetate:ether=3:1 eluent was distilled off. A colorless oily substance was thus obtained, i.e., 2-[(1S, 2R, 3S)-2-(hydroxy-methyl)-3-methylcyclopent-1-yl]-propane-1, 3-diol (150 mg, yield=67.8%). This 2-[(1S, 2R, 3S)-2-(hydroxymethyl)-3-methylcyclopent-1-yl]-propane-1,3-diol had the following physicochemical properties:

Proton NMR spectrum (δ ppm in CDCl$_3$): 1.00 (3H, d, J=7 Hz), 1.02–1.44 (2H, m), 1.62–2.04 (6H, m), 3.16–3.95 (6H, m), 4.20 (3H, brs)

EXAMPLE 31

2-[(1S, 2R, 3R)-2-(hydroxymethyl)-3-methylcyclopent-1-yl]-2-propen-1-ol (200 mg, 0.0021 mol) obtained in Definite Example 47 was dissolved in a mixed solvent of chloroform (4 ml) and water (4 ml), and after benzalkonium chloride (450 mg) was added, magnesium monoperoxyphthalate (1.45 g, 0.0024 mol) was added. The reaction mixture was then stirred at room temperature for 12 hours. After insoluble matters of the reaction mixture solution were removed by celite filtration, the aqueous layer was extracted by chloroform (50×2). The organic layer was dried by adding magnesium sulfate, was filtered and was thereafter concentrated under a reduced pressure. The residual matter was purified by chromatography using silica gel, and the solvent of the solvent obtained from ether:ethyl acetate=8:2 eluent was distilled off, and the residue was recrystalized from ether hexane. A colorless needle-like crystal was thus obtained, i.e., 2-[(1S, 2R, 3R)-2-(hydroxymethyl)-3-methylcyclopent-1-yl]-2, 3-epoxypropane-1-ol (109 mg, yield=50%). This 2-[(1S, 2R, 3R)-2-(hydroxymethyl)-3-methylcyclopent-1-yl]-2, 3-epoxypropane-1-ol had the following physicochemical properties:

Proton NMR spectrum (δ ppm in CDCl$_3$): 0.98 (3H, d, J=7 Hz), 1.08-2.96 (7H, m), 3.40-3.96 (6H, m)

EXAMPLE 32

2-[(1S, 2R, 3R)-2-(hydroxymethyl)-3-methylcyclopent-1-yl]-2-propen-1-ol (100 mg, 0.00059 mol) obtained in Definite Example 47 was dissolved in 3 ml of dichloromethane, and after 2 ml of 2,2-dimethoxypropane was added, 5 mg of p-toluenesulfonic acid wad added. The reaction mixture was stirred at room temperature for 12 hours. The reaction mixture was poured into 50 ml of ethyl acetate, and organic layer was washed with a mixed aqueous solution of saturated sodium bicarbonate solution (10 ml) and saturated sodium chloride solution (20 ml), was dried by adding magnesium sulfate, was filtered and was thereafter concentrated under a reduced pressure. The residual matter was purified by chromatography using silica gel, and the solvent of the fraction obtained from hexane:ether=9:1 eluent was distilled off. A colorless oily substance was thus obtained, i.e., (1R, 8S, 11R)-4,4,11-trimethyl-7-methylene-3,5-dioxabicyclo[6.3.0]undecane (108 mg, yield=87.4%). This (1R, 8S, 11R)-4,4,11-trimethyl-7-methylene-3,5-dioxabicyclo[6,3,0]undecane had the following physicochemical properties:

Proton NMR spectrum (δ ppm in CDCl$_3$): 0.93 (3H, s), 1.33 (3H, s) 1.41 (3H, s), 1.60-3.04 (7H, m), 3.38-3.76 (2H, m), 4.18 (2H, d, J=7 Hz), 4.84 (1H, s), 4.88 (1H, s) Mass spectrum m/z (%): 211 (M+)

EXAMPLE 33

2-[(1S, 2R, 3R)-2-(hydroxymethyl)-3-methylcyclopent-1-yl]-2-propen-1-ol (200 mg, 0.0012 mol) obtained in Definite Example 47 was dissolved in 8 ml of anhydrous tetrahydrofuran, and while the reaction mixture was being cooled by ice and stirred, 1.47 ml of borane-dimethyl sulfide complex (2.0M tetrahydrofuran solution) was added dropwise. After the reaction mixture was stirred for 3 hours, 5 ml of ethanol was added. The reaction mixture was again cooled by ice and after 1.0 ml of 30% hydrogen peroxide solution was added dropwise, the reaction mixture was refluxed at 80° C. One hour later, the reaction mixture was poured into ice water and extraction was made using ethyl acetate (50 ml×3). The organic layers were joined, dried by adding magnesium sulfate, filtered and thereafter concentrated under a reduced pressure. Since the residual substance (166 mg, yield=75.0%) had the following physicochemical properties, it was determined to be 2-[(1S, 2R, 3R)-2-(hydroxymethyl)-3-methylcyclopent-1-yl]-propane-1,3-diol.

Proton NMR spectrum (δ ppm in CDCl$_3$): 1.03 (3H, d, J=7 Hz), 1.04-1.48 (2H, m), 1.60-2.12 (8H, m), 3.48-3.96 (6H, m), 4.12 (3H, brs) Mass spectrum m/z (%): 189 (M+H)+

EXAMPLE 34

2-[(1R, 2R, 3S)-2-(hydoxymethyl)-3-methylcyclopent-1-yl]ethan-1-ol (40 mg, 0.0002 mol) obtained in Definite Example 48 was dissolved in 1 ml of dichloromethane, and 0.1 ml of pyridine and 0.1 ml of acetic anhydride were sequentially added. After 5 mg of N, N-dimethylaminopyridine was finally added, the reaction mixture solution was stirred at room temperature for 4 hours. Then, the reaction mixture solution was poured into 30 ml of ethyl acetate, and the organic layer washed with 2N hydrochloric acid solution (10 ml), saturated sodium bicarbonate solution (10 ml) and saturated sodium chloride solution (10 ml) was dried by adding magnesium sulfate, filtered, and thereafter concentrated under a reduced pressure. The residual matter was purified by chromatography using silica gel, and the solvent of the fraction obtained from hexane:ether=1:1 eluent was distilled off. A colorless oily substance was thus obtained, i.e., 2-[(1R, 2R, 3S)-2-(acetoxymethyl)-3-methylcyclopent-1-yl]-ethyl-1-acetate (57.6 mg, yield=86.2%). This 2-[(1R, 2R, 3S)-2-(acetoxymethyl)-3-methylcyclopent-1-yl]-ethyl-1-acetate had the following physicochemical properties:

Proton NMR spectrum (δ ppm in CDCl$_3$): 1.02 (3H, d, J=6 Hz), 0.98-1.52 (4H, m), 1.68-1.92 (5H, m), 2.04 (3H, s), 2.05 (3H, s), 4.01-4.13 (4H, m) Mass spectrum m/z (%): 243 (M+H)+

Next, definite examples of the iridoid compounds will be given. The compounds illustrated below are all known compounds.

DEFINITE EXAMPLE 1

50.1 g of genipoxide was suspended in 300 ml of dichloromethane, and 63 ml of pyridine, 73 ml of acetic anhydride and 1.5 g of 4-dimethylaminopyridine were added. After the reaction mixture was stirred at room temperature for 17 hours, the reaction solution was transferred to a separating funnel and was washed with 500 ml of 2N hydrochloric acid solution, 300 ml of water and 300 ml of saturated aqueous sodium hydrogencarbonate solution. After drying was carried out using magnesium sulfuric anhydride, the solvent was distilled off to obtain 80 g of a residue. The residue was recrystallized from ethyl acetate-hexane, and 62.2 g (yield=81%) of a colorless needle-like crystal was obtained. Since this colorless needle-like crystal had the following physicochemical properties, it was determined as methyl (1S, 4aS, 7aS)-7-(acetoxymethyl)-1-(2,3,4,6-tetra-O-acetyl-β-D-glucopyranosyloxy)-1,4a,5-,7a-tetrahydrocyclopenta[c]pyran-4-carboxylate.

IR absorption spectrum υ NuJol max cm$^{-1}$: 2924, 1746, 1708, 1640, 1290, 1226, 902, 838 Proton NMR spectrum (δ ppm in CDCl$_3$): 1.98 (3H, s), 2.02 (3H, s), 2.03 (3H, s), 2.07 (3H, s), 2.09 (3H, s), 2.83 (2H, dd, J=9.17 Hz), 3.12-3.26 (1H, m), 3.72 (3H, s), 3.65-3.78 (1H, m), 4.17 (1H, dd, J=3.11 Hz), 4.23 (1H, dd, J=5.11 Hz), 4.70 (2H, brs), 4.86 (1H, d, J=8 Hz), 4.96-5.28 (4H, m), 5.83 (1H, br), 7.42 (1H, d, J=1 Hz)

DEFINITE EXAMPLE 2

0.93 g of methyl (1S, 4aS, 7aS)-7-(acetoxymethyl)-1-(2,3,4,6-tetra-O-acetyl-β-D-glucopyranosyloxy)-1,4a,5-,7a-tetrahydrocyclopenta[c]pyran-4-carboxylate obtained in Definite Example 1 was dissolved in a mixed solvent of 5 ml of ethyl acetate and 5 ml of methanol. After 13 mg of palladium carbon was added, the reaction mixture was stirred at room temperature for 24 hours.

After 10% palladium carbon was removed by filtration, the filtrate was concentrated to obtain 0.93 g of a colorless oily substance. This substance was purified by column chromatography (40 g of silica gel, ethyl acetate:hexane=1:2), and fractions A and B were obtained. When the solution of the fraction A was distilled off, there was obtained 0.64 g of a colorless solid (yield=62.4 %). Furthermore, this solid was recrystallized from ether and hexane, and a colorless needle-like crystal was obtained. Since this colorless needle-like crystal had the following physicochemical properties, it was determined to be methyl (1S, 4aS, 7S, 7aR)-1-(2,3,4,6-tetra-O-acetyl-β-D-glucopyranosyloxy)-1,4a,5,6,7,7a-hexahydro-7-methylcyclopenta[c]pyran-4-carboxylate.

melting point: 110.0°–111.0° C. IR absorption spectrum υ Nujol max cm⁻¹: 2935, 1750, 1712, 1650, 1238 Proton NMR spectrum (δ ppm in CDCl$_3$): 1.06 (3H, d, J=6 Hz), 1.10–1.33 (2H, m), 1.37–1.56 (1H, m), 1.64–2.26 (3H, m), 1.93 (3H, s), 2.00 (3H, S), 2.03 (3H, s), 2.09 (3H, s), 2.78–2.94 (1H, m), 3.70 (3H, s), 3.64–3.82 (1H, m), 4.15 (1H, dd, J=3.12 Hz), 4.30 (1H, dd, J=5.12 Hz), 4.86 (1H, d, J=8 Hz), 4.92–5.30 (4H, m), 7.30 (1H, s)

When the solvent was distilled off from the fraction B, 0.22 g of a colorless solid (yield=23.6%) was obtained. Since this colorless solid had the following physicochemical properties, it was determined to be methyl (1S, 4aS, 7S, 7aS)-7-(acetoxymethyl)-1-(2,3,4,6-tetra-O-acetyl-β-D-glucopyranosyloxy)-1,4a,5,6,7,7a-hexahydrocyclopenta[c]pyran-4-carboxylate.

IR absorption spectrum υ NuJol max cm⁻¹: 2920, 1750, 1705, 1638 Proton NMR spectrum δ ppm in CDCl$_3$): 1.26–1.43 (1H, m), 1.48–2.23 (5H, m), 1.94 (3H, s), 2.01 (3H, s), 2.03 (3H, s), 2.06 (3H, s), 2.09 (3H, s), 2.80–2.93 (1H, m), 3.71 (3H, s), 3.62–3.77 (1H, m), 4.04 (2H, dd, J=2.6 Hz), 4.15 (1H, dd, J=3.10 Hz), 4.26 (1H, dd, J=5.10 Hz), 4.85 (1H, d, J=8 Hz), 4.95–5.28 (4H, m), 7.37 (1H, d, J=1 Hz)

DEFINITE EXAMPLE 3

Methyl (1S, 4aS, 7S, 7aR)-1-(2,3,4,6-tetra-O-acetyl-β-D-glucopyranosyloxy)-1,4a,5,6,7a-hexahydro-7-methylcyclopenta[c]pyran-4-carboxylate (3.03 g) obtained in Definite Example 2 was dissolved in 30 ml of methanol, and after 7.5 mg of potassium carbonate was added, the reaction mixture was stirred at room temperature for 15 hours. After insoluble matters were removed by filtration, the filtrate was concentrated, and the residue was dissolved in ether. Then, a colorless solid precipitated immediately. The solid was collected by filtration to give 1.96 g of a colorless solid (yield 94%). When this colorless solid was further recrystallized from methanol. A colorless prismatic crystal was obtained. Since this colorless prismatic crystal had the following physicochemical properties, it was determined to be methyl (1S, 4aS, 7S, 7aR)-1-(β-D-glucopyranosyloxy)-1,4a,5,6,7,7a-hexahydro-7-methylcyclopenta[c]pyran-4-carboxylate.

melting point: 162°–163° C. elementary analysis: calculated: C: 54.54 H: 7.00 found: C: 54.69 H: 7.12 IR absorption spectrum υ NuJol max cm⁻¹: 3368, 2952, 2904, 2872, 1686, 1642, 1444 Proton NMR spectrum (δ ppm in CD3OD): 1.09 (3H, d, J=7 Hz), 1.12–1.48 (2H, m), 1.68–2.30 (4H, m), 2.90 (1H, q, J=8 Hz), 3.69 (3H, s), 3.12–3.45 (4H, m), 3.60–3.76 (1H, m), 3.91 (1H, d, J=12 Hz), 4.66 (1H, d, J=8 Hz), 5.22 (1H, d, J=6 Hz), 7.41 (1H, d, J=1 Hz)

DEFINITE EXAMPLE 4

21 g of methyl (1S, 4aS, 7S, 7aR)-1-(β-D-glucopyranosyloxy)-1,4a,5,6,7,7a-hexahydro-7-methylcyclopenta[c]pyran-4-carboxylate obtained in Definite Example 3 was dissolved in 160 ml of water, and after 26.4 g of sodium periodate was added, the reaction mixture was stirred at room temperature for 2 hours. This solution was cooled by ice, and after 10.7 g of sodium boron hydride was added, the solution was further stirred at room temperature for 2 hours. Subsequently, 70.4 ml of 6N hydrochloric acid solution and 300 ml of ether were added, and the reaction mixture was stirred at room temperature for 2.5 hours. Next, 20 g of sodium hydrogen sulfite and 30 g of sodium chloride were added, the reaction mixture was stirred for 30 minutes, and then the ether layer was separated. The aqueous layer was further extracted by ether (300 ml×3) and joined with the ether layer obtained previously, and was thereafter dried by adding anhydrous magnesium sulfate. After filtration, the filtrate was concentrated to give 9.5 g of a yellow oily substance. This substance was subjected to column chromatography using silica gel (ether:hexane=1:1) to obtain 8.91 g (yield=81%) of a colorless oily substance. Since this colorless oily substance had the following physicochemical properties, it was determined as methyl (4aS, 7S, 7aR)-1,4a,5,6,7,7a-hexahydro-1-hydroxy-7-methylcyclopenta[c]pyran-4-carboxylate.

IR absorption spectrum υ neat max cm⁻¹: 3412, 1705, 1686, 1628, 1440 Proton NMR spectrum (δ ppm in CDCl$_3$): 1.10 (3H, d, J=7 Hz), 1.15–1.37 (2H, m), 1.58–1.67 (1H, m), 1.89–2.10 (2H, m), 2.22–2.28 (1H, m), 2.60–3.20 (1H, br), 2.86 (1H, q, J8 Hz), 3.71 (3H, s), 4.89 (1H, d, J7 Hz), 7.41 (1H, d, J=1 Hz) Mass spectrum m/Z (%): 2.12 (M+)

DEFINITE EXAMPLE 5

5.5 g of pyridinium chlorochromate was dissolved in 40 ml of dichloromethane, and after 5.5 g of a molecular sieve 3 Å was added, the reaction mixture was stirred at room temperature for 5 minutes. 10 ml of a dichloromethane solution of 1.06 g of methyl (4aS, 7S, 7aR)-1,4a,5,6,7,7a-hexahydro-1-hydroxy-7methylcyclopenta[c]pyran-4-carboxylate obtained in Definite Example 4 was added, and the reaction mixture was stirred at room temperature for 30 minutes. After 100 ml of ether and 100 ml of hexane were added, the mixture was filtered by the use of a column of silica gel (silica gel=200 g). The filtrate was concentrated under a reduced pressure to give 0.87 g of a colorless solid (yield=83%). This colorless solid was further recrystallized from hexane to give a colorless prismatic crystal. Since this colorless prismatic crystal had the following physicochemical properties, it was determined as methyl (4aS, 7S, 7aR)-1,4a,5,6,7,7a-hexahydro-7-methyl-1-oxocyclopenta[c]pyran-4-carboxylate.

Melting point: 40°–41.5° C.
Specific rotation: [α]26 D+79.79° (c=0.97, CHCl$_3$) IR absorption spectrum υ NuJol max cm⁻¹: 2956, 1778, 1710, 1652, 1440, 1284, 1168, 1036 Proton NMR spectrum δ ppm in CDCl$_3$): 1.21 (3H, d, J6 Hz), 1.30–1.55 (2H, m), 1.88–2.05 (1H, m), 2.16–2.41 (1H, m), 2.44–2.65 (2H, m), 3.16 (1H, q, J=8 Hz), 3.77 (3H, s), 7.43 (1H, s) Mass spectrum m/z(%): 210 (M+) Elementary analysis: calculated C: 62.84 H: 6.71 found C: 62.71 H: 6.71

DEFINITE EXAMPLE 6

10 g of methyl (1S, 4aS, 7S, 7aS)-7-(acetoxymethyl)-1-(2,3,4,6-tetra-O-actyl-β-D-glucopyranosyloxy)-1,4a,5,6,7,7a-hexahydrocyclopenta[c]pyran-4-carboxylate obtained in Definite Example 2 was dissolved in methanol, and after 10 ml of potassium carbonate was added, the reaction mixture was stirred at room temperature for 20 hours. The solvent of the reaction mixture was distilled off and 6.5 g of the resulting methyl (1S, 4aS, 7S, 7aS)-1-(β-D-glucopyranosyloxy)-1,4a,5,6,7,7a-hexahydro-7-(hydroxymethyl)cyclopenta[c]pyran-4- carboxylate was dissolved in 60 ml of water, and after 7.85 g of sodium periodate was added, the reaction mixture was stirred at room temperature for 2 hours. Next, while the reaction solution was being cooled by ice and stirred, 3.17 g of sodium boron hydride was added. After the temperature was returned to the room temperature, the reaction mixture was stirred for 2 hours. Furthermore, this solution was again cooled by ice, and 25 ml of 6N hydrochloric acid solution and 100 ml of ether were simultaneously added. Then, the reaction mixture solution was stirred at room temperature. Four hours later, excess sodium chloride and sodium hydrogen sulfite were added, and the reaction mixture was added for 20 hours. Extraction was then carried out by ether (150 ml×3). The solvent of the ether layer dried by anhydrous magnesium sulfate was distilled under a reduced pressure and the resulting residue was purified by column chromatography using 100 g of silica gel. The solvent of the fraction obtained from hexane:ether (7:3) eluent was distilled to give 22.7 g of a colorless oily substance (yield=71.1%). Since this colorless oily substance had the following physicochemical properties, it was determined as methyl (4aS, 7S, 7aS)-1,4a,5,6,7,7a-hexahydro-1-hydroxy-7-(hydroxymethyl)cyclopenta[c]pyran-4-carboxylate.

IR absorption spectrum υ neat max cm$^{-1}$: 3412, 1688, 1628, 1440

Specific rotation: $[α]26D-7.05°$ (c=0.99, MeOH) Proton NMR spectrum (δ ppm in CDCl$_3$): 1.17–1.32 (2H, m), 1.85–1.93 (2H, m), 2.06–2.48 (2H, m), 2.65–2.84 (0.5H, m), 3.16–3.27 (0.5H, m), 3.30–3.64 (1H, m), 3.70 (1.5H, s), 3.72 (1.5H, s), 3.72–3.86 (1H, m), 4.70 (0.5H, d, J=8 Hz), 5.18 (0.5 H, s), 5.53 (1H, br), 7.17 (1H, br), 7.45 (0.5H, s), 7.50 (0.5H, d, J=1 Hz) Mass spectrum m/z (%): 228 (M+)

DEFINITE EXAMPLE 7

220 mg of methyl (1S, 4aS, 7aS)-7-(acetoxymethyl)-1-(2,3,4,6-tetra-O-acetyl-β-D-glucopyranosyloxy)-1,4a,5,,7a-tetrahydrocyclopenta[c]pyran-4-carboxylate obtained in Definite Example 1 was dissolved in 5 ml of ethyl acetate, and after 6.5 mg of palladium chloride was 10 added, the reaction mixture was stirred at room temperature for 19 hours under a hydrogen atmosphere of 1 atm. After insoluble matters were filtered, the filtrate was concentrated to give 270 mg of a colorless oily matter. The resulting oily matter was purified by column chromatography (silica gel 10 g, ether:benzene=1:4) to give 180 mg of a colorless solid (yield=91%). Furthermore, this colorless solid was recrystallized from ethyl acetate-hexane to give a colorless needle-like crystal. Since this colorless needle-like crystal had the following physicochemical properties, it was determined as methyl (1S, 4aS, 7aS)-1-(2,3,4,6-tetra-O-acetyl-β-D-glucopyranosyloxy)-1,4a, 5,7a-tetrahydro-7-methylcyclopenta[c]pyran-4-carboxylate.

Melting point: 116°–117° C. IR absorption spectrum υ NuJol max cm$^{-1}$: 2930, 1758, 1750, 1710, 1642 Proton NMR spectrum (δ ppm in CDCl$_3$): 1.77 (3H, s), 1.93–2.19 (1H, m), 1.97 (3H, s), 2.01 (3H, s), 2.03 (3H, s), 2.08(3H, s), 3.73 (2H, m), 3.12–3.15 (1H, m), 3.70 (3H, s), 3.60–3.81 (1H, m), 4.13 (1H, dd, J=3.12 Hz), 4.28 (1H, dd, J=5.12 Hz), 4.86 (1H, d, J=8 Hz), 4.98–5.24 (4H, m), 5.45 (1H, brs), 7.39 (1H, d, J=1Hz)

DEFINITE EXAMPLE 8

2.43 g of methyl (1S, 4aS, 7aS)-1-(2,3,4,6-tetra-O-acetyl-β-D-glucopyranosyloxy)-1,4a,5,7a-tetrahydro-7-methylcyclopenta[c]pyran-4-carboxylate obtained in Definite Example 7 was dissolved in 40 ml of methanol, and after 10 mg of potassium carbonate was added, the reaction mixture was stirred at room temperature for 5 hours. After insoluble matters were filtered, the filtrate was concentrated. After ether was added to the residue, insoluble matters were filtered and collected to give 1.65 g of a colorless solid (yield=99%). Furthermore, this colorless solid was recrystallized from methanol-ether to give a colorless prismatic crystal. Since this colorless prismatic crystal had the following physicochemical properties, it was determined as methyl (1S, 4aS, 7aS)-1-(β-D-glucopyranosyloxy)-1,4a,5,7a-tetrahydro-7-methylcyclopenta[c]pyran-4-carboxylate.

Melting point: 170°–172° C. Specific rotation: $[α]26D-13.72°$ (c=1.00, MeOH) Elementary analysis: calculated C: 54.83 H: 6.50 found C: 54.62 H: 6.50

IR absorption spectrum υ KBr max cm$^{-1}$: 3556, 3392, 2916, 1716, 1640, 1438, 1378, 1292, 1076 Proton NMR spectrum (δ ppm in CD$_3$OD): 1.81 (3H, s), 1.93–2.17 (1H, m), 2.52–2.84 (3H, m), 3.04–3.50 (4H, m), 3.70 (3H, s), 3.58–3.80 (1H, m), 3.90 (1H, d, J=11 Hz), 4.61(1H, d, J=8 Hz), 5.25 (1H, d, J=6 Hz), 5.49 (1H, br), 7.47 (1H, d, J=1Hz),

DEFINITE EXAMPLE 9

7.8 g of methyl (1S, 4aS, 7aS)-1-(β-D-glucopyranosyloxy)-1,4a,5,7a-tetrahydro-7-methycyclopenta[c]pyran-4-carboxylate was dissolved in 65 ml of water, and after 9.9 g of sodium periodate was added, the reaction mixture was stirred at room temperature for 2 hours. Next, while the reaction mixture was being cooled by ice and stirred, 4.0 g of sodium borohydride was added, the temperature was returned to room temperature and the reaction mixture was stirred for 2 hours. Subsequently, 26 ml of 6N hydrochloric acid solution and 150 ml of ether were added, the reaction mixture was stirred at room temperature for 4 hours. Furthermore, 10 g of sodium hydrogen sulfite and 10 g of sodium chloride were added and after the reaction mixture was stirred for 30 minutes, the ether layer was separated. The aqueous layer was further extracted by ether (300 ml×4), was joined with the ether layer obtained previously, and was dried by anhydrous magnesium sulfate. After filtration, the filtrate was concentrated to give 4.0 g of a yellow oily matter. This oily matter was subjected to column chromatography using 100 g of silica gel (ether:hexane=1:1) to give 3.30 g of a colorless oily substance (yield=75%). Since this colorless oily substance had the following physicochemical properties, it was determined as methyl (4aS, 7aS)-1,4a,5,7a-tetrahydro-1-hydroxy-7-methylcyclopenta[c]pyran-4-carboxylate.

IR absorption spectrum υ neat max cm$^{-1}$: 3416, 1680, 1630, 1440 Specific rotation: $[α]26D-110.30°$ (c=1.01, MeOH) Proton NMR spectrum (δ ppm in CDCl$_3$): 1.86 (3H, s), 1.81–2.06 (1H, m), 2.38 (1H, t, J=8 Hz), 2.77–2.85 (1H, m), 3.16 (1H, q, J=8 Hz), 3.72 (3H, s), 4.18 (1H, br), 4.87 (1H, d, J=8 Hz), 5.54 (1H, brs), 7.50 (1H, s) Mass spectrum m/z (%): 210 (M+)

DEFINITE EXAMPLE 10

300 ml of dimethylformamide solution of 20.0 g of methyl (1S, 4aS, 7aS)-1-(β-D-glucopyranosyloxy)-1,4a,5,7a, tetrahydro-7-methylcyclopenta[c]pyran-4-carboxylate obtained in Definite Example 8 was cooled by ice and while the solution was being stirred, 17.2 g of sodium hydride (60% in oil) was added. After the reaction solution was stirred for 30 minutes while being cooled by ice, 26.6 ml of methyl iodide was added and the reaction mixture was further stirred at room temperature for 2 hours. The reaction mixture was again cooled by ice and 2N hydrochloric acid solution was added so as to adjust the pH of the solution to 2. Extraction was then carried out using ethyl acetate (50 me×3). The Joined organic layer was washed with 50 ml of water, 50 ml of aqueous sodium thiosulfate solution and 50 ml of saturated sodium chloride solution, and was then dried by adding anhydrous magnesium sulfate. After filtration, the solvent was distilled off under a reduced pressure, and 50 g of the resulting residue was purified by column chromatography (silica gel 200 g: ethyl acetate:hexane=1:2) to give 23.0 g of a colorless oily substance (yield=98%). Since this colorless oily substance had the following physicochemical properties, it was determined as methyl (1S, 4aS, 7aS)-1,4a,5-,7a-tetrahydro-7-methyl-1-(2,3,4,6-tetra-O-methyl-$\beta$-D-glucopyranosyloxy)cyclopenta[c]pyran-4-carboxylate.

IR absorption spectrum $v$ neat max cm$^-$: 2936, 2840, 1702, 1638, 1438, 1286, 1092, 996, 898

Specific rotation: [$\alpha$]26D$-$11.93° (c=1.00, MeOH) Proton NMR spectrum ($\delta$ ppm in CDCl$_3$): 1.78 (3H, s), 2.04–2.24 (1H, m), 2.65–2.87 (2H, m), 2.95–3.09 (1H, m), 3.12–3.36 (4H, m), 3.40–3.80 (2H, m), 3.40 (3H, s), 3.49 (3H, s), 3.53 (3H, s), 3.62 (3H, s), 3.70 (3H, s), 4.62 (1H, d, J=8 Hz), 5.27 (1H, d, J=5 Hz), 5.44 (1H, brs), 7.45 (1H, s)

DEFINITE EXAMPLE 11

2.0 g of methyl (1S, 4aS, 7aS)-7-(acetoxymethyl)-1-(2,3,4,6-tetra-O-acetyl-$\beta$-D-glucopyranosyloxy)-1,4a,5-,7a-tetrahydrocyclopenta[c]pyran-4-carboxylate obtained in Definite Example 1 was dissolved in 50 ml of tetrahydrofuran, and 2.0 g of ammonium formate and 65 mg of bis(triphenylphosphine)palladium chloride were added. The reaction mixture was then refluxed for 25 hours. The solvent was distilled off under a reduced pressure, and the residue was dissolved in 50 ml of ethyl acetate. It was then washed with 30 ml of water, 50 ml of a saturated aqueous sodium hydrogen carbonate solution and 50 ml of sodium chloride solution, and was dried by adding anhydrous magnesium sulfate. After filtration, the solvent was distilled off under a reduced pressure, and the resulting residue was recrystallized from ethyl acetate-hexane to give 1.7 g of a colorless needle-like crystal (yield=94%). Since this colorless needle-like crystal had the following physicochemical properties, it was determined as methyl (1S, 4aS, 7aS)-1-(2,3,4,6-tetra-O-acetyl-$\beta$-D-glucopyranosyloxy)-1,4a,5,6,7,7a-hexahydro-7-methylene-cyclopenta[c]pyran-4-carboxylate.

IR absorption spectrum $v$ KBr max cm$^{-1}$: 2950, 1756, 1704, 1636, 1224, 1042 Proton NMR spectrum $\delta$ ppm in CDCl$_3$): 1.93 (3H, s), 2.01 (3H, s), 2.03 (3H, s), 2.10 (3H, s), 1.84–2.17 (2H, m), 2.24–2.38 (2H, m), 2.80–2.94 (1H, m), 2.96–3.07 (1H, m), 3.71 (3H, s), 3.71–3.82 (1H, m), 4.16 (1H, dd, J=2, 12 Hz), 4.29 (1H, dd, J=5, 12 Hz), 4.87 (1H, d, J=8 Hz), 4.97–5.28 (5H, m), 5.34 (1H, d, J=4 Hz), 7.39 (1H, d, J=1 Hz),

DEFINITE EXAMPLE 12

1.03 g of methyl (1S, 4aS, 7aS)-7-(acetoxymethyl)-1-(2,3,4,6-tetra-O-acetyl-$\beta$-D-glucopyranosiloxy)-1,4a,5-,7a-tetrahydrocyclopenta[c]pyran-4-carboxylate obtained in Definite Example 1 was dissolved in a mixed solvent of 20 ml of methanol and 5 ml of ethyl acetate, and after 6.3 mg of palladium hydroxide was added, the reaction mixture was stirred at room temperature for 15 hours in a hydrogen atmosphere of 1 atm. Insoluble matters were removed by filtration and the filtrate was concentrated under a reduced pressure to give 1.2 g of a colorless oily matter. This colorless oily matter was purified by column chromatography (silica gel 35 g, ether:benzene=1:4) to give 0.67 g of a colorless oily matter (yield=65%). Since this colorless oily substance had the following physicochemical properties, it was determined as methyl (1S, 4aS, 7S, 7aS)-7-(acetoxymethyl)-1-(2,3,4,6-tetra-O-acetyl-$\beta$-D-glucopyranosyloxy)-1,4a,5,6,7,7a-hexahydrocyclopenta[c]pyran-4-carboxylate. From the proton NMR spectrum, the compound was found to be a 2:1 mixture of two kinds of compounds having different configurations of asymmetric carbons at the C-7 position.

Proton NMR spectrum ($\delta$ ppm in CDCl$_3$): 1.22–1.49 (1H, m), 1.49–2.23 (4H, m), 1.94 (1H, s), 1.95 (2H, s), 2.01 (3H, s), 2.03 (3H, s), 2.05 (2H, s), 2.06 (1H, S), 2.089 (1H, s), 2.094 (2H, s), 2.30–2.54 (1H, m), 2.80–2.98 (1H, m), 3.71 (3H, s), 3.63–3.80 (1H, m), 3.96–4.08 (1, 3H, m), 4.08–4.33 (2.7H, m), 4.80–5.33 (5H, m), 7.36 (1H, s) 200 mg of methyl (1S, 4aS, 7aS)-7-(acetoxymethyl)-1-(2,3,4,6-tetra-O-acetyl-$\beta$-D-glucopyranosyloxy)-1,4a,5,6,7,7a-hexahydrocyclopenta[c]pyran-4-carboxylate and methyl (1S, 4aS, 7R, 7aS)-7-(acetoxymethyl)-1-(2,3,4,6-tetra-O-acetyl-$\beta$-D-glucopyranosyloxy)-1,4a,5,6,7,7a-hexahydrocyclopenta[c]pyran-4-carboxylate were dissolved in 3 ml of methanol, and after 2 mg of potassium carbonate was added, the reaction mixture was stirred at room temperature for 24 hours. Insoluble matters were removed by filtration and the filtrate was distilled under a reduced pressure to give methyl (1S, 4aS, 7S, 7aS)-1-($\beta$-D-glycopyranosyloxy)-1,4a,5,6,7,7a-hexahydro-7-(hydroxymethyl)cyclopenta[c]pyran-4-carboxylate and methyl (1S, 4aS, 7R, 7aS)-1-($\beta$-D-glucopyranosyloxy)-1,4a,5,6,7,7a-hexahydro-7-(hydroxymethyl)cyclopenta[c]pyran-4-carboxylate as hygroscopic colorless oil substances (136 mg). The reaction products were dissolved as such in 2 ml of water without purification, and after 0.17 g of sodium periodate was added, the reaction mixture was stirred at room temperature for 1 hours. After the reaction solution was cooled by ice, 70 mg of sodium boron hydride was added and the reaction solution was further stirred at room temperature for 1 hour. After 6 ml of ether and 1.5 ml of 6N hydrochloric acid solution were added, the reaction solution was stirred at room temperature for 4 hours. Next, after 0.5 g of sodium hydrogen sulfite was added, the ether layer was separated. Furthermore, the aqueous layer was extracted by ether (10 ml×2) and the joined ether layer was dried by anhydrous magnesium sulfate. After the solvent was distilled off, 67 mg of the resulting oily matter was purified by column chromatography (silica gel 20 g, ether:hexane=1:3) to give 17 mg of a colorless solid (yield=24%) and 10 mg of a colorless oily substance (yield=13%). Since this colorless solid had the following physicochemical properties, it was determined as methyl (1S, 4aS, 7R, 7aS)-1,7-(epoxymethano)-1,4a,5,6,7,7a-hexahydrocyclopenta[c]pyran-4-carboxylate.

IR absorption spectrum $v$ KBr max cm$^{-1}$: 2960, 2880, 1706, 1696, 1648, 1442, 1270, 1076, 986, 962, 812 Proton NMR spectrum ($\delta$ ppm in CDCl$_3$): 1.38–1.83 (3H, m), 2.11–2.23 (1H, m), 2.68–2.98 (3H, m), 3.62 (1H, dd, J=9, 5 Hz), 3.73 (3H, s), 4.05 (1H, t, J=9 Hz), 5.37 (1H, d, J=5Hz), 7.53 (1H, s) Mass spectrum m/z (%): 210 (M+)

DEFINITE EXAMPLE 13

20.0 g of tert-butyldimethylsilyl chloride was added to 80 ml of a dimethylformamide solution of 15.0 g of genipin and 17.0 g of silver nitrate, and the reaction mixture was stirred at room temperature for 24 hours. After insoluble matters in the reaction mixture were removed by celite filtration, extraction was carried out using 800 ml of ethyl acetate. After the organic layer was washed twice with saturated sodium chloride solution, it was dried by anhydrous magnesium sulfate, filtered, and then concentrated under a reduced pressure. The resulting residue was dissolved in 300 ml of ethanol, and after 100 mg of pyridinium paratoluenesulfonate was added, the reaction mixture was stirred at room temperature for 24 hours. The residue after filtration of the solvent was purified by column chromatography using silica gel (300 g), and the solvent of the fraction obtained from hexane:ether (2:3) eluent was distilled off to give 5.54 g of a colorless oily substance (yield=38.8%). Since this colorless oily substance had the following physicochemical properties, it was determined as methyl (1S, 4aS, 7aS)-1-(tert-butyldimethylsilyloxy)-1,4a,5,7a-tetrahydro-7-(hydroxymethyl)cyclopenta[c]pyran-4-carboxylate.

Proton NMR spectrum ($\delta$ ppm in CDCl$_3$): 0.15 (6H, d, J=4 Hz), 0.93 (9H, s), 1.92–2.18 (2H, m), 2.60 (1H, t, J=8 Hz), 2.82–2.98 (1H, m), 3.12–3.28 (1H, m), 3.50 (1H, q, J=7 Hz), 3.73 (3H, s), 4.30 (1H, br), 4.83 (1H, d, J=8 Hz), 5.83 (1H, br), 7.50 (1H, brs)

DEFINITE EXAMPLE 14

2 ml of a dimethylformamide solution of 100 mg of methyl (1S, 4aS, 7aS)-1-(tert-butyldimethylsilyloxy)-1,4a,5,7a-tetrahydro-7-(hydroxymethyl)cyclopenta[c]pyran-4-carboxylate obtained in Definite Example 13 was added to 3 ml of a dimethylformamide suspension of 380 mg of pyridinium dichromate and 200 mg of a molecular sieve 4 Å, and the reaction mixture was stirred at room temperature for 4 hours. 30 ml of ether was added and insoluble matters in the reaction solution were filtered. The filtrate was concentrated, and the resulting residue was purified by column chromatography using a silica gel (5 g). The solvent of the fraction obtained from hexane:ether=3:7 eluent was removed by distillation to give 95 mg of a colorless oily substance (yield=91.2%). Since this colorless oily substance had the following physicochemical properties, it was determined as methyl (1S, 4aS, 7aS)-1-(tert-butyl-dimethylsilyloxy)-7-formyl-1,4a,5,7a-tetrahydrocyclopenta[c]pyran-4-carboxylate.

Proton NMR spectrum ($\delta$ ppm in CDCl$_3$): 0.02 (6H, s), 0.79 (9H, s), 2.34–3.34 (3H, m), 3.64 (3H, s), 5.32 (1H, d, J=5 Hz), 5.90 (1H, brs), 7.37 (1H, s), 9.66 (1H, d, J=1 Hz)

DEFINITE EXAMPLE 15

3.01 g of genipin was dissolved in 27 ml of dimethylformamide, and 2.19 g of tert-butyldimethylsilyl chloride and 2.4 g of imidazole were added. After the reaction mixture was stirred at room temperature for 14 hours, 200 ml of water was added and extraction with ether (100 ml×1, 75 ml×1) was carried out. The ether layers were joined, washed with water and saturated sodium chloride solution, and then dried by anhydrous magnesium sulfate. After filtration, the solvent was distilled off under a reduced pressure to give 5.98 g of a yellow oily substance. This substance was purified by column chromatography (silica gel 150 g, ether:hexane=1:4) to yield a 3.50 g of a colorless solid (yield=77.3%). Furthermore, this colorless solid was recrystallized from hexane to give a colorless needle-like crystal. Since this colorless needle-like crystal had the following physicochemical properties, it was determined as methyl (4aS, 7aS)-7-[(tert-butyldimethylsilyloxy)methyl]-1,4a,5,7a-tetrahydro-1-hydroxycyclopenta[c]pyran-4-carboxylate.

Melting point: 70°–70.5° C. Specific rotation: [α]26D+67.92° (c=0.48, CHCl$_3$) Elementary analysis: calculated C: 59.97 H: 8.29 found C: 60.05 H: 8.29 IR absorption spectrum $\nu$ KBr max cm$^{-1}$: 3416, 2948, 2856, 1712, 1632, 1440, 1276, 1202 Proton NMR spectrum ($\delta$ ppm in CDCl$_3$): 0.13 (6H, s), 0.93 (9H, s), 2.10 (1H, dd, J=8, 17 Hz), 2.48 (1H, t, J=8 Hz), 2.88 (1H, dd, J=8, 17 Hz), 3.21(1H, q, J=8 Hz), 3.73 (3H, s), 4.34 (1H, d, J=14 Hz), 4.37 (1H, d, J=14 Hz), 4.80 (1H, dd, J=3, 8 Hz), 5.43 (1H, d, J=3 Hz), 5.84 (1H, brs), 7.56 (1H, s) Mass spectrum m/z (%): 340 (M+)

DEFINITE EXAMPLE 16

10.3 g of methyl (4aS, 7aS)-7-[(tert-butyldimethylsilyloxy)methyl]-1,4a,5,7a-tetrahydro-1-hydroxycyclopenta[c]pyran-4-carboxylate obtained in Definite Example 15 was dissolved in 50 ml of dichloromethane, and after 4.65 g of dihydropyran and 150 mg of camphorsulfonic acid were added, the reaction mixture was stirred at room temperature for 5 hours. The reaction solution was washed with 50 ml of saturated aqueous sodium bicarbonate solution and was dried by anhydrous magnesium sulfate. When the solvent was distilled off, there was obtained 20.2 g of a brown oily substance. This substance was dissolved in 70 ml of tetrahydrofuran, and after 30 ml of a 1M tetrahydrofuran solution of tetra-n-butylammonium fluoride was added, the reaction solution was stirred at room temperature for 4 hours. After 150 ml of ether was added and washing with water (50 ml) was made, drying was made by anhydrous magnesium sulfate. After filtration, the solvent was distilled off and there was obtained 12.1 g of an oily substance. This substance was purified by column chromatography (silica gel 400 g, ether:hexane=1:1) to give fractions A and B. The solvent of the fraction A was distilled off to give 2.55 g of a colorless oily substance (yield=25.6%). Since this colorless oily substance had the following physicochemical properties, it was determined as methyl (1S, 4aS, 7aS)-1,4a,5,7a-tetrahydro-1-(2-tetrahydropyranoxy)-7-(hydroxymethyl)cyclopenta[c]pyran-4-carboxylate.

Proton NMR spectrum ($\delta$ ppm in CDCl$_3$): 1.38–2.00 (6H, m), 2.13 (1H, dd, J=9, 17 Hz), 2.50–2.72 (2H, m), 2.92 (1H, dd, J=9, 17 Hz), 3.21 (1H, q, J=8 Hz), 3.49–3.63 (1H, m), 3.73 (3H, s), 3.73–3.97 (1H, m), 4.29 (2H, s), 4.94 (1H, d, J=8 Hz), 5.05 (1H, d, J=3 Hz), 5.89 (1H, brs), 7.49 (1H, s) IR absorption spectrum $\nu$ CHCl$_3$ max cm$^{-1}$: 3612, 3484, 2948, 2880, 1704, 1632 Mass spectrum m/z (%): 310 (M+)

When the solvent of the fraction B was distilled off, 2.60 g of a colorless oily substance was obtained (yield=26.1%). Since this colorless oily substance had the following physicochemical properties, it was determined as methyl (1S,4aS,7aS)-1,4a,5 7a-tetrahydro-1-(2-tetrahydropyranoxy)-7-(hydroxymethyl)cyclopenta[c]pyran-4-carboxylate.

Proton NMR spectrum (δ ppm in CDCl₃): 1.50–2.46 (8H, m), 2.71 (1H, t, J=8 Hz), 2.91 (1H, dd, J=8, 16 Hz), 3.21 (1H, q, J=9 Hz), 3.54–3.69 (1H, m), 3.73 (3H, s), 4.00–4.15 (1H, m), 4.26 (2H, s), 4.78 (1H, d, J=9 Hz), 4.92 (1H, t, J=3 Hz), 5.85 (1H, brs), 7.53 (1H, d, J=1 Hz) IR absorption spectrum υ CHCl₃ max cm⁻¹: 3616, 3484, 2972, 2892, 1704, 1632 Mass spectrum m/z (%): 310 (M+)

DEFINITE EXAMPLE 17

2.55 g of methyl (1S, 4aS, 7aS)-1,4a,5,7a-tetrahydro-1-(2-tetrahydropyranosiloxy)-7-(hydroxymethyl)cyclopenta[c]pyran obtained in Definite Example 16 was dissolved in 25 ml of tetrahydrofuran, and the reaction mixture was cooled in an ice bath. After 25 ml of 1.50M toluene solution of diisobutylaluminum hydride was added, the reaction mixture was stirred for 30 minutes in the ice bath. After 5 ml of acetone, 50 ml of ether and 7 ml of water were added, the reaction mixture was stirred at room temperature for 1 hour. Insoluble matters were removed by filtration and the filtrate was concentrated to give 2.0 g of a colorless solid (yield=86.2%). Furthermore, this colorless solid was recrystallized from ethyl acetate to give a colorless needle-like crystal. Since this colorless needle-like crystal had the following physicochemical properties, it was determined as (1S, 4aS, 7aS)-4,7-bis(hydroxymethyl)-1,4a,5,7a-tetrahydro-1-(2-tetrahydropyranyloxy)cyclopenta[c]pyran.

Melting point:135.5°–136.5° C. Specific rotation: [α]26D−55.7° (c=1, 22, CHCl₃) Elementary analysis: calculated C: 63.81 H: 7.85 found C: 63.93 H: 7.95 Proton NMR spectrum (δ ppm in CDCl₃): 1.56–1.84 (6H, m), 1.20–1.40 (1H, br), 2.19 (1H, ddt, J=16, 9, 2 Hz), 2.62–2.81 (3H, m), 3.06 (1H, q, J=9 Hz), 3.51 (1H, dt, J=12, 6 Hz), 3.85 (1H, dt, J=12, 5 Hz), 4.08 (2H, s), 4.29 (2H, s), 4.82 (1H, d, J=8, 5 Hz), 5.01–5.04 (1H, m), 5.87 (1H, s), 6.42 (1H, s) IR absorption spectrum υ KBr max cm⁻¹: 3304, 2932, 1666, 1140, 1124, 1090, 1056, 1044, 1016, 972, 938, 906 Mass spectrum m/z (%): 282 (M+)

DEFINITE EXAMPLE 18

2.60 g of methyl (1S, 4aS, 7aS)-1,4a,5,7a-tetrahydro-1-(2-tetrahydropyranosyloxy)-7-(hydroxymethyl)-cyclopenta[c]pyran-4-carboxylate obtained in Definite Example 16 was dissolved in 25 ml of tetrahydrofuran, and while the reaction mixture was being stirred in an ice bath, 25 ml of a 1.50M toluene solution of diisobutylaluminum hydride was added. After the reaction mixture was stirred further for 30 minutes in the ice bath, 5 ml of acetone, 50 ml of ether and 7 ml of water were added, and the reaction mixture was stirred at room temperature for 1 hour. Insoluble matters were filtrated, and the filtrate was concentrated to give 1.95 g of a colorless solid (yield=82.4%). This colorless solid was further recrystallized from ether to give a colorless columnar crystal. Since this colorless columnar crystal had the following physicochemical properties, it was determined as (1S, 4aS, 7aS)-4,7-bis(hydroxymethyl)-1,4a,5,7a-tetrahydro-1-(2-tetrahydropyranyloxy)cyclopenta[c]pyran.

Melting point: 84°–85.5° C. Specific rotation: [α]26D+78.10° (c=1.26, CHCl₃) Elementary analysis: calculated C: 63.81 H: 7.85 found C: 63.54 H: 7.71 IR absorption spectrum υ KBr max cm⁻¹: 3350, 2932, 1680 Proton NMR spectrum (δ ppm in CDCl₃): 1.50–2.00 (8H, m), 2.15 (1H, ddt, J=9, 16, 2 Hz), 2.67–2.79 (2H, m), 3.05 (1H, q, J=9 Hz), 3.58 (1H, dt, J=10, 5 Hz), 4.07–4.12 (3H, m), 4.27 (2H, s), 4.66 (1H, d, J=9 Hz), 4.90 (1H, dd, J=3, 1.5 Hz), 5.81 (1H, s), 6.45 (1H, s) Mass spectrum m/z (%): 282 (M+)

DEFINITE EXAMPLE 19

3.50 g of pyridinium chlorochromate was dissolved in 80 ml of dichloromethane, and after 5.11 g of a molecular sieve 3 Å was added, the reaction mixture was stirred at room temperature for 5 minutes. 20 ml of dichloromethane solution of 0.93 g of methyl (4aS, 7aS)-7-[(tert-butyldimethylsilyloxy)methyl]-1,4a,5,7a-tetrahydro-1-hydroxycyclopenta[c]pyran-4-carboxylate obtained in Definite Example 15 was added to this mixture, and the reaction mixture was stirred at room temperature for 2.5 hours. After 100 ml of ether and 100 ml of hexane were added to the reaction solution, insoluble matters were removed by filtration and the filtrate was concentrated. 2.0 g of the resulting oily substance was purified by column chromatography (silica gel 30 g, ether: hexane=2:3) to give 0.65 g of a colorless solid (yield=70%). Furthermore, this colorless solid was recrystallized from hexane to give a colorless needle-like crystal. Since this colorless needle-like crystal had the following physicochemical properties, it was determined as methyl (4aS, 7aS)-7-(tert-butyldimethylsilyloxy)methyl]-1,4a,5,7a-tetrahydro-1-oxocyclopenta[c]pyran-4-carboxylate.

Melting point:42.5°–44° C. Specific rotation: [α]26D+120.1° (c=1.58, CHCl₃) IR absorption spectrum υ KBr max cm⁻¹: 3000, 2900, 1770, 1716, 1658, 1438, 1332, 1284 Proton NMR spectrum (δ ppm in CDCl₃): 0.08 (6H, s), 0.90 (9H, s), 2.21 (1H, dd, J=9, 16 Hz), 2.90 (1H, dd, J=8, 16 Hz), 3.43–3.67 (2H, m), 3.78 (3H, s), 4.45 (2H, s), 5.86 (1H, s), 7.48 (1H, s) Mass spectrum m/z (%): 338 (M+)

DEFINITE EXAMPLE 20

104 mg of methyl (4aS, 7aS)-7-[(tert-butyldimethylsilyloxy)methyl]-1,4a,5,7a-tetrahydro-1-oxocyclopenta[c]-pyran-4-carboxylate obtained in Definite Example 19 was dissolved in 1 ml of dichloromethane, and while the reaction mixture was being cooled by ice, 40 μl of a boron trifluoride-ether complex was added. After the reaction mixture was stirred for 1 hour while being cooled by ice, 2 ml of saturated sodium hydrogen carbonate was added, and extraction with ether (10 ml×3) was carried out. After the joined ether layer was washed with saturated sodium hydrogen carbonate solution, drying was made using anhydrous magnesium sulfate. After filtration, the solvent was distilled off and there was obtained 41 mg of a colorless solid (yield=59%). Since this colorless solid had the following physicochemical properties, it was determined as methyl (4aS, 7aS)-1,4a,5,7a-tetrahydro-7-(hydroxymethyl)-1-oxocyclopenta[c]pyran-4-carboxylate. Proton NMR spectrum (δ ppm in CDCl₃): 2.27 (1H, ddt, J=9, 16, 2 Hz), 2.36–2.67 (1H, br), 2.97 (1H, dd, J=9, 17 Hz), 3.46–3.63 (1H, m), 3.77–3.84 (1H, m), 3.83 (3H, s), 4.43 (2H, s), 5.92 (1H, s), 7.51 (1H, s) IR absorption spectrum υ KBr max cm⁻¹: 3524, 2952, 2856, 1768, 1714, 1658 Mass spectrum m/z (%): 224 (M+)

DEFINITE EXAMPLE 21

15.0 g of methyl (4aS, 7aS)-7-[(tert-butyldimethylsilyloxy)methyl]-1,4a,5,7a-tetrahydro-1-hydroxycyclopenta[c]pyran-4-carboxylate obtained in Definite Example 15 was dissolved in 100 ml of dichloromethane, and after 20 ml of ethyl vinyl ether and 500 mg of pyridinium para-toluenesulfonate were added, the reaction mixture was stirred at room temperature for 18 hours. The reaction solution was washed with saturated sodium hydrogen carbonate solution (50 ml) and saturated sodium chloride solution (50 ml) and was dried by anhydrous magnesium sulfate. After filtration, the solvent was distilled off to give 25.0 g of a brown oily substance. This brown oily substance was dissolved in 100 ml of tetrahydrofuran and after 90 ml of 1M tetrahydrofuran solution of tetra-n-butylammonium fluoride was added, the reaction mixture was stirred at room temperature for 4 hours. The oily substance was dissolved in 200 ml of ether, washed with water (150 ml) and then dried by anhydrous magnesium sulfate. After filtration, the solvent was distilled off, and 16.5 g of the resulting brown oily substance was purified by column chromatography (silica gel 150 g, ether:hexane=1:1) to give 5.72 g of a colorless oily substance (yield=44%). Since this colorless oily substance had the following physicochemical properties, it was determined as methyl (1s, 4aS, 7aS)-1-[1-(ethoxy)ethoxy]-1,4a,5,7a-tetrahydro-7-(hydroxymethyl)cyclopenta[c]pyran-4-carboxylate.

IR absorption spectrum υ neat max cm$^{-1}$: 3508, 2948, 1704, 1632, 1438, 1392, 1284, 1156, 1100, 950, 894 Proton NMR spectrum (δ ppm in CDCl$_3$): 1.08–1.28 (3H, m), 1.32–1.44 (3H, m), 2.00–2.20 (1H, m), 2.40–2.98 (2H, m), 3.18 (2H, q, J=8 Hz), 3.44–3.92 (3H, m), 3.73 (3H, s), 4.28 (1H, brs), 4.72 (0.5H, d, J=8 Hz), 4.88 (0.5H, d, J=8 Hz), 4.95 (0.5H, q, J=6 Hz), 5.07 (0.5H, q, J=5 Hz), 5.87 (1H, brs), 7.50 (1H, m) Mass spectrum m/z (%): 299 (M+)

DEFINITE EXAMPLE 22

40 ml of dimethylformamide solution of 4.7 g of methyl (1S, 4aS, 7aS)-1-[(1-(ethoxy)ethoxy]-1,4a,5,7a-tetrahydro-7-(hydroxymethyl)cyclopenta[c]pyran-4-carboxylate obtained in Definite Example 21 was added to 60 ml of a dimethylformamide suspension of 17.8 g of pyridinium dichromate and 15 g of a molecular sieve 4 Å, and the reaction mixture was stirred at room temperature for 4 hours. Insoluble matters in the reaction mixture were removed by celite filtration, and the celite was washed with ethyl acetate. The joined filtrate was washed twice by saturated sodium chloride solution and once by saturated sodium hydrogen carbonate solution, and was dried by anhydrous magnesium sulfate. After filtration, the solvent was distilled off under a reduced pressure, and the resulting reside was purified by column chromatography using 200 g of a silica gel. When the solvent of the fraction obtained from hexane:ether=1:1 eluent, 4.02 g of a colorless oily substance was obtained (yield=86.0%). Since this colorless oily substance had the following physicochemical properties, it was determined as methyl (1S, 4aS, 7aS)-1-[1-(ethoxy)ethoxy]-7-formyl-1,4a,5,7a-tetrahydrocyclopenta[c]pyran-4-carboxylate.

Proton NMR spectrum (δ ppm in CDCl$_3$): 1.15–1.23 (3H, m), 1.32–1.67 (3H, m), 2.52–2.68 (1H, m), 2.92–3.12 (1H, m), 3.24–3.82 (4H, m), 3.73 (3H, s), 4.87 (0.6H, q, J=5 Hz), 5.02 (0.4H, q, J=5 Hz), 5.57 (0.6H, d, J=4 Hz), 5.62 (0.4H, d, J=4 Hz), 7.00 (1H, d, J=3 Hz), 7.46 (1H, s),

DEFINITE EXAMPLE 23

200 mg of genipin was added to 10 ml of a chloroform suspension of 570 mg of pyridinium chlorochromate and 600 mg of a molecular sieve 4 Å, and the reaction mixture solution was stirred at room temperature for 14 hours. Ether was added, and the reaction mixture solution was further stirred for 5 minutes and then insoluble matters were removed by celite filtration. The solvent was distilled off under a reduced pressure, and the resulting residue was purified by a preparative thin layer chromatography to give 120 mg of a colorless oily substance (yield=60.5%). Since this colorless oily substance had the following physicochemical properties, it was determined as methyl (4aS, 7aS)-7-formyl-1,4a,5,7a-tetrahydro-1-hydroxycyclopenta[c]pyran-4-carboxylate.

IR absorption spectrum υ neat max cm$^{-1}$: 3292, 2952, 1702, 1668, 1632, 1436, 1386, 1290, 1148, 1102, 966, 900, 666 Proton NMR spectrum (δ ppm in CDCl$_3$): 2.08–3.52 (4H, m), 3.72 (1.5H, s), 3.75 (1.5H, s), 4.85 (0.5H, d, J=8 Hz), 5.29 (0.5H, brs), 7.16 (0.5H, brs), 7.25 (1H, brs), 7.50 (0.5H, s), 7.56 (0.5H, s), 9.70 (0.5H, s), 9.79 (0.5H, s)

DEFINITE EXAMPLE 24

3.01 g of genipin was dissolved in 25 ml of dimethylformamide, and after 1.0 g of imidazole and 3.76 ml of tert-butyldiphenylsilyl chloride were added, the reaction mixture was stirred at room temperature for 1.5 hours. It was then dissolved in 100 ml of ether, washed by water (50 ml), saturated sodium hydrogen carbonate solution (50 ml) and saturated sodium chloride solution (50 ml), and thereafter dried by anhydrous magnesium sulfate. After filtration, the solvent was distilled off, and 6.75 g of the resulting colorless oily substance was purified by column chromatography (ether:hexane=1:2) using 100 g of silica gel to give 6.07 g of a colorless oily substance (yield=98%). Since this colorless oily substance had the following physicochemical properties, it was determined as methyl (4aS, 7aS)-7-[(tert-butyldiphenylsilyloxy)methyl]-1,4a,5,7a-tetrahydro-1-hydroxypenta[c]pyran-4-carboxylate.

Specific rotation: [α]26D +52.5° (c=1.34, CHCl$_3$) IR absorption spectrum υ CHCl$_3$ max cm$^{-1}$: 3316, 2932, 2860, 1702, 1632 Proton NMR spectrum (σ ppm in CDCl$_3$): 1.07 (9H, s), 2.01–2.13 (1H, m), 2.51 (1H, t, J=8 Hz), 2.84 (1H, dd, J=5.9 Hz), 3.19 (1H, q, J=9 Hz), 3.73 (3H, s), 4.34 (2H, s), 4.73–4.83 (2H, m), 5.78–5.82 (1H, m), 7.35–7.49 (6H, m), 7.54 (1H, d, J=1 Hz), 7.66–7.71 (4H, m) Mass spectrum m/z (%): 464 (M+)

DEFINITE EXAMPLE 25

12.3 g of methyl (4aS, 7aS)-7-[(tert-butyldiphenylsilyloxy)methyl]-1,4a,5,7a-tetrahydro-1-hydroxycyclopenta[c]pyran-4-carboxylate obtained in Definite Example 24 was dissolved in 30 ml of dichloromethane, and after 3.7 ml of dihydropyran and 100 mg of pyridinium para-toluensulfonate were added, the reaction solution was stirred at room temperature for 4 hours. After being washed with saturated sodium hydrogen carbonate solution (50 ml), it was dried by anhydrous magnesium sulfate. After filtration, the solvent was distilled off under a reduced pressure, and 8.0 g of the resulting oily substance was purified by column chromatography (silica gel200 g, ether:hexane=1:3) to give 14.0 g of a colorless oily substance (yield=96%). Since this colorless oily substance had the following physicochemical properties, it was determined as methyl (1S, 4aS, 7aS)-7-[(tert-butyl-diphenylsilyloxy)methyl]-1,4a,5,7a-tetrahydro-1-(2-tetrahydropyranyloxy)cyclopenta[c]pyran-4- carboxylate. IR absorption spectrum υ CHCl₃ max cm⁻¹: 2948, 2860, 1730, 1702, 1632 Proton NMR spectrum (σ ppm in CDCl₃): 1.07 (9H, s), 1.33–1.70 (6H, m), 2.03–2.24 (1H, m), 2.45–2.65 (1H, m), 2.80–2.98 (1H, m), 3.16–3.28 (1H, m), 3.34–3.63 (2H, m), 3.73 (3H, s), 4.24–4.57 (2H, m), 4.99 (1H, d, J=5 Hz), 5.13 (1H, brs), 5.97 (1H, brs), 7.32–7.78 (11H, m) Mass spectrum: 548 (M+)

DEFINITE EXAMPLE 26

14.5 g of methyl (1S, 4aS, 7aS)-7-[(tert-butyldiphenylsilyloxy)methyl]-1,4a,5,7a-tetrahydro-1-(2-tetrahydropyranyloxy)cyclopenta[c]pyran-4-carboxylate obtained in Definite Example 25 was dissolved in 80 ml of tetrahydrofuran, and after 40 ml of a 1.50M toluene solution of diisobutylaluminum hydride was added, the reaction solution was cooled by ice and stirred for 40 minutes. 100 ml of a 2N hydrochloric acid solution was added, and then ether was added. The ether layer was washed with 2N hydrochloric acid solution (100 ml), water (100 ml) and saturated sodium chloride solution (50 ml). It was dried by anhydrous magnesium sulfate, and filtered. When the solvent was distilled off, there was obtained 15.9 g of a colorless oily substance. This substance was dissolved in 150 ml of toluene, and after 30 g of active manganese dioxide was added, the reaction solution was stirred at room temperature for 3 hours. After filtration, the reaction solution was concentrated to give 13.4 g of a pale yellow oily substance. After 50 ml of acetic acid, 25 ml of water and 10 ml of tetrahydrofuran were added, the reaction solution was heated at 60° C. for 4 hours, and then the solvent was distilled off. 15.0 g of the resulting colorless oily substance was dissolved in 50 ml of dichloromethane, and after 5 ml of acetic anhydride, 8 ml of pyridine and 200 mg of 4-dimethylaminopyridine were added, the reaction solution was stirred at room temperature for 14.5 hours. The reaction solution was washed with 2N hydrochloric acid solution (50 ml), water (50 ml), saturated sodium hydrogen carbonate solution (50 ml) and saturated sodium chloride solution (50 ml), it was dried by anhydrous magnesium sulfate. After filtration, the solvent was distilled off, and 13.0 g of the resulting oily substance was purified by column chromatography (silica gel 200 g, ether:hexane=1:3) to give 6.40 g of a pale yellow oily substance (yield=51%). Since this colorless oily substance had the following physicochemical properties, it was determined as (1S, aS, 7aS)-1-acetoxy-7-[(tert-butyldiphenyl-silyloxy)methyl]-1,4a,5,7a-tetrahydrocyclopenta[c]pyran-4-carbaldehyde.

Proton NMR spectrum (σ ppm in CDCl₃): 1.06 (9H, s), 1.93 (3H, s), 2.04–2.30 (1H, m), 2.76–2.98 (2H, m), 3.30 (1H, q, J=6 Hz), 4.26 (2H, s), 5.82 (1H, s), 6.11 (1H, d, J=6 Hz), 7.17 (1H, s), 7.37–7.71 (10H, m), 9.31 (1H, s) IR absorption spectrum υ CHCl₃ max cm⁻¹: 3048, 2932, 2892, 2860, 2740, 1764, 1674, 1632, 1590 Mass spectrum m/z (%): 476 (M+)

DEFINITE EXAMPLE 27

6.40 g of (1S, 4aS, 7aS)-1-acetoxy-7-[(tert-butyldiphenylsilyloxy)methyl]-1,4a,5,7a-tetrahydrocyclopenta[c]pyran-4-carbaldehyde obtained in Definite Example 26 was dissolved in 60 ml of methanol and 1.0 g of sodium hydrogencarbonate was added. While being cooled by ice, the reaction mixture was stirred for 10 minutes and after 50 ml of saturated sodium chloride solution was added, extraction was made with dichloromethane (40 ml×5). The dichloromethane layers were joined and dried by anhydrous magnesium sulfate. After filtration, the solvent was distilled off to give 6.3 g of a colorless oily substance. This substance was dissolved in 50 ml of tetrahydrofuran and 5.0 g of benzoic acid was added. Furthermore, 21 ml of a 1M tetrahydrofuran solution of tetra-n-butylammonium fluoride was added. After the reaction solution was stirred at room temperature for 16 hours, the solvent was distilled off, and 15 g of the resulting oily substance was purified by column chromatography (silica gel 70 g, ether) to give 1.94 g of a colorless oily substance. Since this colorless oily substance had the following physicochemical properties, it was determined as (1S, 4aS, 7aS)-1-acetoxy-4,7-bis(hydroxymethyl)-1,4a,5,7a-tetrahydrocyclopenta[c]pyran.

Specific rotation: [α]26D+6.22° (c=1.13, CHCl₃) Proton NMR spectrum (δ ppm in CDCl₃): 2.15 (3H, s), 2.20–2.60 (2H, m), 2.28 (1H, ddt, J=7, 16, 2 Hz), 2.73 (1H, dd, J=7, 15 Hz), 2.88 (1H, t, J=7 Hz), 3.13 (1H, q, J=7 Hz), 4.04 (1H, d, J=12 Hz), 4.14 (1H, d, J=12 Hz), 4.25 (2H, d, J=1.5 Hz), 5.83 (1H, d, J=7 Hz), 5.85 (1H, s), 6.41 (1H, s) IR absorption spectrum υ CHCl₃ max cm⁻¹: 3600, 3444, 2928, 2872, 1762, 1666 Mass spectrum m/z (%): 240 (M+)

DEFINITE EXAMPLE 28

15.2 g of pyridinium chlorochromate was dissolved in 400 ml of dichloromethane, and after 25.0 g of a molecular sieve 3 Å was added, the reaction mixture was stirred at room temperature for 5 minutes. 100 ml of a dichloromethane solution of 6.3 g of methyl (4aS, 7aS)-7-[(tert-butyldiphenylsilyloxy)methyl]-1,4a,5,7a-tetrahydro-1-hydroxycyclopenta[c]pyran-4-carboxylate obtained in Definite example 24 was added, and the reaction mixture was stirred at room temperature for 3.5 hours. 500 ml of ether was added to the reaction solution and after insoluble matters were filtered, the filtrate was concentrated, and 8.5 g of the resulting oily substance was purified by column chromatography (silica gel 100 g, ether:hexane=1:3) to give 3.87 g of a colorless solid (yield=62%). Furthermore, this colorless solid was recrystallized from hexane to give a colorless needle-like crystal. Since this colorless needle-like crystal had the following physicochemical properties, it was determined as methyl (4aS, 7aS)-7-[(tert-butyldiphenylsilyloxy)methyl]-1,4a,5,7a-tetrahydro-1-oxocyclopenta[c]pyran-4-carboxylate.

Melting point: 111.5°–112.5° C. Specific rotation: [α] 26D+142.3° (c=1.11, CHCl₃) Elementary analysis: calculated C: 70.10 H: 6.54 found C: 70.09 H: 6.56 Proton NMR spectrum (δ ppm in CDCl₃): 0.97 (9H, s), 2.15–2.29 (1H, m), 2.88 (1H, dd, J=8, 16 Hz), 3.48 (1H, dt, J=10, 8 Hz), 3.64 (1H, d, J=10 Hz), 3.79 (3H, s), 4.52 (2H, br), 5.89 (1H, br), 7.35–7.82 (11H, m) IR absorption spectrum υ KBr max cm⁻¹: 3104, 2948, 2932, 2896, 2856, 1770, 1712, 1658, 1470, 1288, 1140, 1112, 1074 Mass spectrum m/z (%): 405 (M+-C₄H₉)

DEFINITE EXAMPLE 29

50 ml of a chloroform solution of 10 g of genipin was added to 200 ml of anhydrous chloroform solution of 30 mg of vanadyl acetylacetonate under an argon atmosphere, and tert-butyl hydroperoxide (23 ml of 3.0M neopentane solution) was added dropwise in the course of 15 minutes. The reaction solution was stirred at 40° C. for 15 hours. Saturated sodium chloride solution and sodium thiosulfate were added to this reaction mixture solution, and the solution was stirred for 10 minutes.

Next, extraction was made once using 200 ml of chloroform and twice with 200 ml of ethyl acetate, and the joined organic layer was dried by anhydrous magnesium sulfate, filtered and then distilled off under a reduced pressure. The resulting residue was purified by column chromatography using 250 g of silica gel, and the solvent of the fraction obtained from the ether eluent was distilled off. The residue was recrystallized from dichloromethane-hexane to give 7.3 g of a colorless needle-like crystal (yield=68.2%). Since this colorless needle-like crystal had the following physicochemical properties, it was determined as methyl (4aS, 7aS)-6,7-epoxy-1,4a,5,6,7,7a-hexahydro-1-hydroxy-7-(hydroxymethyl)cyclopenta[c]pyran-4-carboxylate.

IR absorption spectrum $\upsilon$ KBr max cm$^{-1}$: 3532, 3324, 1712, 1638, 1446, 1380, 1290, 1192, 1154, 974, 770 Proton NMR spectrum ($\delta$ ppm in CDCl$_3$): 1.40 (1H, dd, J=9, 13 Hz), 2.43 (1H, dd, J=7, 9 Hz), 2.56-2.90 (2H, m), 3.51 (1H, s), 3.72 (3H, s), 3.86 (1H, d, J=13 Hz), 4.22 (1H, d, J=13 Hz), 4.91 (0.8H, d, J=9 Hz), 5.75 (0.2H, d, J=4 Hz), 7.45 (1H, s) Elementary analysis: calculated C: 54.54 H: 5.83 found C: 54.30 H: 5.89

DEFINITE EXAMPLE 30

10 ml of anhydrous chloroform solution of 1.0 g of genipin was added to 20 ml of anhydrous chloroform solution of 6 mg of vanadyl acetylacetonate under an argon atmosphere, and tert-butyl hydroperoxide (3.0M neopentane solution 2.1 ml ) was added dropwise in the course of 15 minutes. The reaction mixture was stirred at 40° C. for 24 hours. After saturated sodium chloride solution and sodium thiosulfate were added, the reaction mixture solution was stirred for 10 minutes. Next, the aqueous layer was extracted once with 50 ml of chloroform and twice with 50 ml of ethyl acetate, and the joined organic layer was dried by anhydrous magnesium sulfate, filtered and then distilled off under a reduced pressure. The resulting residue was dissolved in 15 ml of dichloromethane, and after 1.5 ml of pyridine, 1.7 ml of acetic anhydride and 10 mg of 4-dimethylaminopyridine were added, the reaction mixture was stirred at room temperature for 5 hours. The reaction mixture was extracted by 100 ml of ethyl acetate. The organic layer washed with water, saturated sodium hydrogen carbonate solution, potassium hydrogen sulfate solution and saturated sodium chloride solution was dried by anhydrous magnesium sulfate, filtered and then distilled off under a reduced pressure. The resulting residue was purified by column chromatography using 30 g of silica gel, and the fraction obtained from hexane:ether=7:3 eluent was recrystallized from ethyl acetate-hexane to give 550 mg of a colorless needle-like crystal (yield=38.1%). Since this colorless needle-like crystal had the following physicochemical properties, it was determined as methyl (1S, 4aS, 7aS)-1,7-diacetoxy-6,7-(epoxymethano)-1,4a,5,6,7,7a-hexahydrocyclopenta[c]pyran-4-carboxylate.

IR absorption spectrum $\upsilon$ KBr max cm$^{-1}$: 1740, 1704, 1632, 1440, 1376, 1268, 1240, 1164, 1074, 1054, 1016, 968, 944, 868 Proton NMR spectrum ($\delta$ ppm in CDCl$_3$): 1.95 (1H, d, J=2 Hz), 2.06 (3H, s), 2.10 (3H, s), 2.13-2.17 (1H, m), 2.97 (1H, d, J=6 Hz), 3.36 (1H, m), 3.71 (3H, s), 3.86 (1H, d, J=1 Hz), 4.68 (1H, s), 4.77 (1H, d, J=1 Hz), 5.95 (1H, s), 7.33 (1H, s) Elementary analysis: calculated C: 55.21 H: 5.56 found C: 55.18 H: 5.44 Mass spectrum m/z (%): 326 (M+)

DEFINITE EXAMPLE 31

100 mg of genipin was dissolved in 5 ml of methanol and after 5 mg of platinum oxide was added, the reaction mixture was stirred at room temperature for 6 hours in a hydrogen atmosphere of 1 atm. After filtration, the reaction solution was concentrated, and 112 mg of the resulting oily substance was purified by column chromatography (silica gel 20 g, ether). The solvent of the resulting fraction was distilled off, and 60 mg of the solid thus obtained was recrystallized from ether-hexane to give 35 mg of a colorless plate-like crystal (yield=37%). Since this colorless plate-like crystal had the following physicochemical properties, it was determined as methyl (4aS, 7R, 7aR)-1,4a,5,6,7,7a-hexahydro-1-hydroxy-7-methylcyclopenta[c]pyran-4-carboxylate.

Melting point: 80°-81° C. Specific rotation: [$\alpha$] 26D −40.0° (c=1.02, CHCl$_3$) IR absorption spectrum $\upsilon$ KBr max cm$^{-1}$: 3444, 2968, 2944, 1678, 1630, 1444, 1214, 1134, 890, 836, 768 Proton NMR spectrum ($\delta$ ppm in CDCl$_3$): 1.13 (2.7H, d, J=7 Hz), 1.15 (0.3H, d, J=7 Hz), 1.23-1.60 (2H, m), 1.75-2.49 (4H, m), 2.91 (1H, q, J=8 Hz), 3.10 (1H, d, J=7 Hz), 3.71 (2.7H, s), 3.72 (0.3H, s), 5.08 (0.9H, t, J=7 Hz), 5.51 (0.1H, t, J=2 Hz), 7.42 (1H, d, J=0.7 Hz) Mass spectrum m/z (%): 212 (M+)

DEFINITE EXAMPLE 32

60.0 g of pyridinium chlorochromate was dissolved in 450 ml of dichloromethane, and 60.0 g of a molecular sieve 3 Å was added. After the reaction mixture was stirred at room temperature for 5 minutes, 50 ml of a dichloromethane solution of methyl (4aS, 7R, 7aR)-1,4a,5,6,7,7a-hexahydro-1-hydroxy-7-methylcyclopenta[c]pyran-4-carboxylate (11.6 g) obtained in Definite Example 31 was added, and the reaction mixture was stirred at room temperature for 3 hours. Then, 500 ml of ether was added. After filtration, the solvent was distilled to give 15.0 g of a brown oily substance. This substance was purified by column chromatography (silica gel 200 g, ether:hexane=1:2) to give 8.10 g of a colorless oily substance (yield=70.5%). Since this colorless oily substance had the following physicochemical properties, it was determined as methyl (4aS, 7R, 7aR)-1, 4a,5,6,7,7a-hexahydro-7-methyl-1-oxocyclopenta[c]pyran-4-carboxylate.

Specific rotation: [$\alpha$]26D −65.19° (c=1.08, CHCl$_3$) IR absorption spectrum $\upsilon$ neat max cm$^{-1}$: 2956, 2876, 1778, 1714, 1660 Proton NMR spectrum ($\delta$ ppm in CDCl$_3$): 1.05 (3H, d, J=7 Hz), 1.39-1.53 (1H, m), 1.65-1.93 (2H, m), 2.16-2.40 (1H, m), 2.48-2.78 (1H, m), 3.08-3.30 (2H, m), 3.77 (3H, s), 7.41 (1H, d, J=1 Hz) Mass spectrum m/z (%): 210 (M+)

DEFINITE EXAMPLE 33

226 mg of genipin was dissolved in 5 ml of dichloromethane, and after 0.6 ml of dihydropyran and 4 mg of pyridinium para-toluenesulfonate were added, the reaction mixture was stirred at room temperature for 20 hours. After 20 ml of ether was added, extraction was made with water (10 ml), saturated aqueous sodium hydrogen carbonate solution (10 ml) and saturated sodium chloride solution (10 ml), and drying was made by anhydrous magnesium sulfate. After filtration, the solvent was distilled off to give 366 mg of a colorless oily substance. This substance was dissolved in 5 ml of tetrahydrofuran and while the reaction mixture was cooled by ice, 2.0 ml of 1.50M toluene solution of diisobutylaluminum hydride was added. Then, the reaction mixture was as such stirred for 30 minutes. After 40 ml of 2N hydrochloric acid solution was added, 50 ml of ether was added, and the ether layer was washed with water (10 ml×1), saturated sodium hydrogen carbonate solution (10 ml) and saturated sodium chloride solution (10 ml), and dried by anhydrous magnesium sulfate. After filtration, the solvent was distilled off to give 268 mg of a colorless oily substance. When this oily substance was purified by column chromatography (silica gel 20 g, ether:hexane=1:1), there were obtained fractions A and B. When the solvent of the fraction A was distilled off, there was obtained 80 mg of a colorless oily substance (yield=22%). Since this substance had the following physicochemical properties, it was determined as (1S, 4aS, 7aS)-1,4a,5,7a-tetrahydro-1-(2-tetrahydropyranyloxy)-7-[(2-tetrahydropyranyloxy)methyl]-4-(hydroxymethyl)cyclopenta[c]pyran.

Proton NMR spectrum ($\delta$ ppm in CDCl$_3$): 1.37–1.99 (12H, m), 2.07–2.31 (1H, m), 2.69 (2H, q, J=8 Hz), 3.06 (1H, q, J=9 Hz), 3.43–3.59 (2H, m), 3.59–4.31 (5H, m), 4.51 (1H, t, J=16 Hz), 4.63–4.74 (1H, m), 4.84 (1H, d, J 8 Hz), 4.86 (1H, d, J=8 Hz), 5.14 (1H, s), 5.85 (1H, s), 6.39 (1H, s)

45 mg of the colorless oily substance obtained by distilling off the solvent of the fraction B (yield=12%) had the physicochemical properties listed below. Therefore, this substance was determined as (1S, 4aS, 7aS)-1,4a,5,7a-tetrahydro-1-(2-tetrahydropyranyloxy)-7-[2-tetrahydropyranyloxy)methyl]-4-(hydroxymethyl)cyclopenta[c]pyran.

Proton NMR spectrum ($\delta$ ppm in CDCl$_3$): 1.43–1.99 (12H, m), 2.03–2.23 (1H, m), 2.56–2.80 (2H, m), 3.04 (1H, q, J=9 Hz), 3.43–3.63 (2H, m), 3.63–4.18 (6H, m), 4.36 (1H, t, J=12 Hz), 4.61–4.69 (2H, m), 4.83 (1H, s), 5.85 (1H, s), 6.43 (1H, s)

DEFINITE EXAMPLE 34

226 mg of genipin was dissolved in 5 ml of dimethylformamide, and after 509 mg of silver nitrate and 452 mg of tert-butyldimethylsilyl chloride were added, the reaction mixture was stirred at room temperature for 17 hours. After 10 ml of saturated sodium hydrogen carbonate solution was added and filtration was made, the filtrate was extracted with ether (20 ml×4). The joined ether layer was washed with water (10 ml), saturated sodium hydrogen carbonate solution (10 ml) and saturated sodium chloride solution (10 ml), and dried by anhydrous magnesium sulfate. The reaction product was dissolved in 8 ml of tetrahydrofuran and while the reaction mixture was being cooled by ice, 2.6 ml of 1.50M toluene solution of diisobutylaluminum hydride was added. The reaction mixture was stirred for 30 minutes. After 40 ml of 2N hydrochloric acid solution was added, extraction was made by 50 ml of ether. The ether layer was washed with water (10 ml) and dried by anhydrous magnesium sulfate. After drying, the solvent was distilled off and 290 mg of the resulting oily substance was purified by column chromatography (silica gel 40, ether:hexane=1:2) to give 290 mg of a colorless oily substance (yield=68%). Since this colorless oily substance had the following physicochemical properties, it was determined as (1S, aS, 7aS)-1-(tert-butyldimethylsilyloxy)-7-[(tert-butyldimethylsilyloxy)methyl]-1,4a,5,7a-tetrahydro-4-(hydroxymethyl)cyclopenta[c]pyran.

Proton NMR spectrum ($\delta$ ppm in CDCl$_3$): 0.068 (3H, s), 0.073 (3H, s), 0.11 (3H, s), 0.13 (3H, s), 0.92 (18H, s), 1.58 (1H, br), 2.06–2.20 (1H, m), 2.46 (1H, dt, J=1, 8 Hz), 2.61–2.74 (1H, m), 3.02 (1H, q, J=8 Hz), 4.06 (2H, s), 4.22 (1H, d, J=15 Hz), 4.38 (1H, d, J=15 Hz) 4.72 (1H, d, J=8 Hz), 5.80 (1H, s), 6.39 (1H, s) IR absorption spectrum $v$ neat max cm$^{-1}$: 3350, 2956, 2932, 2890, 2856, 1665

DEFINITE EXAMPLE 35

800 mg of methyl (4aS, 7aS)-1,4a,5,7a-tetrahydro-1-hydroxy-7-methylcyclopenta[c]pyran-4-carboxylate obtained in Definite Example 9 was dissolved in a mixed solvent of chloroform:water=1:1 (20 ml), and after 4.7 g of magnesium monoperoxyphthalate was added, the reaction mixture was stirred at room temperature for 6 hours. The reaction mixture was extracted with ethyl acetate (200 ml), and the organic layer was washed with water and then dried by anhydrous magnesium sulfate. After filtration, the solvent was distilled off and the resulting residue was purified by column chromatography using silica gel (20 g). The solvent of the fraction obtained from hexane:ether=2:3 eluent was distilled off and the residue was further recrystallized from hexane-ether to give 580 mg of a colorless needle-like crystal (yield=67.4%). Since this colorless needle-like crystal had the following physicochemical properties, it was determined as methyl (4aS, 7aS)-6,7-epoxy-1,4a,5,6,7,7a-hexahydro-1-hydroxy-7-methyl-cyclopenta[c]pyran-4-carboxylate.

IR absorption spectrum $v$ KBr max cm$^{-1}$: 3376, 2952, 1682, 1636, 1444, 1312, 1290, 1158, 1090, 894, 828 Proton NMR spectrum ($\delta$ ppm in CDCl$_3$): 1.21–1.84 (4H, m), 2.08–2.86 (4H, m), 3.32 (0.3H, s), 3.70 (0.7H, s), 3.72 (3H, s), 4.88 (0.3H, d, J=10 Hz), 5.62 (0.7H, d, J=3 Hz), 7.42 (1H, s),

DEFINITE EXAMPLE 36

1 ml of pyridine, 2.69 g of benzoic anhydride and 20 mg of 4-dimethylaminopyridine were added to a dichloromethane solution (20 ml) of 500 mg of methyl (4aS, 7aS)-1,4a,5,7a-tetrahydro-1-hydroxy-7-methylcyclopenta[c]pyran-4-carboxylate, and the reaction mixture was stirred at room temperature for 12 hours. The reaction mixture was dissolved in ethyl acetate (300 ml), and the organic layer was washed once with water, twice with sodium hydrogen carbonate solution, once with potassium hydrogen sulfate solution and once with sodium chloride solution, and was dried by anhydrous magnesium sulfate. After filtration, the solvent was distilled off under a reduced pressure, and the resulting residue was purified by column chromatography using silica gel (15 g). The solvent of the fraction obtained from hexane:ether=7:3 eluent was distilled off, and 620 mg of a pale yellow oily substance was obtained (yield=82.9%). Since this pale yellow oily substance had the following physicochemical properties, it was determined as methyl (2S, 4aS, 7aS)-1-benzoyloxy-1,4a,5,7a-tetrahydro-7-methylcyclopenta[c]pyran-4-carboxylate.

Proton NMR spectrum ($\delta$ ppm in CDCl$_3$): 1.91 (3H, brs), 2.12–2.32 (1H, m), 2.72–2.86 (2H, m), 3.24–3.42 (1H, m), 3.92 (3H, s), 5.58 (1H, brs), 6.22 (1H, d, J=8 Hz), 7.41 (1H, s), 7.40–8.22 (5H, m),

DEFINITE EXAMPLE 37

A dichloromethane solution (50 ml) of 5.0 g of methyl (4aS, 7aS)-1,4a,5,7a-tetrahydro-1-hydroxy-7-methylcyclopenta[c]pyran-4-carboxylate obtained in Definite Example 9 was added to a dichloromethane solution (100 ml) of 15.4 g of pyridinium chlorochromate, sodium acetate (5.4 g) and a molecular sieve 4 Å (10 g), and the reaction mixture was stirred at room temperature. Four hours later, ether was added and celite filtration was made. The solvent was dissolved under a reduced pressure, and the resulting residue was purified by column chromatography using silica gel (150 g). The solvent of the fraction obtained from hexane:ether=3:1 effluent was distilled off, and 3.1 g of a colorless oily substance was obtained (yield=62.6%). Since this colorless oily substance had the following physicochemical properties, it was determined as methyl (4aS, 7aS)-1,4a,5,7a-tetrahydro-7-methyl-1-oxocyclopenta[c]pyran-4-carboxylate.

IR absorption spectrum υ neat max cm$^{-1}$: 2952, 2924, 1778, 1722, 1658, 1440, 1328, 1286, 1232, 1178, 1092 Proton spectrum (δ ppm in CDCl$_3$): 1.94 (3H, brs), 2.12–2.34 (1H, m), 2.76–3.00 (1H, m), 3.46–3.56 (2H, t, J=5 Hz), 3.78 (3H, s), 5.61 (1H, brs), 7.47 (1H, s) Specific rotation: [α] 27+281.30° (c=1.00, CHCl$_3$)

DEFINITE EXAMPLE 38

12.5 ml of pyridine was added to a dichloromethane solution (70 ml) of 6.5 g of methyl (4aS, 7aS)-1,4a,5,7a-tetrahydro-1-hydroxy-7-methylcyclopenta[c]pyran-4-carboxylate obtained in Definite Example 9, and 8.8 ml of acetic anhydride was added dropwise. Furthermore, 30 mg of 4-dimethylaminopyridine was added, and the reaction mixture was stirred at room temperature for 5 hours. The reaction mixture was dissolved in ethyl acetate (500 ml), and the organic layer was washed twice with saturated sodium hydrogen carbonate solution, twice with potassium hydrogen sulfate solution and once with saturated sodium chloride solution, and was dried by anhydrous magnesium sulfate. After filtration, the solvent was distilled off under a reduced pressure, and the resulting residue was purified by column chromatography using silica gel (200 g). The solvent of the fraction obtained from hexane:ether=3:1 eluent was distilled off, and 7.5 g of a colorless oily substance was obtained (yield=96.2%). Since this colorless oily substance had the following physicochemical properties, it was determined as methyl (1S, 4aS, 7aS)-1-acetoxy-1,4a,5,7a-tetrahydro-7-methylcyclopenta[c]pyran-4-carboxylate.

IR absorption spectrum υ neat max cm$^{-1}$: 2948, 2856, 1758, 1706, 1636, 1438, 1378, 1286, 1172, 1152, 1080, 980, 964, 914, 666 Proton NMR spectrum (δ ppm in CDCl$_3$): 1.78 (3H, brs), 2.04–2.26 (1H, m), 2.15 (1H, s), 2.60–2.92 (2H, m), 3.16–3.32 (1H, m), 3.73 (3H, s), 5.53 (1H, brs), 5.93 (1H, d, J=7 Hz), 7.44 (1H, s)

DEFINITE EXAMPLE 39

200 mg of methyl (4aS, 7S, 7aS)-1,4a,5,7,7a-hexahydro-1-hydroxy-7-(hydroxymethyl)cyclopenta[c]pyran-4-carboxylate obtained in Definite Example 6 was dissolved in 10 ml of diethylformamide, and after 74 mg of imidazole and 0.35 ml of tert-butyldiphenylsilyl chloride were sequentially added, the reaction mixture was stirred at room temperature. Twelve hours later, the reaction mixture was dissolved in ethyl acetate. The organic layer was washed with saturated sodium hydrogen carbonate solution and saturated sodium chloride solution, and was then dried by anhydrous magnesium sulfate. After filtration, the solvent was distilled off under a reduced pressure, and the resulting residue was purified by column chromatography using silica gel (10 g). The solvent of the fraction obtained from hexane:ether=3:1 eluent was distilled off, and 336 mg of a colorless oily substance was obtained (yield=84.4%). Since this colorless oily substance had the following physicochemical properties, it was determined as methyl (4aS, 7S, 7aS)-7-[(tert-butyldiphenylsilyloxy)methyl]-1,4a,5,6,7,7a-hexahydro-1-(hydroxycyclopenta[c]pyran-4-carboxylate.

IR absorption spectrum υ neat max cm$^{-1}$: 2952, 2932, 2860, 1702, 1628, 1428, 1304, 1216, 790 Proton NMR spectrum (δ ppm in CDCl$_3$): 0.78–0.96 (1H, m), 1.10 (9H, s), 1.16–1.40 (1H, m), 1.60–2.12 (1H, m), 2.16–2.88 (2H, m), 3.12–3.56 (2H, m), 3.73 (3H, s), 4.35 (1H, d, J=8 Hz) 4.76 (1H, t, J=8 Hz), 5.24 (0.5H, d, J =10 Hz), 6.64 (0.5H, d, J=10 Hz), 7.52 (1H, s), 7.36–7.76 (10H, m)

DEFINITE EXAMPLE 40

A dichloromethane solution (15 ml) of 1.3 g of methyl (4aS, 7S, 7aS)-7-[(tert-butyldiphenylsilyloxy)methyl]-1,4a,5,6,7,7a-hexahydro-1-hydroxycyclopenta[c]pyran-4-carboxylate obtained in Definite Example 39 was added to a dichloromethane suspension of 1.46 g of pyridinium chlorochromate, 560 mg of sodium acetate and 1 g of celite, and the reaction mixture was stirred at room temperature. Five hours later, ether was added and then celite filtration was made. The solvent was distilled off under a reduced pressure, and the resulting residue was purified by column chromatography using silica gel (30 g). The solvent of the fraction obtained from hexane:ether=7:3 eluent was distilled off, and 990 mg of a colorless oily substance was obtained (yield=76.5%). Since this colorless oily substance had the following physicochemical properties, it was determined as methyl (4aS, 7S, 7aS)-7-[(tert-butyldiphenylsilyloxy)methyl]-1,4a,5,6,7,7a-hexahydro-1-oxocyclopenta[c]pyran-4-carboxylate.

IR absorption spectrum υ neat max cm$^{-1}$: 2956, 2860, 1778, 1718, 1654, 1428, 1174, 1092, 740 Proton NMR spectrum (δ ppm in CDCl$_3$): 1.06 (9H, s), 1.08–1.68 (4H, m), 1.76–1.96 (1H, m), 2.16–2.26 (1H, m), 2.78–3.16 (2H, m), 3.64–3.84 (2H, m), 3.78 (3H, s), 7.48 (1H, s), 7.32–7.76 (10H, m)

DEFINITE EXAMPLE 41

40 mg of imidazole and 820 mg of tert-butyldimethylsilyl chloride were added to a dimethylformamide solution (30 ml) of 1.0 g of methyl (4aS, 7S, 7aS)-1,4a,5,6,7,7a-hexahydro-1-hydroxy-7-(hydroxymethyl)cyclopenta[c]pyran-4-carboxylate obtained in Definite Example 6, and the reaction mixture was stirred at room temperature for 12 hours. The reaction mixture was poured into ethyl acetate (200 ml), and the organic layer was washed with water, saturated sodium hydrogen carbonate solution and saturated sodium chloride solution, and was then dried by anhydrous magnesium sulfate. After filtration, the solvent was distilled off under a reduced pressure, and the resulting residue was purified by column chromatography using silica gel (30 g). The solvent of the fraction obtained from hexane:ether=3:1 eluent was distilled off, and 645 mg of a colorless oily substance was obtained (yield=45.3%). Since this colorless oily substance had the following physicochemical properties, it was determined as methyl (4aS, 7S, 7aS)-7-[(tert-butyldimethylsilyloxy)methyl]-1,4a,5,6,7,7a-hexahydro-1-hydroxypenta[c]pyran-4-carboxylate.

Proton NMR spectrum (δ ppm in CDCl₃): 0.10 (6H, s), 0.92 (9H, s), 1.04–1.28 (1H, m), 1.70–2.40 (4H, m), 2.64–2.84 (1H, m), 3.41 (1H, m), 3.72 (3H, s), 3.80 (1H, m), 4.68 (1H, m), 4.82 (1H, d, J=6 Hz), 5.15 (0.5H, d, J=10 Hz), 6.67 (0.5H, d, J=10 Hz), 7.51 (1H, s)

DEFINITE EXAMPLE 42

A dichloromethane solution (15 ml) of 600 mg of methyl (4aS, 7S, 7aS)-7-[(tert-butyldimethylsilyloxy)-methyl]-1,4a,5,6,7,7a-hexahydro-1-hydroxycyclopenta[c]pyran-4-carboxylate obtained in Definite Example 41 was added to a dichloromethane suspension (15 ml) of 945 mg of pyridinium chlorochromate, 360 mg of sodium acetate and 1 g of a molecular sieve 4 Å, and the reaction mixture was stirred at room temperature. Twelve hours later, ether was added to the reaction mixture and celite filtration was made. Celite was washed with ether and the joined organic layer was distilled off under a reduced pressure. The residue was purified by chromatography using silica gel (20 g), and the solvent of the fraction obtained from hexane:ether=4:1 eluent was distilled off, and 350 mg of a colorless oily substance was obtained (yield=58.7%). Since this colorless oily substance had the following physicochemical properties, it was determined as methyl (4aS, 7S, 7aS)-7-[(tert-butyldimethylsilyloxy)methyl]-1,4a,5,6,7,7a-hexahydro-1-oxocyclopenta[c]pyran-4-carboxylate.

IR absorption spectrum υ neat max cm⁻¹: 2952, 2860, 1772, 1714, 1656, 1438, 1294, 1170, 1096, 832 Proton NMR spectrum (δ ppm in CDCl₃): 0.06 (6H, s), 0.89 (9H, s), 1.16–1.70 (3H, m), 1.70–1.96 (1H, m), 2.16–2.36 (1H, m), 2.68–3.16 (2H, m), 3.52–3.76 (2H, m), 3.78 (3H, s), 7.47 (1H, s)

DEFINITE EXAMPLE 43

10 g of methyl (4aS, 7S, 7aR)-1,4a,5,6,7,7a-hexahydro-1-hydroxy-7-methylcyclopenta[c]pyran-4-carboxylate obtained in Definite Example 4 was dissolved in 100 ml of dichloromethane, and after 50 ml of ethyl vinyl ether and then 100 mg of pyridinium paratoluenesulfonate were added while the reaction mixture was being cooled by ice. Then, the reaction mixture was stirred at room temperature for 24 hours. The reaction mixture solution was extracted with dichloromethane. After 200 ml of dichloromethane was added to the reaction mixture solution, the organic layer was washed with 50 ml of saturated sodium hydrogen carbonate solution and 50 ml of saturated sodium chloride solution, and was then dried by magnesium sulfate. After filtration, the solvent was distilled off under a reduced pressure. 2.5 g of the resulting yellow oily substance, i.e., methyl (1S, 4aS, 7S, 7aR)-1-[1-(ethoxy)ethoxy]-1,4a,5,6,7,7a-hexahydro-7-methylcyclopenta[c]pyran-4-carboxylate was dissolved in 30 ml of anhydrous tetrahydrofuran without purification, and 26.5 ml of diisobutylaluminum hydride (1.0 mol THF solution) was added dropwise while the reaction mixture was being cooled by ice and being stirred (in an argon gas atmosphere). After the reaction mixture was stirred at the same temperature for 2 hours, 2 ml of acetone was added. Next, 3.4 ml of water, 3.4 ml of an aqueous sodium hydroxide and 10 ml of water were added in the order named, and the reaction mixture was stirred. When insoluble matters were precipitated, the precipitate was filtrated and the solvent was distilled off under a reduced pressure. 2.3 g of the resulting colorless oily substance, i.e., (1S, 4aS, 7S, 7aR)-1-[1-(ethoxy)ethoxy]-1,4a,5,6,7,7a-hexahydro-4-(hydroxymethyl)-7-methylcyclopenta[c]pyran was dissolved in 30 ml of anhydrous dichloro-methane without purification, and 4 ml of pyridine was added. Next, 4 ml of acetic anhydride was added dropwise, and after 50 mg of 4-dimethylaminopyridine was added, the reaction mixture was stirred at room temperature for 5 hours. The reaction mixture was extracted with 150 ml of ethyl acetate. The organic layer which was washed by 100 ml of water, 2N hydrochloric acid solution (100 ml×2), saturated sodium hydrogen carbonate solution (100 ml×2) and 100 ml of saturated sodium chloride solution was dried by anhydrous magnesium sulfate, and the solvent was distilled off under a reduced pressure. The resulting colorless oily substance was purified by column chromatography using 50 g of silica gel, and there was obtained 1.6 g of colorless oily substance (1S, 4aS, 7S, 7aR)-4-(acetoxymethyl)-1-[1-(ethoxy)ethoxy]-1,4a,5, 6,7,7a-hexahydro-7-methylcyclopenta[c]pyran (yield=60%) from the hexane:ether=7:3 eluent.

5.0 g of this colorless oily substance, i.e., (1S, 4aS, 7S, 7aR)-4-(acetoxymethyl)-1-[1-(ethoxy)ethoxy]-1,4a,5,6,7,7a-hexahydro-7-methylcyclopenta[c]pyran, was dissolved in a mixed solvent of 100 ml of ethyl acetate and 3 ml of pyridine, and after 150 mg of 10% palladium carbon was added, the reaction mixture was stirred at room temperature for 20 hours in a hydrogen atmosphere of 1 atm. After the catalyst was filtered by celite, extraction was carried out by adding 100 ml of ethyl acetate to the reaction mixture solution. The organic layer was washed with 100 ml of 2N hydrochloric acid solution and saturated sodium chloride solution, and was then dried by magnesium sulfate. After filtration, the solvent was distilled off under a reduced pressure, and a colorless oily substance was obtained (1S, 4aS, 7S, 7aR)-1-[1-(ethoxy)ethoxy]-1,4a,5,6,7,7a-hexahydro-4,7-dimethylcyclopenta[c]pyran.

14.0 g of crude colorless oily substance, i.e., (1S, 4aS, 7S, 7aR)-1-[1-(ethoxy)ethoxy]-1,4a,5,6,7,7a-hexahydro-4,7-dimethylcyclopenta[c]pyran, was dissolved in 200 ml of tetrahydrofuran, and after 30 ml of 2N hydrochloric acid solution was added, the reaction mixture was stirred for 4 hours while being cooled by ice. After 100 ml of saturated sodium hydrogen carbonate solution was added to the reaction mixture solution, extraction was made with ethyl acetate (500 ml×2).

The joined organic layer was dried by magnesium sulfate, filtered and then distilled under a reduced pressure. The resulting residue was purified by chromatography using a silica gel, and 8.5 g of a colorless oily substance was obtained (yield=86.7%) from the hexane:ether=1:1 eluent. Since this colorless oily substance had the following physicochemical properties, it was determined as (4aS, 7S, 7aR)-1,4a 5,6,7,7a-hexahydro-4,7-dimethylcyclopenta[c]pyran-1-ol.

Proton NMR spectrum (δ ppm in CDCl₃): 1.07 (3H, d, J=2.4 Hz), 1.55 (3H, t, J=1 Hz), 1.63–3.40 (8H, m), 4.90 (1H, m), 6.02 (1H, brs) IR absorption spectrum υ neat max cm⁻¹: 3588, 3420, 2932, 1670, 1452, 1314, 1126, 1004, 908, 68 Mass spectrum m/z (%): 168 (M+)

DEFINITE EXAMPLE 44

28.0 g of (1S, 4aS, 7S, 7aR)-1-[1-(ethoxy)ethoxy]-1,4a,5,6,7,7a-hexahydro-4,7-dimethylcyclopenta[c]pyran was dissolved in 500 ml of ethyl acetate, and after 90 mg of 10% palladium carbon was added, the reaction mixture was stirred at room temperature for 48 hours in a hydrogen gas atmosphere of 1 atm. The catalyst was filtered by celite, and the solvent was distilled off under a reduced pressure. There was thus obtained a colorless oily substance, (1S, 4R, 4aS, 7S, 7aR)-1-[1-(ethoxy)ethoxy]-1,3,4,4a,5,6,7,7a-octahydro-4,7-dimethylcyclopenta[c]pyran. 28.0 g of this (1S, 4R, 4aS, 7S, 7aR)-1-[1-(ethoxy)ethoxy]-1,3,4,4a,5,6,7,7a-octahydro-4,7-dimethylcyclopenta[c]pyran was dissolved in 400 ml of tetrahydrofuran without purification, and after 50 ml of 2N hydrochloric acid solution wad added, the reaction mixture was stirred for 12 hours while being cooled by ice. 300 ml of saturated sodium hydrogen carbonate solution was added to the reaction mixture, extraction was made with ethyl acetate (500 ml×3). The joined organic layer was dried by magnesium sulfate, and after filtration, the solvent was distilled off under a reduced pressure. The residue was purified by column chromatography using 200 g of silica gel, and 13.5 g of a colorless oily substance (yield=69.4%) was obtained from the hexane:ether=1:1 eluent. Since various spectral data Of this colorless oily substance were in agreement with the data described in the reference ("Tetrahedron Lett.", 5325, 1968), it was determined as (4R, 4aR, 7S, 7aR)-1,3,4,4a,5,6,7,7a-octahydro-4,7-dimethylcyclopenta[c]pyran-1-ol.

DEFINITE EXAMPLE 45

13.0 g of (4R, 4aR, 7S, 7aR)-1,3,4,4a,5,6,7,7a-octahydro-4,7-dimethylcyclopenta[c]pyran-1-ol obtained in Definite Example 44 was dissolved in 200 ml of methanol, and 9.0 g of sodium borohydride was added while the reaction mixture was being cooled by ice and stirred. Four hours latter, 100 ml of a saturated aqueous ammonium chloride solution was added, and the solvent was distilled off under a reduced pressure. Extraction was then made using ethyl acetate (200 ml×3). The joined organic layer was dried by magnesium sulfate, and after filtration, the solvent was distilled off under a reduced pressure. The resulting residue was recrystallized from hexane:ether to give 10.9 g of a colorless needle-like crystal (yield=83%). Since various spectral data of this colorless needle-like crystal were in agreement with the data described in the reference ("Tetrahedron lett." 46, 4097, 1968), it was determined as (2R)-2-[(1R, 2R, 3S)-2-(hydroxymethyl)-3-methylcyclopent-1-yl]propan-1-ol.

DEFINITE EXAMPLE 46

Methyl (4aS, 7S, 7aR)-1, 4a,5,6,7,7a-hexahydro-1-hydroxy-7-methylcyclopenta[c]pyran-4-carboxylate (1.0 g, 0.0047 mol) obtained in Definite Example 4 was dissolved in 10 ml of anhydrous tetrahydrofuran, and while the reaction mixture was being cooled by ice and stirred, 33 ml of diisobutylaluminum hydride (1.0M tetrahydrofuran solution) was added dropwise. The reaction mixture was stirred at the same temperature for 2 hours and 1.5 ml of acetone was then added, and 6.25 ml of a 3% aqueous sodium hydroxide solution was added dropwise. After the reaction mixture was vigorously stirred for 1 hour, magnesium sulfate was added and the reaction mixture was stirred further for 20 minutes. After celite filtration, the filtrate was concentrated. The residual substance was purified by chromatography using silica gel, and the solvent of the fraction obtained from the ether:ethyl acetate=8:2 eluent was concentrated, and a colorless oily substance was obtained. Since this colorless oily substance had the following physicochemical properties, it was determined as 2-[(1S, 2R, 3S)-2-(hydroxymethyl)-3-methylcyclopent-1-yl]-2-propan-1-ol.

Proton NMR spectrum (δ ppm in CDCl$_3$): 1.05 (3H, d, J=7 Hz), 1.05–1.98 (6H, m), 2.64–2.80 (1H, m), 3.34–3.78 (2H, m), 4.11 (2H, brs), 4.93 (1H, s), 5.18 (1H, s) Mass spectrum m/z (%): 171 (M+H)$^+$

DEFINITE EXAMPLE 47

8.0 g (0.21 mol) of lithium aluminum hydride was suspended in 100 ml of anhydrous tetrahydrofuran, and 150 ml of an anhydrous tetrahydrofuran solution of methyl (1S, 4aS, 7R, 7aR)-1-acetoxy-7-methyl-1,4a,5,6,7,7a-hexahydrocyclopenta[c]pyran-4-carboxylate obtained in Definite Example 52 (14.5 g, 0.057 mol) was added dropwise while being cooled by ice and stirred. The temperature was returned to room temperature and the reaction mixture was stirred for 3 hours. After 300 ml of ether was added, 1N sodium hydroxide solution was further added dropwise. After insoluble matters were filtered by celite, concentration was carried out and the residual substance was purified by chromatography using silica gel. When the solvent of the fraction obtained from ether:ethyl acetate=9:1 eluent was distilled off, and a colorless oily substance was obtained, i.e., 2-[(1S, 2R, 3R)-2-(hydroxymethyl)-3-methylcyclopent-1-yl]-2-propen-1-ol (5.55 g, yield=57.2%). This 2-[(1S, 2R, 3R)-2-(hydroxymethyl)-3-methylcyclopent-1-yl]-2-propen-1-ol had the following physicochemical properties.

Proton NMR spectrum (δ ppm in CDCl$_3$): 1.00 (3H, d, J=7 Hz), 1.16–3.20 (7H, m), 3.36–3.76 (2H, m), 3.46 (2H, brs), 5.00 (1H, s), 5.20 (1H, s) IR absorption spectrum υ neat max cm$^{-1}$: 3420, 2952, 2876, 1454, 1008, 906

DEFINITE EXAMPLE 48

Methyl (1S, 4aS, 7S, 7aR)-1-[1-(ethoxy)ethoxy]-7-methyl-1,4a,5,6,7,7a-hexahydrocyclopenta[c]pyran-4-carboxylate (300 mg, 0.0014 mol) obtained in Definite Example 4 was dissolved in 8 ml of tert-butanol, and after sodium boron hydride (250 mg, 0.007 mol) was added, the reaction mixture was refluxed at 80° C. Furthermore, methanol (1.5 ml) was added dropwise to the reaction solution in the course of 1 hour, and stirring was continued at the same temperature for 1 hour. 10 ml of saturated ammonium chloride solution was added to the reaction mixture, and concentration was once made. Then, extraction was made with ethyl acetate (50 ml×3). The organic layers were Joined, dried by adding magnesium sulfate, filtered and thereafter concentrated under a reduced pressure. The residual substance was purified by chromatography using silica gel, and the solvent of the fraction obtained from ether:ethyl acetate=1:3 eluent was distilled, and a colorless oily substance was obtained, i.e., 2-[(1R, 2R, 3S)-2-(hydroxymethyl)-3-methylcyclopent-1-yl]ethan-1-ol (162 mg, yield=63.1%). This 2-[(1R, 2R, 3S)-2-(hydroxymethyl)-3-methylcyclopent-1-yl]ethan-1-ol had the following physicochemical properties.

Proton NMR spectrum (δ ppm in CDCl$_3$): 1.00 (3H, d, J=6 Hz), 1.17–1.38 (3H, m), 1.62–1.89 (5H, m), 2.12–2.24 (1H, m), 3.56–3.74 (4H, m) IR absorption spectrum υ CHCl$_3$ max cm$^{-1}$: 3612, 3392, 2944, 1452, 1378, 1260, 1004, 896

DEFINITE EXAMPLE 49

2-[(1S, 2R, 3S)-2-(hydroxymethyl)-3-methylcyclopent-1-yl]-2-propan-1-ol (150 mg, 0.00088 mol) obtained in Definite Example 46 was dissolved in 5 ml of ethyl acetate, and after 5 mg of 10% palladium carbon was suspended, the reaction mixture was stirred for 24 hours in a hydrogen atmosphere of 1 atm. After the catalyst was removed by celite filtration, concentration was carried out under a reduced pressure. The residual substance was purified by chromatography using silica gel, and the solvent of the fraction obtained from hexane:ether=1:1 eluent was removed, and a colorless oily substance was obtained, i.e., (1R, 2R, 3S)-2-(hydroxymethyl)-3-methyl-1-(2-propyl)cyclopentane (50 mg, yield=36.3%). This (1R, 2R, 3S)-2-(hydroxymethyl)-3-methyl-1-(2-propyl)cyclopentane had the following physicochemical properties.

Proton NMR spectrum ($\delta$ ppm in CDCl$_3$): 0.88 (3H, d, J=6H), 0.95 (3H, d, J=6 Hz), 1.01 (3H, d, J=7 Hz), 1.06–2.16 (8H, m), 3.34 (1H, t, J=9 Hz), 3.73 (1H, dd, J=4, 10 Hz)

DEFINITE EXAMPLE 50

Methyl (4aS, 7R, 7aR)-1,4a,5,6,7,7a-hexahydro-1-hydroxy-7-methylcyclopenta[c]pyran-4-carboxylate (300 mg, 0.0014 mol) and sodium boron hydride (270 mg, 0.007 mol) were dissolved in 8 ml of tetrahydrofuran, and while the reaction mixture was refluxed at 80° C., 1.5 ml of methanol was added dropwise in the course of 1 hour. The reaction mixture was stirred at the same temperature for 5 hours, and 10 ml of a saturated ammonium chloride solution wad added. The reaction mixture was once concentrated under a reduced pressure, and extraction was made with ethyl acetate (50 ml×2). The organic layers were joined, dried by adding magnesium sulfate, filtered and thereafter concentrated under a reduced pressure. The residual substance was purified by chromatography using silica gel, and the solvent of the fraction obtained from ether:ethyl acetate=1:1 eluent was distilled, and a colorless oily substance was obtained, i.e., 2-[(1R, 2R, 3S)-2-(hydroxymethyl)-3-methylcyclopent-1-yl]ethan-1-ol (169 mg, yield=63.8%). This 2-[(1R, 2R, 3S)-2-(hydroxymethyl)-3-methylcyclopent-1-yl]ethan-1-ol had the following physicochemical properties.

Proton NMR spectrum ($\delta$ ppm in CDCl$_3$): 0.97 (3H, d, J=7 Hz), 1.04–2.14 (9H, m), 2.88 (2H, brs), 3.60–3.74 (4H, m)

DEFINITE EXAMPLE 51

After methyl (1S, 4aS, 7aR)-1-acetoxy-7-(acetoxymethyl)-1,4a,5,7a-tetrahydrocyclopenta[c]pyran-4-carboxylate (100 mg, 0.0003 mol) obtained in Example 21 was dissolved in 5 ml of ethyl acetate, 20% Pd(OH)$_2$-C (5 mg) was added to the solution, and the reaction mixture was stirred for 24 hours in a hydrogen gas atmosphere of 1 atm. The catalyst was removed by celite filtration and the filtrate was concentrated. The residual substance was purified by chromatography using silica gel, and the solvent of the fraction obtained from hexane:ether=2:8 eluent was distilled, and a colorless oily substance was obtained, i.e., methyl (4aS, 7aR)-1,4a,5,6,7,7a-hexahydro-7-methylcyclopenta[c]pyran-4-carboxylate (48 mg, yield=30.4%). This methyl (4aS, 7aR)-1,4a,5,6,7,7a-hexahydro-7-methylcyclopenta[c]pyran-4-carboxylate had the following physicochemical properties.

Proton NMR spectrum ($\delta$ ppm in CDCl$_3$): 1.07 (3H, d, J=9 Hz), 1.16–1.26 (2H, m), 1.64–1.96 (3H, m), 2.22–2.30 (1H, m), 2.70–2.82 (1H, m), 3.49 (1H, t, J=9 Hz), 3.71(3H, s), 4.01 (1H, dd, J=4, 10 Hz), 7.58 (1H, s) Mass spectrum m/z (%): 197 (M+H)+

DEFINITE EXAMPLE 52

Methyl (1S, 4aS, 7aR)-1-acetoxy-7-(acetoxymethyl)-1,4a,5,7a-tetrahydrocyclopenta[c]pyran-4-carboxylate (12.0 g, 0.039 mol) obtained in Example 21 was dissolved in a mixed solvent of 200 ml of methanol and 6.5 ml of pyridine and after 400 mg of PtO$_2$ was added, the reaction mixture was stirred for 24 hours in a hydrogen gas atmosphere of 1 atm. The catalyst was removed by celite filtration, and 500 ml of ethyl acetate was added further to the filtrate. This organic layer was washed by 2N hydrochloric acid solution (200 ml×2), dried by adding magnesium sulfate, filtered, and thereafter concentrated under a reduced pressure. The residual substance was purified by chromatography using silica gel, and the solvent of the fraction obtained from hexane:ether=8:2 eluent was distilled, and a colorless oily substance was obtained, i.e., methyl (1S, 4aS, 7R, 7aR)-1-acetoxy-7-methyl-1,4a,5,6,7,7a-hexahydropenta[c]pyran-4-carboxylate (8.87 g, yield=90.2%). This methyl (1S, 4aS, 7R, 7aR)-1-acetoxy-7-methyl-1,4a,5,6,7,7a-hexahydrocyclopenta[c]pyran-4-carboxylate had the following physicochemical properties.

Proton NMR spectrum ($\delta$ ppm in CDCl$_3$): 1.01 (3H, d, J=7 Hz), 1.16–2.42 (6H, m), 2.12 (3H, s), 2.98 (1H, q, J=12 Hz), 3.72 (3H, s), 6.04 (1H, d, J=6 Hz), 7.38 (1H, s) IR absorption spectrum $\upsilon$ neat max cm$^{-1}$: 2952, 2880, 1708, 1642, 1438, 1372, 1296, 1170, 1090, 956, 902

DEFINITE EXAMPLE 53

2-[(1S, 2R, 3S)-2-(hydroxymethyl)-3-methylcyclopent-1-yl]-2-propan-1-ol (450 mg, 0.0026 mol) obtained in Definite Example 46 was dissolved in 20 ml of dichloromethane, and after 2.3 g (0.026 mol) of manganese dioxide was added, the reaction mixture was refluxed at 50° C. Ten hours later, insoluble matters were removed by celite filtration and the filtrate was concentrated under a reduced pressure. The residual substance was purified by chromatography using silica gel, and the solvent of the fraction obtained from hexane:ether=7:3 eluent was removed, and a colorless oily substance was obtained, i.e., (4aS, 7S, 7aR)-1,4a,5,6,7,7a-hexahydro-7-methyl-4-methylenecyclopenta[c]pyran-3-one (350 mg, yield=80.6%). This (4aS, 7S, 7aR)-1,4a,5,6,7,7a-hexahydro-7-methyl-4-methylenecyclopenta[c]pyran-3-one had the following physicochemical properties.

Proton NFLR spectrum ($\delta$ ppm in CDCl$_3$): 1.08 (3H, d, J=6 Hz), 1.08–2.19 (6H, m), 3.17 (1H, q, J=8 Hz), 4.04 (1H, dd, J=4.9, 11.5 Hz), 4.18 (1H, dd, J=3.9, 11.5 Hz), 5.47 (1H, t, J=1.5 Hz), 6.04 (1H, t, J=1.5 Hz) IR absorption spectrum $\upsilon$ CHCl$_3$ max cm$^{-1}$: 2952, 1732, 1628, 1304, 1154, 950

DEFINITE EXAMPLE 54

(4aS, 7S, 7aR)-1, 4a,5,6,7,7a-hexahydro-7-methyl-4-methylenecyclopenta[c]pyran-3-one (300 mg, 0.0018 mol) obtained in Definite Example 53 was dissolved in 10 ml of ethyl acetate, and after 10% palladium carbon was added, the reaction mixture was stirred for 24 hours, in a hydrogen has atmosphere of 1 atm. After the catalyst was removed by celite filtration, the filtrate was concentrated under a reduced pressure. The residual substance was purified by chromatography using silica gel, and the solvent of the fraction obtained from hexane:ether=7:3 eluent was distilled, and a colorless oily substance was obtained, i.e., (4S, 4aS, 7S, 7aR)-1,3,4,4a,5,6,7,7a-octahydro-4,7-dimethylcyclopenta[c]pyran-3-one (275 mg, yield=90.5%). This (4S, 4aS, 7S, 7aR)-1,3,4,4a,5,6,7,7a-octahydro-4,7-dimethylcyclopenta[c]pyran-3-one had the following physicochemical properties.

Proton NMR spectrum (δ ppm in CDCl$_3$): 0.99–2.00 (2H, m), 1.05 (3H, d, J=6 Hz), 1.15 (3H, d, J=7 Hz), 1.75–1.85 (4H, m), 2.57–2.64 (1H, m), 2.68–2.75 (1H, m), 4.17 (1H, d, J=8 Hz), 4.27 (1H, dd, J=3.3, 11.8 Hz) IR absorption spectrum υ CHCl$_3$ max cm$^{-1}$: 1362, 1282, 1254, 1236, 1178, 1110, 1072, 1024, 984, 914, 774, 720, 646 Mass spectrum m/z (%): 168 (M+)

PREPARATION EXAMPLES

Next, preparations of the iridoid compounds will be explained.

The iridoid compounds can be given to animals and human being either as such or with a customary preparation carrier. The form of dose is not particularly limited, and is selected appropriately whenever necessary. Examples of the preparations are peroral drugs such as tablets, capsules, granules, powders, dust, etc., and parenteral drugs such as injections and suppositories. The peroral drugs are prepared in a customary manner by the use of starch, milk sugar, refined sugar, mannitol, carboxymethyl cellulose, corn starch, inorganic salts, and the like.

Besides the excipients described above, the preparations of this kind can use binders, decompositants, surfactants, lubricants, fluidity promoters, correctives, colorants, perfumes, and so forth. Definite examples thereof are given below.

BINDERS

Examples of the binders include starch, dextrin, gum arabic powder, gelatin, hydroxypropyl starch, methylcellulose, carboxymethylcellulose sodium, hydroxypropyl-cellulose, crystal cellulose, ethylcellulose, polyvinyl-pyrrolidone, macrogol.

Decompositants

Starch, hydroxypropyl starch, carboxymethyl-cellulose sodium, carboxymethylcellulose potassium, carboxymethylcellulose, low substituted hydroxypropyl-cellulose.

Surfactants

Lauryl sodium sulfate, soybean lecithin, cane sugar aliphatic acid esters, polysorbate 80.

Lubricants

Talc, waxes, hydrogenated vegetable oil, cane sugar aliphatic acid esters, magnesium stearate, calcium stearate, aluminum stearate, polyethylene glycol.

Fluidity promoters

Light silicic anhydride, dry alminium hydroxide gel, synthetic aluminum silicate, magnesium silicate.

The iridoid compounds also can be given in the form of a suspension, an emulsion, a syrup, and an elixir. Each of these various preparation forms may contain a taste and odor corrective and a colorant.

The parenteral drugs are prepared in a customary manner, and it is generally possible to use, as a diluting agent, distilled water for injection, a physiological saline solution, an aqueous grape sugar solution, a vegetable oil for injection, a sesami oil, a peanut oil, a soybean oil, a corn oil, propyleneglycol, polyethylene glycol, and so forth.

A pasteurizer, antiseptics and a stabilizer may be added, whenever necessary. From the aspect of stability, this parenteral drug may be refrigerated after being packed into a vial, etc., its moisture content removed by ordinary freezing technique, and a liquid preparation prepared again from the frozen and dry product immediately before use.

Other examples of the parenteral drugs include liniments such as an endemic liniment and an ointment, and suppositories for the administration to the rectum, and are prepared in a customary manner.

Next, the preparation methods will be explained in further detail with reference to Preparation Examples.

Preparation Example 1

| | |
|---|---|
| ①corn starch | 44 g |
| ②crystal cellulose | 40 g |
| ③carboxymethylcellulose calcium | 5 g |
| ④light silicic anhydride | 0.5 g |
| ⑤magnesium stearate | 0.5 g |
| ⑥compound obtained in Definite Example 1 | 10 g |
| total: | 100 g |

The compounds ①–⑥ were uniformly mixed in accordance with the recipe described above and were compression-molded by a tableting machine to obtain 200 mg tablets.

One of these tablets contained 20 mg of the compound obtained in Definite Example 1, and 3 to 10 tablets were dividedly administered several times a day to the adult.

Preparation Example 2

| | |
|---|---|
| ①crystal cellulose | 84.5 g |
| ②magnesium stearate | 0.5 g |
| ③carboxymethylcellulose calcium | 5 g |
| ④compound obtained in Definite Example 2 | 10 g |
| total: | 100 g |

The compounds ① and ④ and a part of the compound ② were mixed uniformly in accordance with the recipe described above, and were compression-molded and then pulverized. Then the balance of ③ and ② were added and mixed, and the mixture was compression-molded by a tableting machine to obtain 200 mg tablets.

One of these tablets contained 20 mg of the compound obtained in Definite Example 2, and 3 to 10 tablets were dividedly administered several times a day to the adult.

Preparation EXAMPLE 3

| | |
|---|---|
| ①crystal cellulos | 34.5 g |
| ②10% hydroxypropylcellulose - ethanol solution | 50 g |
| ③carboxymethylcellulose calcium | 5 g |
| ④magnesium stearate | 0.5 g |
| ⑤compound obtained in Definite Example 3 | 10 g |
| total: | 100 g |

The compounds ①, ② and ⑤ were mixed uniformly in accordance with the recipe described above, kneaded in a customary manner, granulated by a granulating machine, and dried and pulverized. Then, the compounds ③ and were mixed and the mixture was compression-molded by a tableting machine to obtain 200 mg tablets.

One of these tablets contained 20 mg of the compound obtained in Definite Example 3, and 3 to 10 tablets were dividedly administered several times a day to the adult.

Preparation Example 4

| | |
|---|---:|
| ①corn starch | 84 g |
| ②magnesium stearate | 0.5 g |
| ③carboxymethylcellulose calcium | 5 g |
| ④light silicic anhydride | 0.5 g |
| ⑤compound obtained in Definite Example 4 | 10 g |
| total: | 100 g |

The compounds ①-⑤ were mixed uniformly in accordance with the recipe described above, compression-molded by a compression molding machine, pulverized by a pulverizer and then sieved to obtain granules.

1 g of this granule contained 100 mg of the compound obtained in Definite Example 4, and 0.6 to 2 g of the granule was administered dividedly several times a day to the adult.

Preparation Example 5

| | |
|---|---:|
| ①crystal cellulose | 55 g |
| ②10% hydroxypropylcellulose ethanol solution | 35 g |
| ③compound obtained in Definite Example 5 | 10 g |
| total: | 100 g |

The compounds ①-③ were uniformly mixed in accordance with the recipe described above, and were kneaded. After being extruded by an extrusion granulating machine, the resulting product was dried and sieved to obtain granules.

1 g of this granule contained 100 mg of the compound obtained in Definite Example 5, and 0.6 to 2 g was dividedly administered several times a day to the adult.

Preparation Example 6

| | |
|---|---:|
| ①corn starch | 89.5 g |
| ②light silicic anhydride | 0.5 g |
| ③compound obtained in Definite Example 6 | 10 g |
| total: | 100 g |

The compounds ①-③ were uniformly mixed in accordance with the recipe described above, and 200 mg thereof were packed into a No. 2 capsule.

One capsule of this capsule contained 20 mg of the compound obtained in Definite Example 6, and 3 to 10 capsules were dividedly administered several times a day to the adult.

Preparation Example 7

| | |
|---|---:|
| ①distilled water for injection | suitable amount |
| ②grape sugar | 200 mg |
| ③compound obtained in Definite Example 7 | 100 mg |
| total: | 15 ml |

After the compounds ② and ③ were dissolved in distilled water for injection, the solution was charged into a 5 ml ampule and was pressure-sterilized at 121° C. for 15 minutes to obtain an injection.

Industrial Applicability

This invention can be used effectively for preparing a medicine useful as an anti-hyperlipemia agent and a cholagogue.

It is claimed:

1. A iridoid derivative expressed by the formula (11) below:

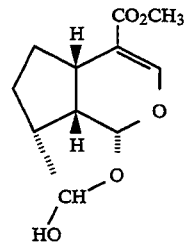

2. An anti-hyperlipemia composition comprising the iridoid derivative of claim 1 as the active principle.

3. A cholagogue composition comprising the iridoid derivative of claim 1 as the active principle.

* * * * *